US008871463B2

(12) United States Patent
Lee et al.

(10) Patent No.: US 8,871,463 B2
(45) Date of Patent: Oct. 28, 2014

(54) METHOD FOR SCREENING A GLUTAMATE RELEASE INHIBITOR IN AN ASTROCYTE

(71) Applicant: Korea Institute of Science and Technology, Seoul (KR)

(72) Inventors: Changjoon Justin Lee, Seoul (KR); Soo Jin Oh, Seoul (KR); Eun Mi Hwang, Jinju (KR); Dong Ho Woo, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/948,476

(22) Filed: Jul. 23, 2013

(65) Prior Publication Data

US 2014/0093490 A1    Apr. 3, 2014

(30) Foreign Application Priority Data

Sep. 28, 2012  (KR) .................. 10-2012-0109460

(51) Int. Cl.
*C12Q 1/02*  (2006.01)
(52) U.S. Cl.
USPC ............................................ 435/29; 435/366
(58) Field of Classification Search
USPC .................................................. 435/29, 366
See application file for complete search history.

(56) References Cited

U.S. PATENT DOCUMENTS

| 2009/0137652 | A1* | 5/2009 | Twyman et al. ............... 514/397 |
| 2009/0209474 | A1* | 8/2009 | Roegel et al. ................... 514/23 |
| 2010/0029613 | A1* | 2/2010 | Nedergaard et al. ...... 514/212.01 |
| 2012/0070407 | A1* | 3/2012 | Lazdunski et al. ............ 424/85.2 |
| 2014/0093490 | A1* | 4/2014 | Lee et al. ....................... 424/94.5 |

FOREIGN PATENT DOCUMENTS

| KR | 10-2009-0105597 | 10/2009 |
| KR | 10-2014-0042559 |  4/2014 |

OTHER PUBLICATIONS

Takano T. et al. Receptor Mediated Glutamate Release from Volume Sensitive Channels in Astrocytes. PNAS 102(45)16466-16471, Nov. 8, 2005.*
Wang F. et al. Photolysis of Caged Ca2+ But Not Receptor Mediated Ca2+ Signaling Triggers Astrocytic Glutamate Release. J of Neuroscience 33(44)17404-12, Oct. 30, 2013.*
Lee C. et al. Astrocytic Control of Synaptic NMDA Receptors. J Physiology 581(3)1057-1081, 2007.*
Bezzi, et al., "Astrocytes contain a vesicular compartment that is competent for regulated exocytosis of glutamate," Nature Neuroscience, vol. 7, No. 6, Jun. 2007, pp. 613-620.
Agulhon, et al., "Hippocampal Short- and Long-Term Plasticity Are Not Modulated by Astrocyte $Ca^{2+}$Signaling," Science, vol. 327, Mar. 2010 pp. 1250-1254.
Cavelier, et al., "Tonic release of glutamate by a DIDS-sensitive mechanism in rat hippocampal slices," Journal of Physiology vol. 564 No. 2, 2005, pp. 397-410.
Jourdain, et al., "Glutamate exocytosis from astrocytes controls synaptic strength," Nature Neuroscience vol. 10, No. 3, Mar. 2007, pp. 331-339.
Woo, et al., "TREK-1 and Best1 Channels Mediate Fast and Slow Glutamate Release in Astrocytes upon GPCR Activation," Cell vol. 151, Sep. 2012, pp. 25-40.
Gordon Research Conference, "Synaptic Transmission," Jul. 29, 2012, pp. 1-4.
15th Conference on The Korean Society for Brain and Neural Science, Sep. 25-26, 2012, Seoul National University, pp. 1-2.

* cited by examiner

*Primary Examiner* — Ralph Gitomer
(74) *Attorney, Agent, or Firm* — Staas & Halsey LLP

(57) ABSTRACT

The present invention investigate the two modes of glutamate release and the releasing rate of glutamate, and thus can provide a useful technique for neuron protection and acceleration of neurotransmission by controlling the glutamate release in astroctye. Thus, the present invention provides an inhibitor of the fast-mode release and/or the slow-mode release of astrocytic glutamate, a screening method of the inhibitor and a pharmaceutical composition or method of ameliorating, preventing and/or treating the disease associated with the over-release of glutamate via the $Ca^{2+}$-activated anion channel, with the inhibition of fast-mode glutamate release.

3 Claims, 91 Drawing Sheets

Full activation

RGS-2

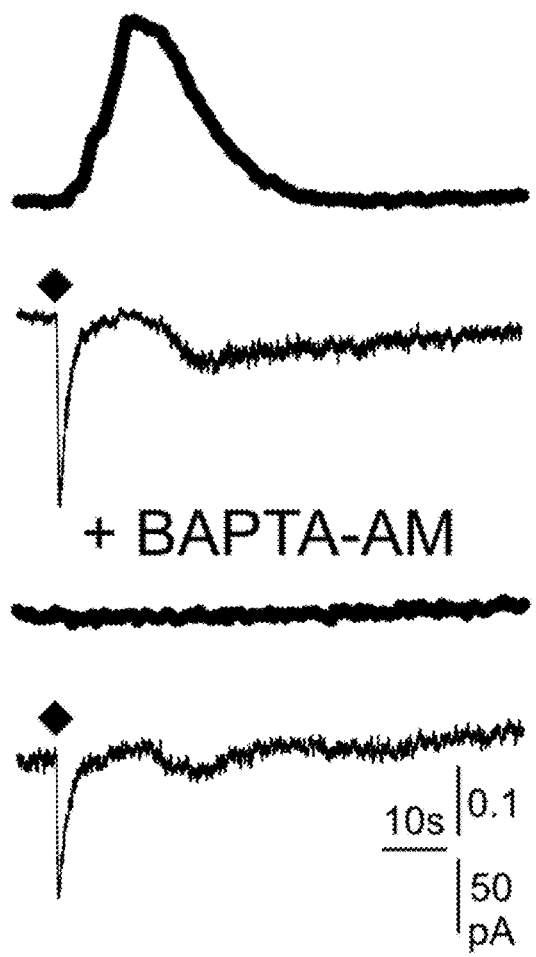

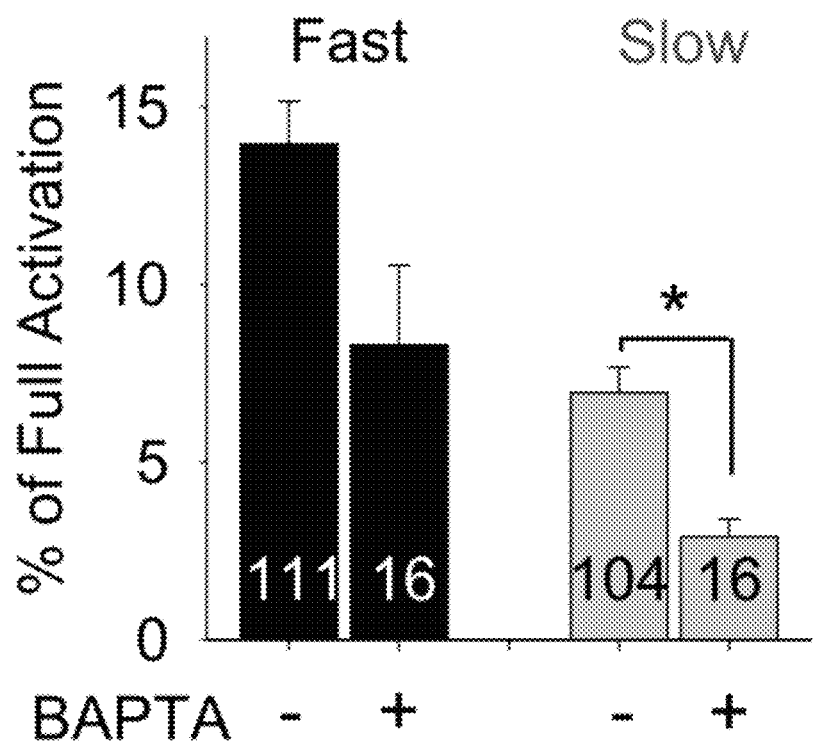

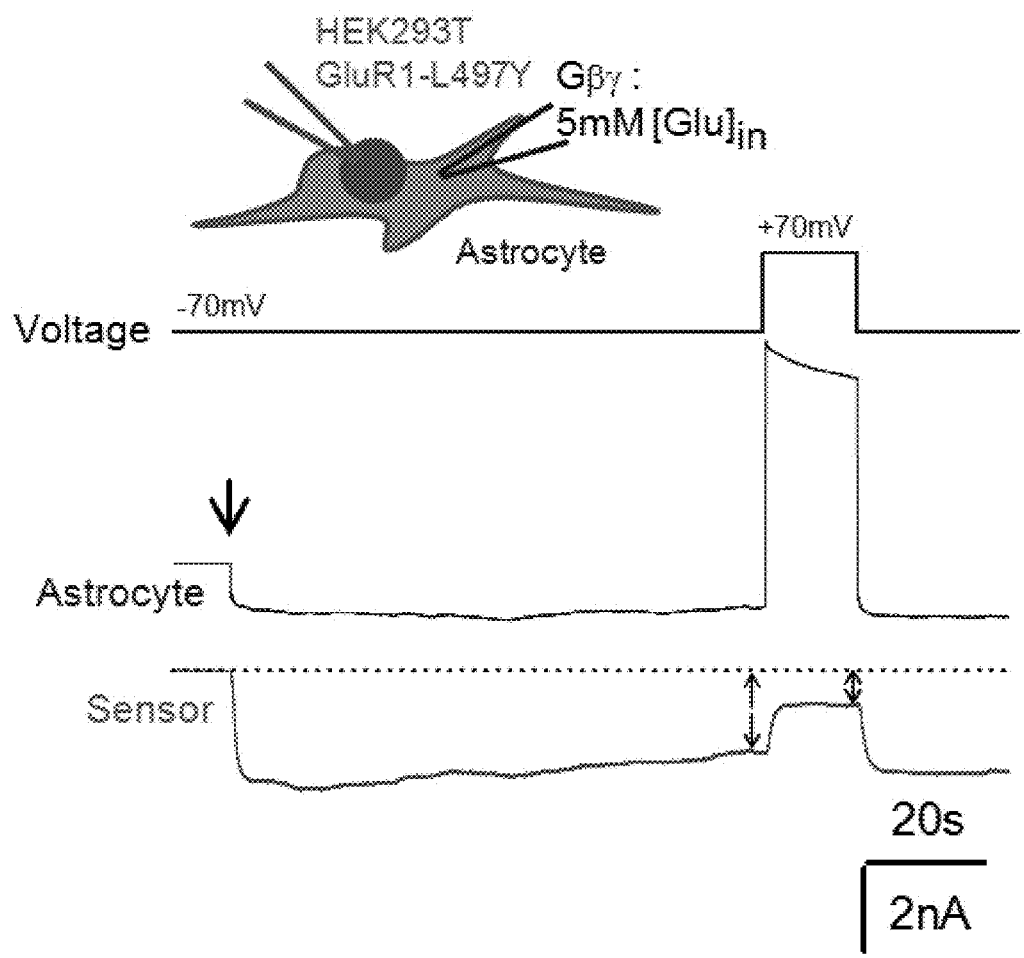

scrambled sh-TR1

10s
1nA

Fig. 5e
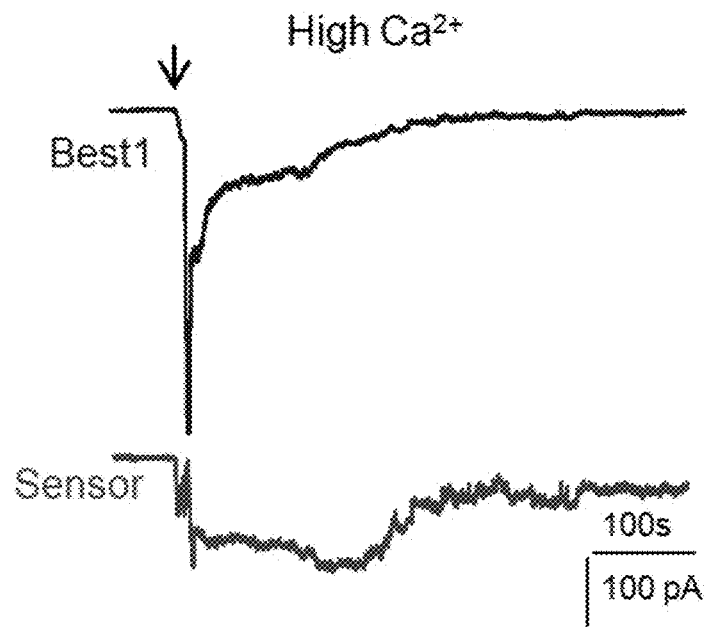
Fig. 5f
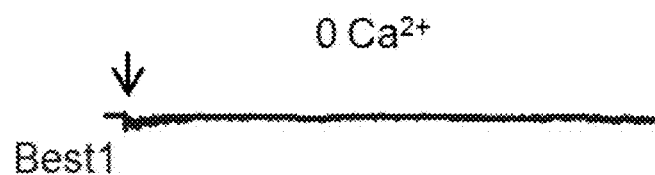
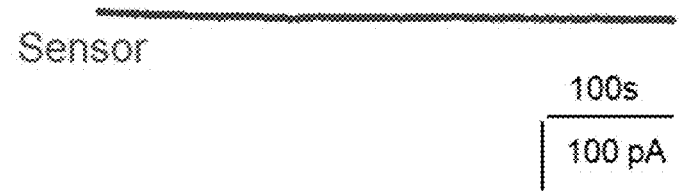

Wild Type
Sh-TREK-1

Best1 KO

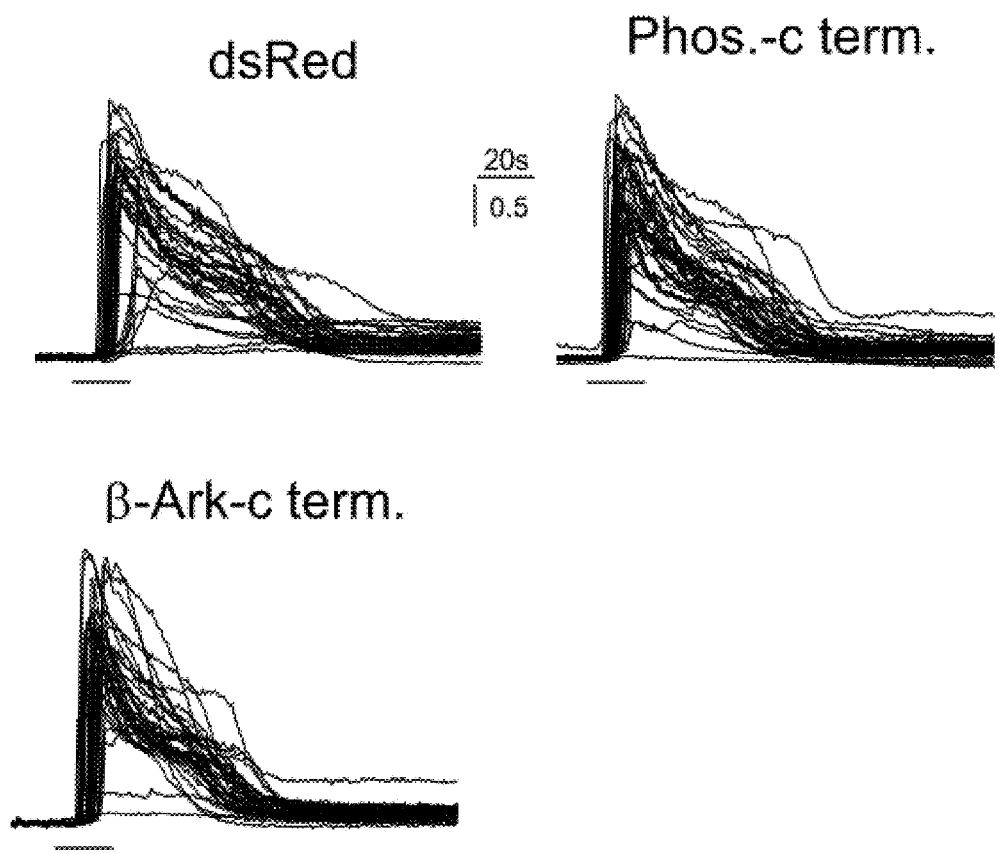

Fig. 10i

Conc.A

Fig. 10j

TeTX

+ BoTox (in astrocyte)

+ BSA (in astrocyte)

TREK-1

N-Full  1 ———————— 46
N1      ——
N2         ——
N3            ——
N4               ——

N1: AAPDLLDPKSA (1-12)
N2: AQNSKPRLSFSS (13-24)
N3: KPTVLASRVES (25-35)
N4: DSAINVMKWKT (36-46)

SEQUENCE LISTING

```
<160> NUMBER OF SEQ ID NOS: 22

<210> SEQ ID NO 1
<211> LENGTH: 21
<212> TYPE: RNA
<213> ORGANISM: Artificial Sequence
<220> FEATURE:
<223> OTHER INFORMATION: TREK-1-shRNA

<400> SEQUENCE: 1
gcguggagau cuacgacaag u                                              21

<210> SEQ ID NO 2
<211> LENGTH: 11
<212> TYPE: PRT
<213> ORGANISM: Artificial Sequence
<220> FEATURE:
<223> OTHER INFORMATION: Competitive peptides N1 of TREK-1

<400> SEQUENCE: 2

Ala Ala Pro Asp Leu Leu Asp Pro Lys Ser Ala
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Competitive peptides N2 of TREK-1

<400> SEQUENCE: 3

Ala Gln Asn Ser Lys Pro Arg Leu Ser Phe Ser Ser
 1               5                  10

<210> SEQ ID NO 4
<211> LENGTH: 11
<212> TYPE: PRT
<213> ORGANISM: Artificial Sequence
<220> FEATURE:
<223> OTHER INFORMATION: Competitive peptides N4 of TREK-1

<400> SEQUENCE: 4

Asp Ser Ala Ile Asn Val Met Lys Trp Lys Thr
 1               5                  10

<210> SEQ ID NO 5
<211> LENGTH: 41
<212> TYPE: PRT
<213> ORGANISM: Artificial Sequence
<220> FEATURE:
<223> OTHER INFORMATION: B-Ark(Beta-adrenergic receptor kinase)
      C-terminus

<400> SEQUENCE: 5

Trp Lys Lys Glu Leu Arg Asp Ala Tyr Arg Glu Ala Gln Gln Leu Val
 1               5                  10                  15

Gln Arg Val Pro Lys Met Lys Asn Lys Pro Arg Ser Val Gln Arg Val
                20                  25                  30

Pro Lys Met Lys Asn Lys Pro Arg Ser
```

```
<210> SEQ ID NO 6
<211> LENGTH: 35
<212> TYPE: PRT
<213> ORGANISM: Artificial Sequence
<220> FEATURE:
<223> OTHER INFORMATION: phosducin C-terminus

<400> SEQUENCE: 6

Gly Glu Phe Met Val Thr Asp Gln Leu Gly Glu Asp Phe Phe Ala Val
 1               5                  10                  15

Asp Leu Glu Ala Phe Leu Gln Glu Phe Gly Leu Leu Pro Glu Lys Glu
            20                  25                  30

Gly Ser Gly
        35

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
ggggaattca tggtcactga ccagctgggg                                    30

<210> SEQ ID NO 8
<211> LENGTH: 33
<212> TYPE: DNA
<213> ORGANISM: Artificial Sequence
<220> FEATURE:
<223> OTHER INFORMATION: primer

<400> SEQUENCE: 8
cccggatccc tattcctttt ctgggagcaa tcc                                33

<210> SEQ ID NO 9
<211> LENGTH: 20
<212> TYPE: DNA
<213> ORGANISM: Artificial Sequence
<220> FEATURE:
<223> OTHER INFORMATION: Best1-shRNA

<400> SEQUENCE: 9
tttgccaact tgtcaatgaa                                               20

<210> SEQ ID NO 10
<211> LENGTH: 54
<212> TYPE: DNA
<213> ORGANISM: Artificial Sequence
<220> FEATURE:
<223> OTHER INFORMATION: complementary oligomer

<400> SEQUENCE: 10
tttgccaact tgtcaatgaa ttcaagagat cattgacaag ttggcaattt tttc         54

<210> SEQ ID NO 11
<211> LENGTH: 58
<212> TYPE: DNA
<213> ORGANISM: Artificial Sequence
<220> FEATURE:
<223> OTHER INFORMATION: complementary oligomer

<400> SEQUENCE: 11
```

```
cgagaaaaaa tcgcatagcg tatgccgttt ctcttgaaaa cggcatacgc tatgcgaa      58
```

<210> SEQ ID NO 12
<211> LENGTH: 45
<212> TYPE: DNA
<213> ORGANISM: Artificial Sequence
<220> FEATURE:
<223> OTHER INFORMATION: primer

<400> SEQUENCE: 12

```
gacagctaca ttcagctcat ctgcatatcc ttcgttctgg gtttc                    45
```

<210> SEQ ID NO 13
<211> LENGTH: 45
<212> TYPE: DNA
<213> ORGANISM: Artificial Sequence
<220> FEATURE:
<223> OTHER INFORMATION: primer

<400> SEQUENCE: 13

```
gaaacccaga acgaaggata tgcagatgag ctgaatgtag ctgtc                    45
```

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14

```
ggtgagccgc tgctggagcc agtac                                          25
```

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15

```
gtactggctc cagcagcggc tcacc                                          25
```

<210> SEQ ID NO 16
<211> LENGTH: 1237
<212> TYPE: DNA
<213> ORGANISM: Artificial Sequence
<220> FEATURE:
<223> OTHER INFORMATION: cDNA of TREK-1(GenBank Accession No. AY727922)

<400> SEQUENCE: 16

```
aggatggcgg cccctgactt gctggatccc aagtctgctg ctcagaactc caaaccgagg    60
ctctcgttct ccgcaaaacc caccgtgctt gcttcccggg tggagagtga ctcggccatt   120
aatgttatga atggaagacg gtctccacg attttcctgg tggtcgtcct ctacctgatc    180
atcggagcca cggtgttcaa ggcgttggag cagcctcagg agatttctca gaggaccacc   240
attgtgatcc agaaacagaa cttcatagcc cagcatgcct gcgtcaactc caccgagctg   300
gatgaactca tccagcaaat agtgacggcc ataaatgcag ggattatccc cttaggaaac   360
aactccaatc aagttagtca ctgggacctc ggaagctctt tcttctttgc cggcactgtt   420
atcacaacca taggatttgg aaacatctcc ccacgaactg aaggtggaaa aatattctgt   480
atcatctatg ccttgctggg aattcccctc tttggttttc tactggctgg ggttggggat   540
cagcttggaa ccatatttgg aaaaggaatt gccaaagtgg aggacacatt tattaagtgg   600
```

```
aatgttagtc agaccaagat tcgtatcatc tcgaccatca tcttcatcct gtttggctgt      660
gtcctcttcg tggctctccc cgccgtcata ttcaagcaca tagaaggctg gagtgccctg      720
gacgccatct actttgtggt catcactctg accaccattg gatttggcga ttatgtggca      780
ggtgggtcgg acattgaata tctggacttc tacaagcccg tcgtgtggtt ctggatcctc      840
gttgggctgg cctactttgc ggctgttctg agcatgattg agactggct acgggtgata       900 tctaagaaga cgaaggaaga ggtgggagag ttcagagcgc atgccgctga gtggacagcc      960
aatgtcacag ccgagttcaa ggaaacaagg aggcggctga gtgtggagat ctatgacaag     1020
ttccagcgtg ccacgtccgt gaagcggaag ctctctgcag agctggcggg taaccataac     1080
caggaactga ctccatgtag gaggaccctg tcggtgaacc acctgaccag cgagagggaa     1140
gtcctgcctc ccttgctgaa ggctgagagc atctatctga acggtctgac accacactgt     1200
gctgctgaag acatcgctgt cattgagaac atgaagt                              1237
```

<210> SEQ ID NO 17
<211> LENGTH: 21
<212> TYPE: DNA
<213> ORGANISM: Artificial Sequence
<220> FEATURE:
<223> OTHER INFORMATION: target sequence of TREK-1-shRNA

<400> SEQUENCE: 17
gcgtggagat ctacgacaag t                                                 21

<210> SEQ ID NO 18
<211> LENGTH: 55
<212> TYPE: DNA
<213> ORGANISM: Artificial Sequence
<220> FEATURE:
<223> OTHER INFORMATION: pSicoR-scrambled-shRNA

<400> SEQUENCE: 18
ttcgcatagc gtatgccgtt ttcaagagaa acggcatacg ctatgcgatt ttttc            55

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
tggctacggg tgatctctaa g                                                 21

<210> SEQ ID NO 20
<211> LENGTH: 22
<212> TYPE: DNA
<213> ORGANISM: Artificial Sequence
<220> FEATURE:
<223> OTHER INFORMATION: primer

<400> SEQUENCE: 20
gctggaactt gtcgtagatc tc                                                22

<210> SEQ ID NO 21
<211> LENGTH: 24
<212> TYPE: DNA
<213> ORGANISM: Artificial Sequence
<220> FEATURE:
<223> OTHER INFORMATION: primer -continued

```
<400> SEQUENCE: 21
gtggagtcat actggaacat gtag                                          24

<210> SEQ ID NO 22
<211> LENGTH: 19
<212> TYPE: DNA
<213> ORGANISM: Artificial Sequence
<220> FEATURE:
<223> OTHER INFORMATION: primer

<400> SEQUENCE: 22
aatggtgaag gtcggtgtg                                                19
```

METHOD FOR SCREENING A GLUTAMATE RELEASE INHIBITOR IN AN ASTROCYTE

CROSS-REFERENCE TO RELATED APPLICATION

This application claims priority to and the benefit of Korean Application No. 10-2012-0109460, filed in the Korea Intellectual Property Office on Sep. 28, 2012, the entire contents of which are incorporated herein by reference.

TECHNICAL FIELD

The present invention relates to a glutatamate-release inhibitor, a method or a pharmaceutical composition of treating the pathological symptoms caused by over-release of glutamate in an astrocyte, and a method for screening a novel glutamate-release inhibitor in the astrocyte.

BACKGROUND ART

Astrocytes play an important role in the maintenance of normal brain activity as well as the brain development. Astrocytes have been reported to help the neuron activity by removing released neurotransmitters or adjusting the ion concentration in a brain during last several decades. Recently, astrocyts are involved in the synapse formation, the control of number of synapse, and flexibility of synapse, and also functions in the differentiation of nerve stem cell to nerve tissue.

Glutamate is the principal excitatory neurotransmitter in the brain. In the central nervous system, both neurons and astrocytes are known to release glutamate; the neuronal glutamate mediates fast synaptic transmission, whereas the astrocytic glutamate appears to modulate synaptic transmission. While it is clear that neurons release glutamate via $Ca^{2+}$-dependent exocytosis, the mechanism of astrocytic glutamate release has been heavily debated and many controversial issues have been raised.

The mechanism on the release of astrocytic seems to be divided into three conflicting views: (1) astrocytes release glutamate by vesicular exocytosis just like neurons (Bezzi et al., Nat Neurosci 7, 613-620, 2004; Jourdain et al., Nat Neurosci 10, 331-339, 2007), (2) $Ca^{2+}$-dependent astrocytic glutamate does not do anything important (Agulhon et al., Science 327, 1250-1254, 2010), or (3) glutamate is released from astrocytes by transporters or channels (Cavelier and Attwell, J Physiol 564, 397-410, 2005), molecular mechanism of release has been controversial.

SUMMARY OF THE INVENTION

To resolve the problems of prior arts, the present inventors investigate a molecular mechanism of glutamate release from an astrocyte. An embodiment of the present invention provides a glutamate-release inhibitor which is adapted for inhibition of glutamate released from an astrocyte in non-vesicular and channel-mediated mode.

Another embodiment provides a method of preventing or treating a disease associated with a non-vesicular and channel-mediated release of glutamate from an astrocyte, comprising administering to a subject in heed thereof a pharmaceutically effective amount of the glutamate-release inhibitor.

Additional embodiment provides a pharmaceutical composition for preventing or treating a disease associated with a non-vesicular and channel-mediated release of glutamate from an astrocyte, comprising the glutamate-release inhibitor.

Further embodiment provides a method for screening a glutamate-release inhibitor in an astrocyte.

DETAILED DESCRIPTION OF THE EMBODIMENTS

An embodiment of the present invention relates to a glutamate-release inhibitor, which is adapted for inhibition of glutamate released from an astrocyte in non-vesicular and channel-mediated mode through a glutamate-permeable potassium channel or $Ca^{2+}$-activated anion channel in the astrocyte.

An embodiment of the present invention relates to a method of preventing or treating a disease associated with a non-vesicular and channel-mediated release of glutamate from an astrocyte, comprising administering to a subject in heed thereof a pharmaceutically effective amount of the glutamate-release inhibitor which is adapted for inhibition of glutamate release from an astrocyte in non-vesicular and channel-mediated mode through a glutamate-permeable potassium channel or $Ca^{2+}$-activated anion channel in the astrocyte.

An embodiment of the present invention relates to a method for screening a glutamate-release inhibitor in an astrocyte, said method comprising the steps of: preparing an astrocyte-containing sample; contacting a candidate material to the sample; and detecting the activation of a glutamate-permeable potassium channel or $Ca^{2+}$-activated anion channel in the sample, wherein said candidate material is determined to be glutamate-release inhibitor in an astrocyte when the channel is found to be inactivated.

An embodiment of the present invention relates to a pharmaceutical composition for preventing or treating a disease associated with a non-vesicular and channel-mediated release of glutamate from an astrocyte, comprising the glutamate-release inhibitor which is adapted for inhibition of glutamate released from an astrocyte in non-vesicular and channel-mediated mode through a glutamate-permeable potassium channel or $Ca^{2+}$-activated anion channel in the astrocyte.

The potassium channel is TREK-1 channel, or $Ca^{2+}$-activated anion channel is Bestrophin-1 channel. The inhibitor is at least an inhibitor of potassium channel selected from the group consisting of the inhibitors of activation of G protein-coupled receptor, $G\alpha_i$, activation, $G_{\alpha i}$-$G_{\beta\gamma}$ dissociation, binding of $G_{\beta\gamma\square}$ to N-terminus of TREK-1, and opening of the potassium channel in the astrocyte. The inhibitor is at least one inhibitor of $Ca^{2+}$-activated anion channel selected from the group consisting of the inhibitors of activation of G protein-coupled receptor, increase of $Ca^{2+}$ concentration, signaling pathway of $G_{\alpha q}$, and opening of the $Ca^{2+}$-activated anion channel in the astrocyte.

The present invention will be described in more detail.

Glutamate is the principal excitatory neurotransmitter in the brain. When glutamate is over-released, it becomes a neural toxin to kill the nerve cell. Thus, it is very important to maintain the constant level of glutamate. The acute and degenerative or chronic brain diseases caused by the neural toxicity of glutamate has been studied.

The present inventors investigate the two modes of glutamate release and the releasing rate of glutamate by the activation of G-protein coupled receptor on the astrocyte. For the fast-mode release of glutamate, in case that the astrocyte is treated with an activating agent of G-protein coupled receptor and then tested by sniffer patch method, the onset current ranges 50 to 400 ms after the treatment of the activating agent. For the slow-release of glutamate, in case that the astrocyte is treated with an activating agent of G-protein coupled receptor and then tested by sniffer patch method, the onset current ranges from 50 to 400 ms after the treatment of the activating agent. For the slow-release of glutamate, the peak current ranges from 20 to 50 s. The activating agent of G-protein coupled receptor can be any activating agent of G-protein coupled receptor, for example TFLLR.

The present inventors investigated the mechanism of astrocytic glutamate release using sniffer patch technique, and found that the glutamate was released from an astrocyte in non-vesicular and channel-mediated mode through a glutamate-permeable potassium channel or $Ca^{2+}$-activated anion channel in the astrocyte. By identifying the mechanism of glutamate release via two channel-mediated modes where the fast-mode release is associated with a glutamate-permeable potassium channel such as TREK-1 channel and the slow-mode release is associated with $Ca^{2+}$-activated anion channel in the astrocyte, such as a Best1 channel.

Depending on the mode of glutamate release, the relevant diseases are different. Thus, the investigation of the mechanism of glutamate release in an astrocyte can approach closely to the development of the drug for ameliorating, preventing and/or treating the diseases, and the screening and researching the drug candidate.

In an embodiment of the present invention, the present inventors investigate that the fast-mode release of astrocytic glutamate can be mediated by a potassium channel, for example TREK-1, thereby developing or providing a drug for ameliorating, preventing and/or treating the disease associated with the over-release of glutamate via the potassium channel, with the inhibition of fast-mode glutamate release.

In another embodiment, the present inventors investigate that the slow-mode release of astrocytic glutamate can be mediated by $Ca^{2+}$-activated anion channel in the astrocyte, such as a Best1 channel, thereby developing or providing a drug for ameliorating, preventing and/or treating the disease associated with the over-release of glutamate via the $Ca^{2+}$-activated anion channel, with the inhibition of fast-mode glutamate release.

The fast-mode release of astrocytic glutamate involves the steps of activation of G protein-coupled receptor in the astrocyte, $G_{\alpha i}$ activation mediated by the activation of G protein-coupled receptor, $G_{\alpha i}$-$G_{\beta \gamma}$ dissociation mediated by $G_{\alpha i}$ activation, binding of $G_{\beta \gamma \square}$ to N-terminus of TREK-1 mediated by $G_{\alpha i}$-$G_{\beta \gamma}$ dissociation, and opening of the potassium ion channel mediated by binding of $G_{\beta \gamma \square}$ to N-terminus of TREK-1.

The slow-mode release of astrocytic glutamate involves the steps of activation of G protein-coupled receptor in the astrocyte, $G_{\alpha q}$ signaling activation mediated by the activation of G protein-coupled receptor, the intracellular increase of $Ca^{2+}$ level mediated by $G_{\alpha q}$ signaling activation, and opening of the chloride ion channel such as Best 1 channel mediated by the intracellular increase of $Ca^{2+}$ level. The $Ca^{2+}$-activated anion channel can be one encoded by Bestrophin 1 gene (Best1) that is expressed on astrocyte. Said Bestrophin 1 is a type of chloride ion channels, and used as a representative case for showing that the anion channel is permeable to glutamate. Said Bestrophin 1 gene may be mammal-, preferably rodent- or primate-originated one; for instance, it may be mouse Bestrophin 1 (mBest1) gene.

The G protein-coupled receptor can be any G protein-coupled receptor known in the art, for examples P2Y receptor, bradykinin receptor and protease activated receptors (PARs). According to the present invention, The PAR is expressed in astrocyte at a large amount particularly, compared with other nerve tissue. Thus, in a preferred embodiment, the G protein-coupled receptor is PAR. In considering the beneficially pharmaceutical and molecular means, the specific expression amount in astrocyte, and neurophysiologic process, the embodiment of present invention uses PAR1 as G protein-coupled receptor, but not limited thereto.

The glutamate-release inhibitor of fast-mode release of glutamate, for example an inhibitor of TREK-1 channel includes an inhibitor blocking at least one reaction selected from activation of G protein-coupled receptor, $G_{\alpha i}$, activation, $G_{\alpha i}$-$G_{\beta \gamma}$ dissociation, binding of $G_{\beta \gamma \square}$ to N-terminus of TREK-1, and opening of the potassium channel such as TREK-1 channel in the astrocyte.

The glutamate-release inhibitor of fast-mode release of glutamate includes a compound or a peptide inhibiting opening the TREK-1 channel. For example, the inhibitor can be at least one selected from Quinine and TREK-1-shRNA comprising a nucleotide sequence of SEQ ID NO: 1.

The glutamate-release inhibitor of fast-mode release of glutamate includes a compound or a peptide blocking the binding of $G_{\beta \gamma}$ with the N-terminal peptide of TREK, thereby inhibiting opening the TREK-1 channel.

The glutamate-release inhibitor includes a compound or a peptide competing the binding to TREK-1 with $G_{\beta \gamma}$, a compound or a peptide competing the binding to $G_{\beta \gamma}$ with TREK-1, $G_{\beta \gamma}$ and/or a compound or a peptide being capable of binding to TREK-1 and changing its function, and a peptide competing with N1 domain, N2 domain and N4 domain of TREK-1. The examples of peptide competing with the domains of TREK-1 are a peptide comprising an amino acid sequence of SEQ ID NO: 2 (a peptide competing with N1 of TREK-1, AAPDLLDPKSA), a peptide comprising an amino acid sequence of SEQ ID NO: 3 (a peptide competing with N2 of TREK-1, AQNSKPRLSFSS). The preferable inhibitor includes a peptide comprising an amino acid sequence of SEQ ID NO: 4 (a peptide competing with N4 of TREK-1, DSAINVMKWKT), and preferably a peptide comprising an amino acid sequence of SEQ ID NO: 2, a peptide comprising an amino acid sequence of SEQ ID NO: 3, and a peptide comprising an amino acid sequence of SEQ ID NO: 4.

The glutamate-release inhibitor of fast-mode release of glutamate includes a compound or a peptide blocking the dissociation of $G_{\alpha i}$-$G_{\beta \gamma}$, thereby inhibiting the binding of the dissociated $G_{\beta \gamma}$ to the N-terminal part of TREK-1 and opening the TREK-1 channel, such as Pertussis toxin.

The glutamate-release inhibitor of fast-mode release of glutamate includes a compound or a peptide inhibiting the activation of $G_{\alpha i}$ in an astrocyte, thereby the dissociation of $G_{\alpha i}$-$G_{\beta \gamma}$ the binding of the dissociated $G_{\beta \gamma}$ to the N-terminal part of TREK-1 and opening the TREK-1 channel. The examples of these inhibitors include a C-terminal peptide of β-Ark (Beta-adrenergic receptor kinase) (SEQ ID NO: 5) and a C-terminal segment of Phosducin (SEQ ID NO: 6).

The glutamate-release inhibitor of fast-mode release of glutamate includes a compound or a peptide inhibiting the activation of G protein-coupled receptor in the astrocyte, thereby suppressing the activation of $G_{\alpha i}$, the dissociation of $G_{\alpha i}$-$G_{\beta \gamma}$, the binding of the dissociated $G_{\beta \gamma}$ to the N-terminal part of TREK-1 and opening the TREK-1 channel. When the G protein-coupled receptor is PAR-1, the glutamate-release inhibitor can be at least one selected from FR 171113, SCH 79797 and RWJ 56110. When the G protein-coupled receptor is Canabinoid receptor 1, the glutamate-release inhibitor can be AM 251. When the G protein-coupled receptor is $GABA_B$ receptor, the glutamate-release inhibitor can be at least one selected from CGP 35348, SCH 50911 and Saclofen. When the G protein-coupled receptor is Adenosine receptor 1, the glutamate-release inhibitor can be at least one selected from 8-cyclopentyl-1,3-dipropyl Xanthine (DPCPX), FK-453, BG-9719 and 8-cyclopentyl-1,3-dimethylxanthine (CPX, 8-cyclopentyltheophyl line).

An embodiment of the present invention provides a method of preventing, improving, alleviating, and/or treating a disease or a symptom caused by over-release of glutamate. The diseases includes one or more kinds selected from the group consisting of memory-related diseases (Alzheimer, memory loss with aging, and etc.), seizures, excitotoxicity, ischemia, cerebral apoplexy, cerebral hemorrhage, epilepsy, brain injuries, and hypoxia.

The glutamate-release inhibitor of slow-mode release of glutamate, for example an inhibitor of Best 1 channel includes an inhibitor blocking at least one reaction selected from activation of G protein-coupled receptor, $G_{aq}$ signaling activation, the intracellular increase of $Ca^{2+}$ level, and opening of the chloride ion channel such as Best 1 channel.

The glutamate-release inhibitor of slow-mode release of glutamate includes a compound or a peptide inhibiting opening the Best 1 channel. For example, the inhibitor can be at least one selected from 5-nitro-2-(pheynylpropylamino)-benzoate (NPPB), niflumic acid (NFA), and Dihydro-4,4'-diisothiocyanostylbene-2,2'-disulphonic acid (DIDS).

The glutamate-release inhibitor of slow-mode release of glutamate includes a compound or a peptide inhibiting the increase of intracellular $Ca^{2+}$ concentration, thereby inhibiting opening the Best 1 channel. For example, the inhibitor can be at least one selected from 1,2-bis(o-aminophenoxy)ethan-N,N,N',N'-tetraacetic acid (BAPTA-AM) and regulator of G-protein signaling-2 (RGS-2).

The glutamate-release inhibitor of slow-mode release of glutamate includes a compound or a peptide inhibiting $G_{aq}$ signaling activation, thereby suppressing the increase of intracellular $Ca^{2+}$ concentration and opening the Best 1 channel. For example, the inhibitor can be regulator of G-protein signaling-2 (RGS-2).

The glutamate-release inhibitor of slow-mode release of glutamate includes a compound or a peptide inhibiting activation of G protein-coupled receptor, thereby suppressing $G_{aq}$ signaling activation, the increase of intracellular $Ca^{2+}$ concentration and opening the Best 1 channel.

The pharmaceutical composition further comprises a pharmaceutically-acceptable carrier, diluent, and expient as well as an active ingredient.

The pharmaceutical composition can be prepared as a general pharmaceutical formulation. The pharmaceutical composition can be administered by any suitable route in the form of a pharmaceutical composition adapted to such a route, and in a dose effective for the treatment or prevention intended. Therapeutically effective doses of the composition required to treat or prevent the progress of the medical condition are readily ascertained by one of ordinary skill in the art using preclinical and clinical approaches familiar to the medicinal arts.

The composition of the present invention and the pharmaceutically acceptable salts thereof may be administered by any suitable route, preferably in the form of a pharmaceutical composition adapted to such a route, and in a dose effective for the treatment or prevention intended. The active agent, pharmaceutically acceptable salts thereof and compositions, for example, may be administered orally, rectally, parenterally, or topically.

In certain embodiments, the inhibitor is present in a solid pharmaceutical composition that may be suitable for oral administration. A solid composition of matter according to the present invention may be formed and may be mixed with an excipient, diluted by an excipient or enclosed within such a carrier which can be in the form of a capsule, sachet, tablet, paper, or other container. When the excipient serves as a diluent, it may be a solid, semi-solid, or liquid material which acts as a vehicle, carrier, or medium for the composition of matter.

The dosage regimen for compositions is based on a variety of factors, including the type, age, weight, sex and medical condition of the patient; the severity of the condition; the route of administration; and the activity of the particular inhibitor employed. Thus, the dosage regimen may vary widely. Dosage levels of the order from about 0.01 mg to about 100 mg per kilogram of body weight per day are useful in the treatment or prevention of the above-indicated conditions. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

In an embodiment, there is provided a method for screening a glutamate-release inhibitor in an astrocyte, said method comprising the steps of: preparing an astrocyte-containing sample; contacting a candidate material to the sample; and detecting the activation of a glutamate-permeable potassium channel or $Ca^{2+}$-activated anion channel in the sample, wherein said candidate material is determined to be glutamate-release inhibitor in an astrocyte when the channel is found to be inactivated.

In the screening method, the astrocyte-containing sample can be obtained from mammals, such as those from rodents or primates, for example human. The exemplified sample includes a tissue or a cell isolated from the mammals, preferably the astrocyte cell or hippocampus cells of human primary Cerebral cortex, but not limited thereto.

The candidate material can be an inhibitor of glutamate release in a fast-mode or slow-mode in astrocyte, for examples oligonucleotide, peptide, gene, and protein, but not limited thereto.

The detection of activation of glutamate-permeable potassium channel or $Ca^{2+}$-activated anion channel, can be performed by measuring the change in inward current in astrocytes after inactivating all other receptors and channels on astrocytes than the channel. For instance, an increased inward current value after the treatment with a candidate substance indicates that the channel have become activated, while a decreased inward current value after the treatment with the candidate substance indicates that the channel have become inactivated.

Determination of whether the Best1 channel is activated can be performed using any method known in the technology field to which the present invention belongs. For example, the determination can be made in a manner in which other channels and receptors are made inactive except the Best1 channel in the cerebellar glial cells, and then inward current changes are measured. Increased inward currents after the treatment of a candidate suggest that the Best1 channel is activated, whereas decreased inward currents after the treatment of a candidate suggest that the Best1 channel is inactivated. Inactivation of other channels and receptors and determination of inward currents are of technology widely known in the technology field to which the present invention belongs, and those skilled in the art can perform easily. For instance, determination of inward currents can be carried out using sniffer patch technique (see 'Lee, C. J. et al. Astrocytic control of synaptic NMDA receptors. J Physiol 581, 1057-81 (2007)', which is incorporated hereto as a reference).

EFFECT OF THE INVENTION

The present invention investigate the two modes of glutamate release and the releasing rate of glutamate, and thus can provide a useful technique for neuron protection and acceleration of neurotransmission by controlling the glutamate release in astrocyte. Thus, the present invention provides an inhibitor of the fast-mode release and/or the slow-mode release of astrocytic glutamate, a screening method of the inhibitor and a pharmaceutical composition or method of ameliorating, preventing and/or treating the disease associated with the over-release of glutamate via the $Ca^{2+}$-activated anion channel, with the inhibition of fast-mode glutamate release.

BRIEF DESCRIPTION OF DRAWINGS

FIG. 1n shows the representative traces for before and after 20 μM BAPTA-AM (30 min) treatment in the same astrocyte/sensor cell. The diamond indicates TFLLR application (100 ms, 500 μM).

FIG. 1o is a summary graph for % of full activation for BAPTA-AM treatment. (*, p=0.031). All values are mean±s.e.m.

FIG. 2l shows a summary graph for astrocytes, over-expressing TREK-1-shRNA and co-expressing rat TREK-1 cDNA, wild type and G144E pore mutant form of rat TREK-1 which are insensitive for TREK-1-shRNA. (***, p=0.0004; *1, p=0.047; *2, p=0.012; *3, p=0.048).

FIG. 4a to FIG. 4i show that TREK-1 is gate for glutamate release by direct binding of $G_{\beta\gamma}$ protein.

FIG. 4a is a schematic diagram that shows two cell sniffer patch assay. Green cell represents HEK cell expressing GluR1-L497Y. Blue cell represents astrocyte. Blue lines represent capillary pipette containing 5 mM glutamate and 6.09 nM $G_{\beta\gamma}$. Green lines represent capillary pipette for patching sensor cell. First blue trace shows the change of holding voltage (Vh) on astrocyte. The change of Vh is from −70 mV to 70 mV to modulate glutamate release. The representative traces show current traces both from astrocyte (middle blue) and HEK cell expressing GluR1-L497Y (green). Arrow indicates rupture point indicating 6.09 nM $G_{\beta\gamma}$ protein injection. At Vh=+70 mV from astrocyte (middle blue), the current amplitude of GluR1L497Y-mediated current (Green) indicating glutamate release is reduced. Dot line is the base line for current. Arrows indicate the measurement for glutamate-induced currents.

FIG. 4b is a summary bar graph for % of full activation on indicated conditions. Values are mean±s.e.m (*, p=0.032).

FIG. 4c is a summary bar graph for % of current reduction in response to voltage step.

FIG. 4d shows the Two-cell sniffer assay. Blue trace is $G_{\beta\gamma}$-induced recorded from astrocyte expressing control Scrambled shRNA. Green trace is recorded from the sensor cell. Arrow indicates time for rupture on astrocyte.

FIG. 4e shows that Both $G_{\beta\gamma}$-induced current in TREK-1-shRNA expressing astrocyte and the sensor current in GluR1-L497Y-expressing HEK cell are abolished.

FIG. 4f is a summary bar graph for % of full activation of the sensor current (green). (**, p=0.008; *1, p=0.041; *2, p=0.038). All values are mean±s.e.m.

FIG. 4g is a current trace (blue) recorded from primary cultured astrocyte injected with $G_{\beta\gamma}$ and N3 non-competitive peptide and current trace (green) recorded from HEK cell expressing GluR1-L497Y.

FIG. 4h is a Current trace (blue) recorded from primary cultured astrocyte injected with $G_{\beta\gamma}$ and N1 competitive peptide and current trace (green) recorded from HEK cell expressing GluR1-L497Y. Black arrow indicates rupture point. Red arrow indicates measuring point.

FIG. 4i is a summary bar graph for % of full activation (current amplitude indicated by red arrow/1 mM glutamate-induced full activation×100). Values are mean±s.e.m. (1, p=0.005; 2, p=0.001; n.s., non-significance).

FIG. 5a to FIG. 5f show the Best1 channels contribute to glutamate release by Ca2+.

FIG. 5a shows the representative I-V relationships from whole-cell patch clamp recording in HEK293T cells expressing mouse Best1. The each current was induced by the pipette solution containing 4.5 μM $Ca^{2+}$+145 mM Cl$^-$ (Cs—Cl, black trace), 4.5 μM of $Ca^{2+}$+145 mM of glutamate (Cs-glutamate, red trace), or 0 μM $Ca^{2+}$+145 mM Glutamate (Cs-Glutamate(0 $Ca^{2+}$), green trace). Untransfected HEK293T cells were tested using the pipette solution containing 4.5 μM of $Ca^{2+}$+145 mM Cl$^-$ (untransfected, blue trace) as a negative control.

FIG. 5b is a summary bar graph representing the averaged current amplitudes at −70 mV (*, p=0.03, unpaired t-test) from each group in FIG. 1A. The numbers of cell from at least two independent culture batches are indicated on the bar graph.

FIG. 5c shows a schematic diagram for two-cell biosensor micro-assay using Best1-(source cell) and GluR1L497Y-expressing (sensor cell) HEK293T cells. The released glutamate from the source cell could be detected by GluR1L497Y mutant from the sensor cell at holding potential of −70 mV.

FIG. 5d is a summary bar graph representing the averaged responses in sensor cell. The source cells such as wild type Best1-expressing cells, untransfected cells or Best1W93C (pore mutant)-expressing cells with 4.5 mM $Ca^{2+}$+145 mM glutamate-containing pipette solution, Best1-expressing cells with 0 μM $Ca^{2+}$+145 mM glutamate-containing pipette solution, and Best1-expressing cells with 4.5 mM $Ca^{2+}$+145 mM chloride-containing pipette solution (1, p=0.005, *, p=0.004, **2, p=0.005, *, p=0.011). The determined cell numbers from at least two independent culture batches are indicated on each bar.

FIG. 5e to FIG. 5f show the representative traces demonstrating two-cell sniffer-patch measurements from mBest1-expressing source cell (Best1, blue) and GluR1L497Y-expressing sensor cells (GluR1, green). Best1-expressing cells were patch clamped and ruptured using 145 mM glutamate-containing pipette solution with high $Ca^{2+}$ (4.5 μM; FIG. 5e) or 0 μM $Ca^{2+}$ (FIG. 5f). Arrowheads indicate the time point of rupture of source cell for achieving whole-cell mode. All average values are expressed as mean±s.e.m.

FIG. 6a shows DIC, GFP (astrocyte), ds-Red (sensor cell) images for sniffer-patch from acutely dissociated CA1 hippocampal astrocyte prepared from adult GFPA-GFP mouse.

FIG. 6b shows sensor current traces from one astrocyte before and during 10 μM CNQX.

FIG. 6c is a summary bar graph.

FIG. 6d to FIG. 6e represent an electron microscopic immunostaining for Best1 (FIG. 6d) and TREK-1 (FIG. 6e)

combined with immunostaining for GFP in hippocampal CA1 of GFAP-GFP mouse. Best1 and TREK-1 are stained with immunogold with silver enhancement (dark specks, arrowheads) and GFP is stained with immunoperoxidase (dark amorphous deposits, arrows). Pr: pre-synapse; Po: post-synapse.

Figure 6A:
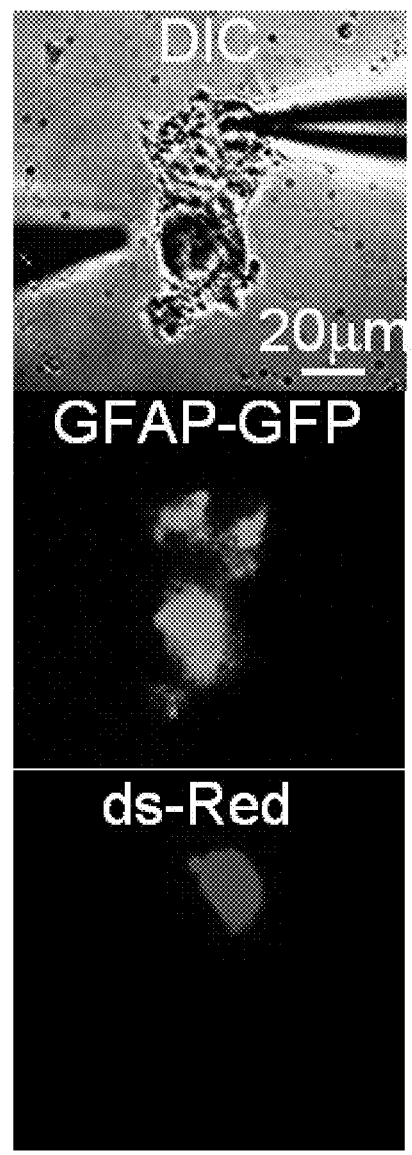
FIG. 6a to FIG. 6g show the acutely dissociated astrocytes show fast and slow glutamate release and differential localization of TREK-1 and Best1 in CA1 hippocampal astrocytes.
Figure 6B:
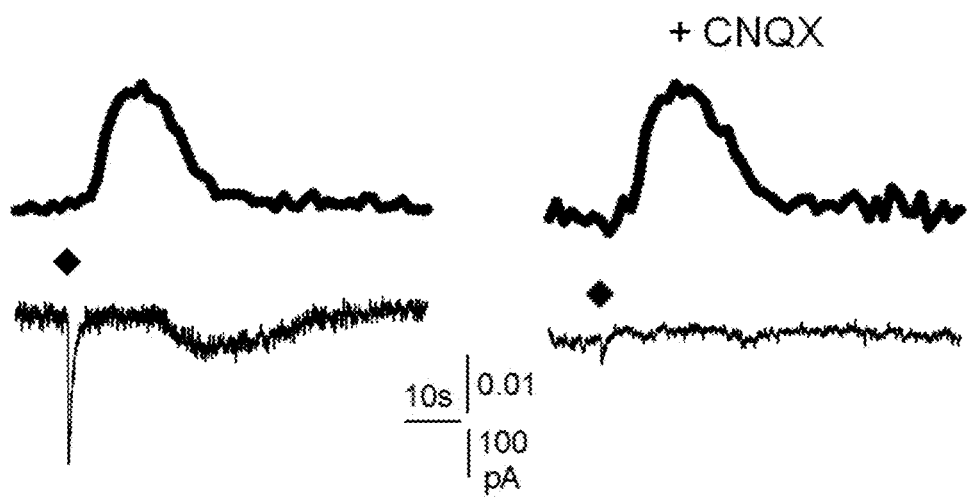
Figure 6C:
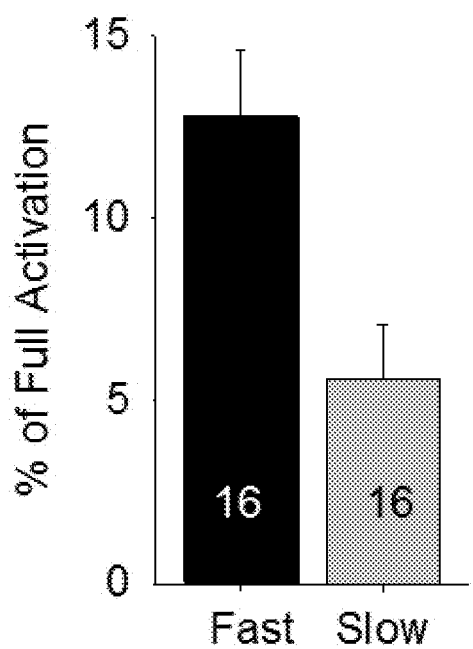
Figure 6D:
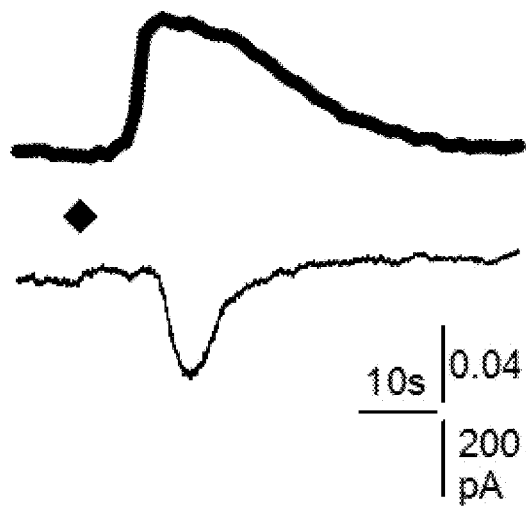
Figure 6E:
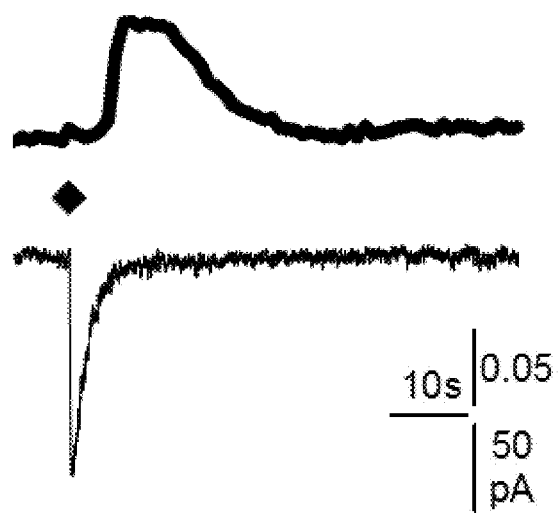
Figure 6F:
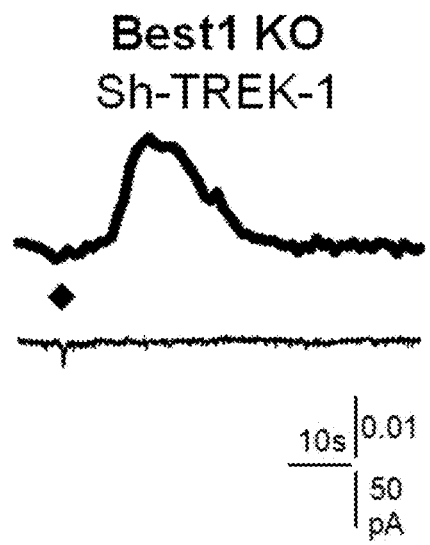

FIG. 6f is a summary graph for percentage (%) of gold particles for TREK-1 and Best1 located on the plasma membrane of cell body, process, and microdomain. (*1, p=0.0005; , p=0.008; ***2, p=0.0001) (All values are mean±s.e.m.)

Figure 6G:
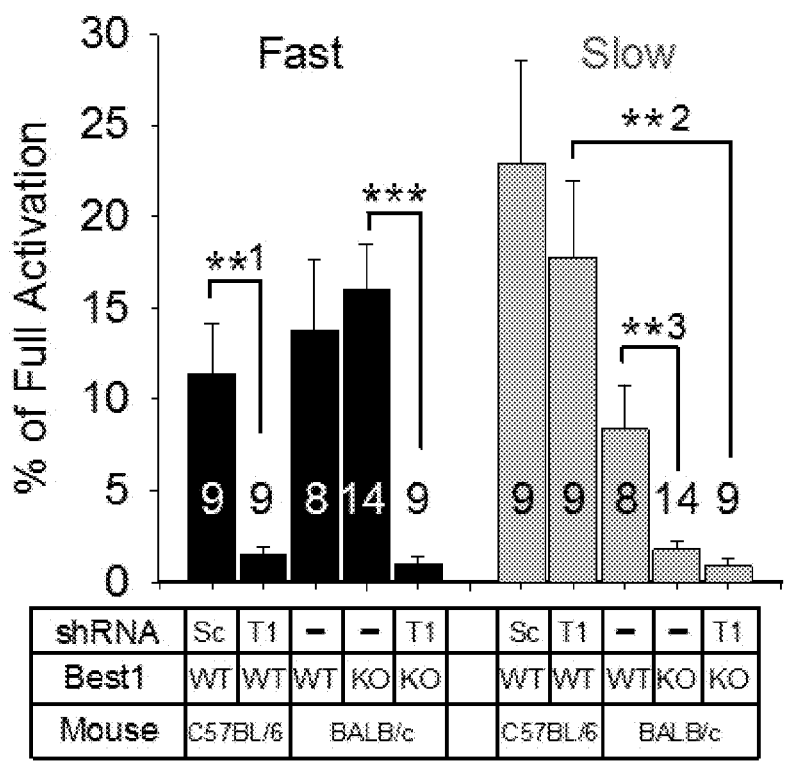

FIG. 6g shows a molecular model of the receptor-mediated glutamate release in astrocyte. Upon PAR-1 activation, dissociated $G_{\beta\gamma}$ activates TREK-1 to induce fast-mode of glutamate release, while $G_{\alpha q}$-mediated signaling and $Ca^{2+}$ induce slow-mode of Best1-mediated glutamate release.

Figure 6H:
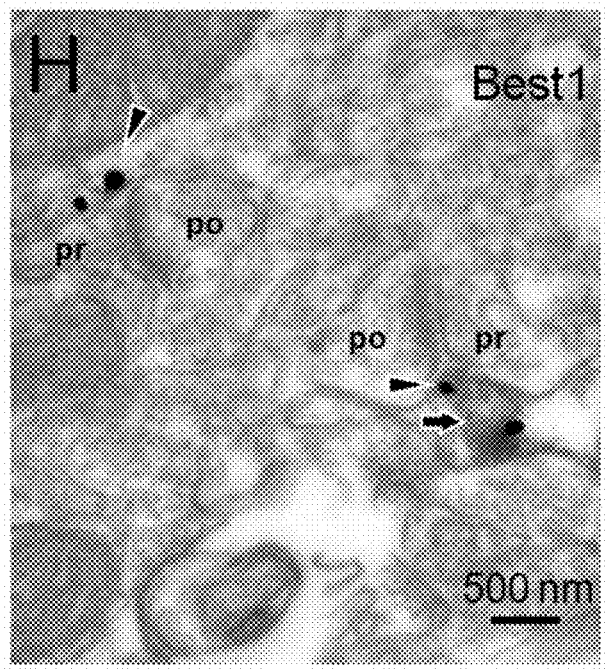
Figure 6I:
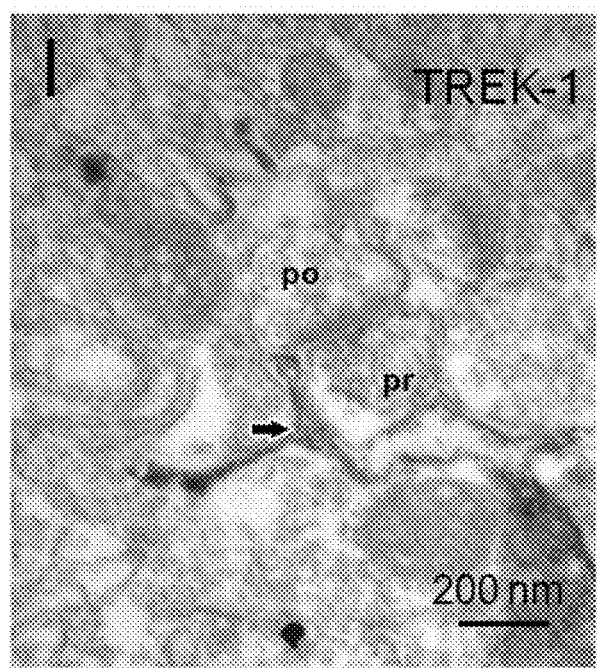

FIGS. 6h and 6i are the Electron microscopic immunostainings of Best1 (D) and TREK-1 (E) in GFAP-GFP mouse CA1 hippocampal (dark specks, arrowheads), and GFP, representing astrocyte, is stained with immunoperoxidase (dark amorphous deposits, arrows) (Pr: pre-synapse; Po: post-synapse).

Figure 6J:
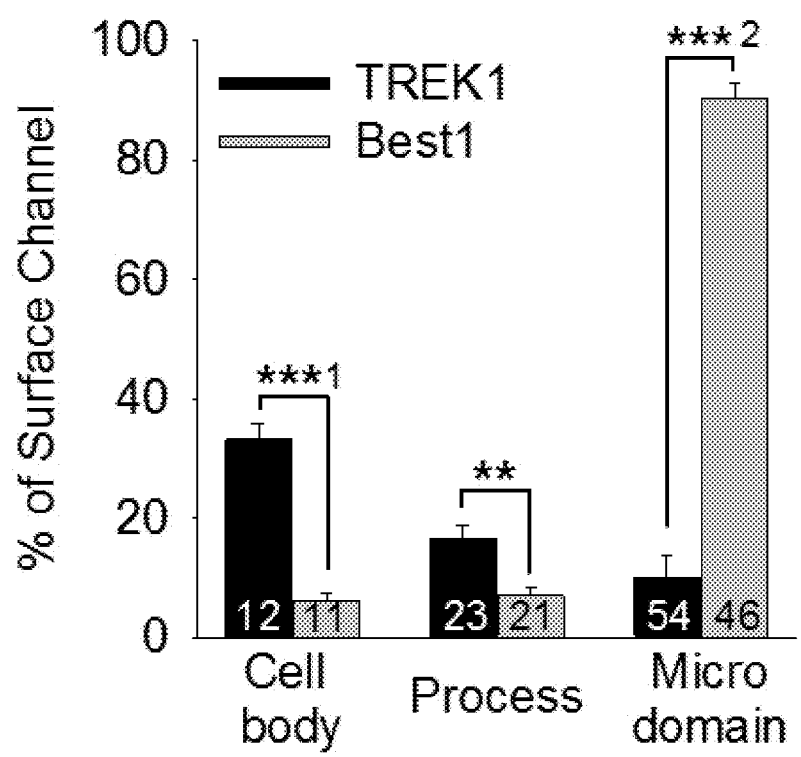

FIG. 6j shows a summary bar graph that represents the percentage of gold particle of TREK-1 and Best1 in the cell membranes of cell body, process and microdomain (*1, p=0.0005; , p=0.008; ***, p=0.0001).

Figure 6K:
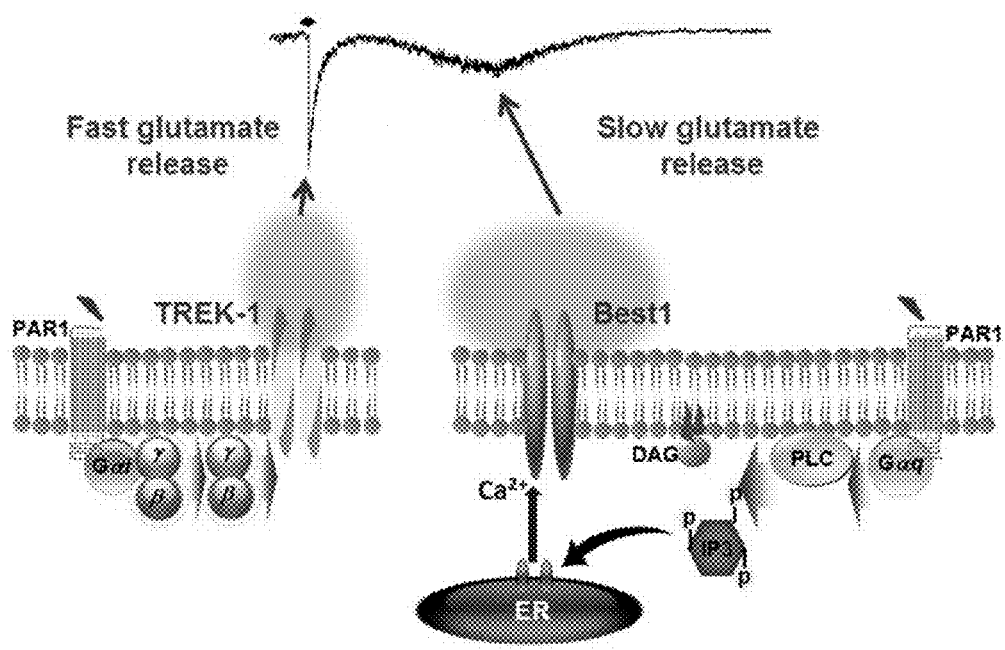

FIG. 6k shows a schematic drawing of the glutamate release mediated by the receptor in astrocyte.

FIG. 7a to FIG. 7i show the diffusion modeling predicting the concentrations of fast and slow-modes and their target neuronal receptors.

Figure 7A:
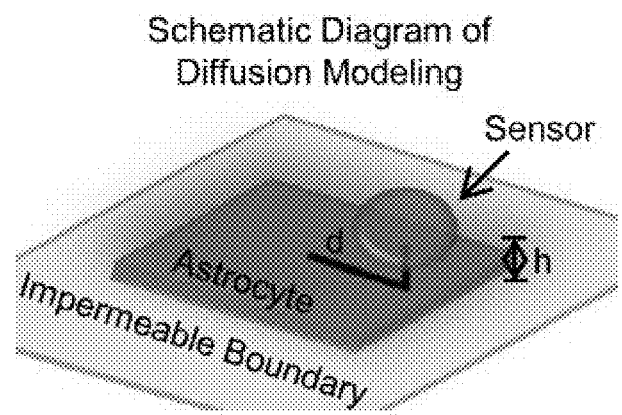

FIG. 7a is a schematic diagram of the diffusion model simulation. The geometry of a single astrocyte on an impermeable boundary is modeled by a square of 100 μM×100 μm.

Figure 7B:
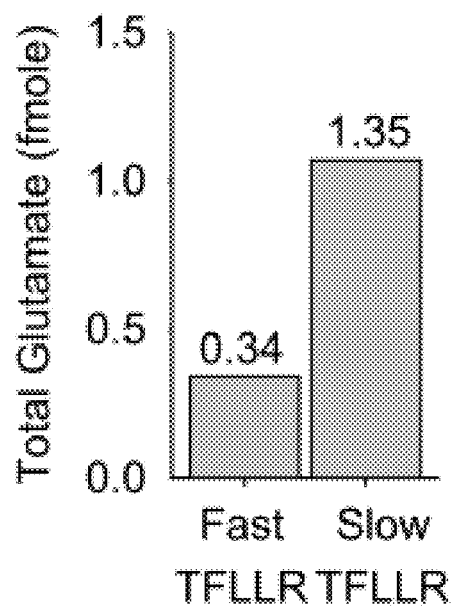

FIG. 7b shows that based on the normalized electrical responses captured by the sensor (HEK cell), the original release of glutamate from the astrocyte was estimated. According to the reconstructed release, the normalized responses are calculated. The release by TFLLR stimulation is divided by the two modes of the leading transient (fast) followed by the smooth (slow).

Figure 7C:
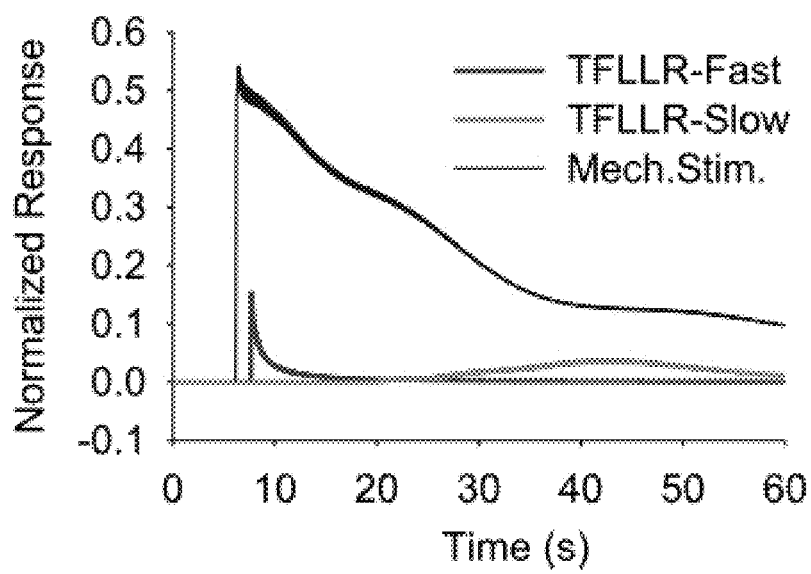

FIG. 7c represents that according to the simulation result, the fast and the slow-modes release glutamate of about 0.34 fmole and 1.35 fmole, respectively. The peak of the fast-mode is higher than that of the slow-mode, but the slow-mode continuously releases glutamate in comparison to the fast one where an instantaneous release occurs.

Figure 7D:
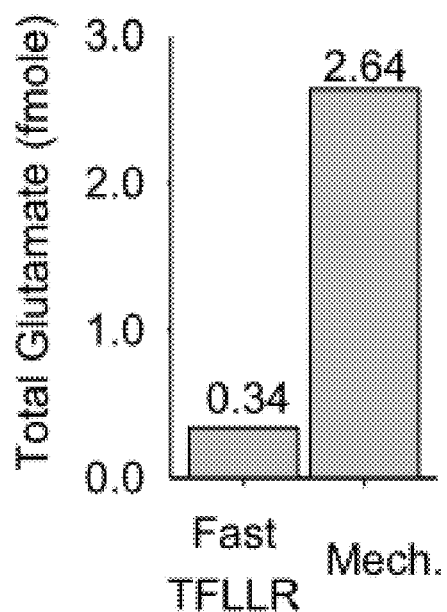

FIG. 7d represents that the mechanical stimulation induces a strong and long-term release with respect to the TFLLR stimulation. Therefore, the total amount of glutamate release is considerable. The glutamate releases at the beginning are 0.34 fmole for the fast-mode of TFLLR as in FIGS. 7c and 2.64 fmole for the mechanical stimulation.

Figure 7E:
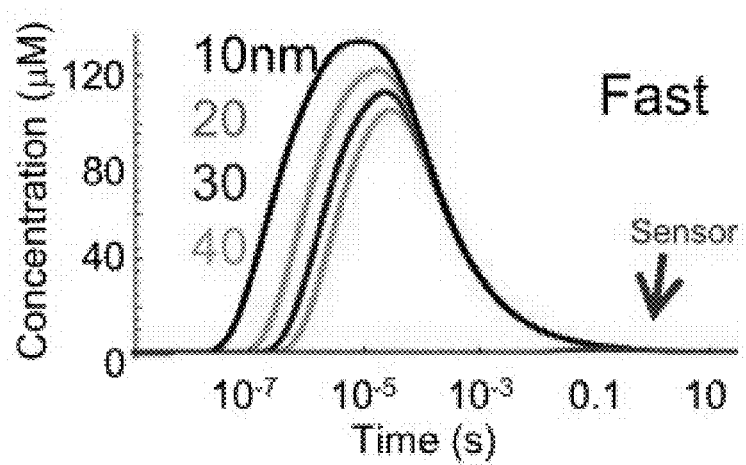
Figure 7F:
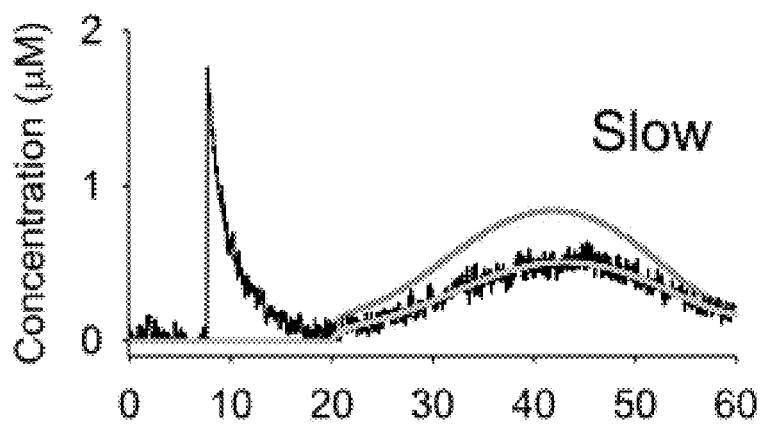
Figure 7G:
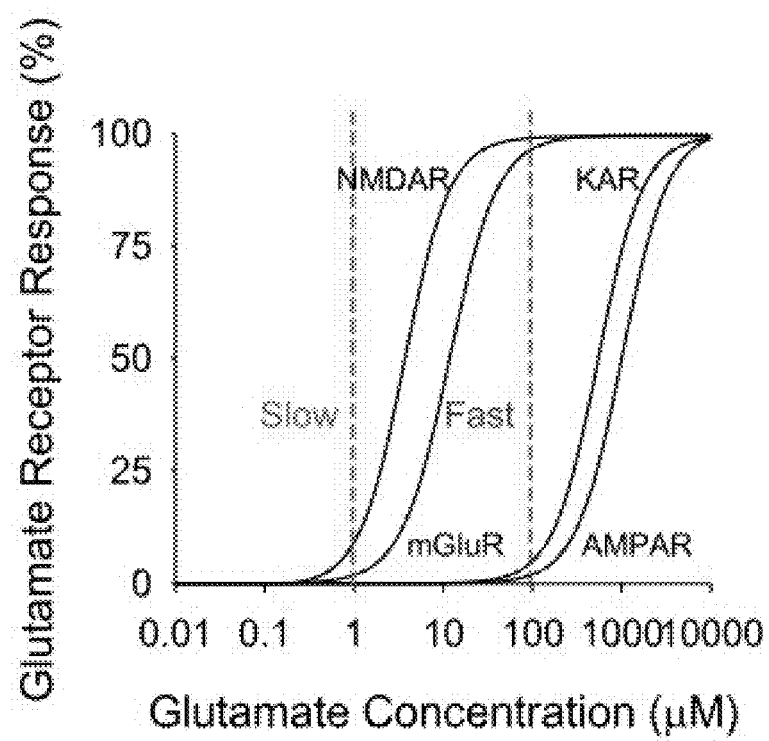
Figure 7H:
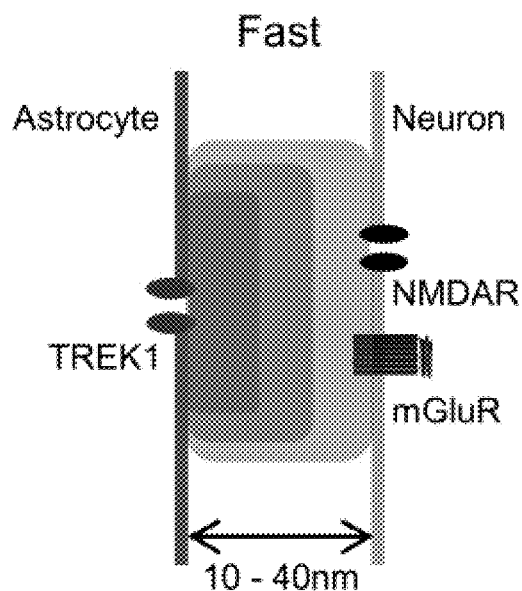

FIG. 7e represents that the glutamate concentrations of the fast-mode are estimated at positions apart from the center of the astrocyte by 10 to 40 nm as in FIG. 7h to mimic the distance between the astrocyte and the counter receptors in neighboring neuron. Their highest values are of the order of 100 μM.

FIG. 7f shows that in the case of the slow-mode, the glutamate concentrations are indistinguishable with respect to the gaps of 10 to 40 nm. The highest value is about 0.8~0.9 μM.

FIG. 7g is the result of FIG. F shows that the fast-mode is easily detectable by NMDAR and mGluR, whereas the slow-mode by only NMDAR.

FIG. 7h shows the schematic diagram of the fast-mode is shown.

Figure 7I:
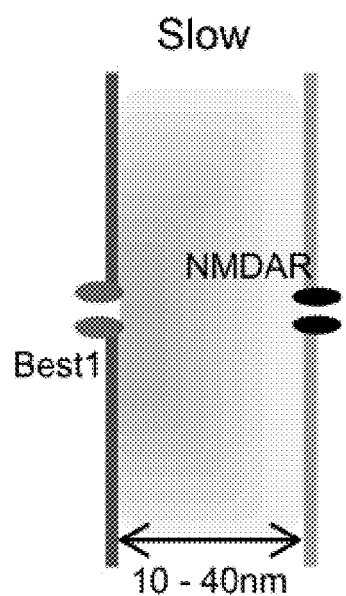

FIG. 7i shows a schematic diagram of the slow-mode is shown.

Figure 8A:
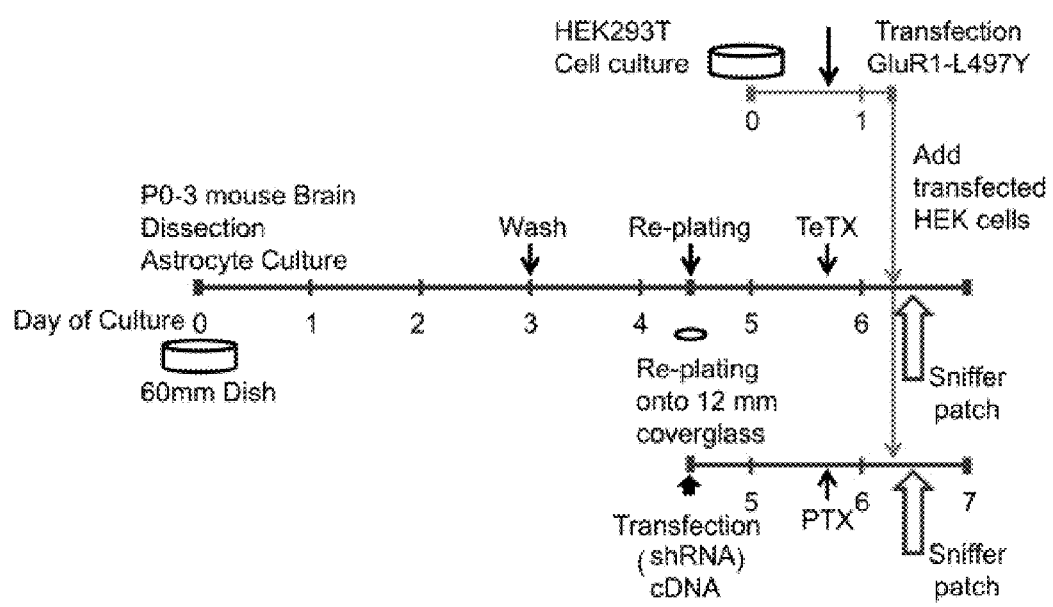
Figure 8B:
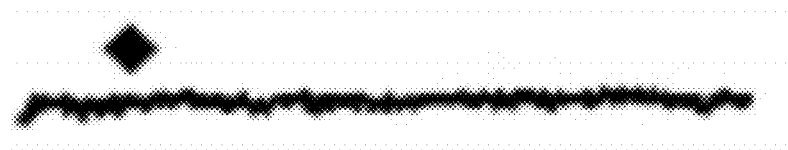
Figure 8C:
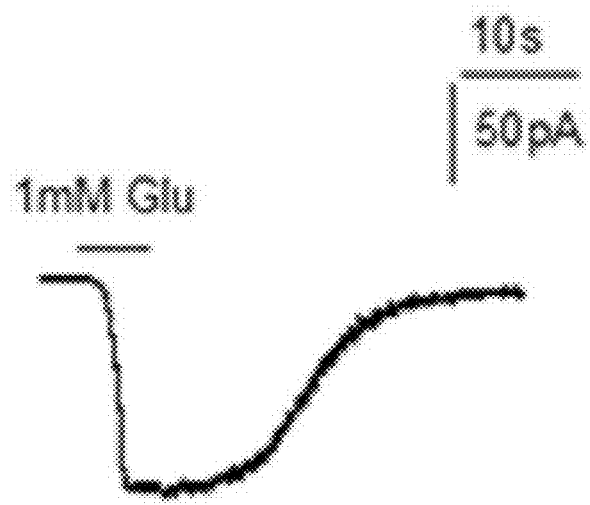
Figure 8D:
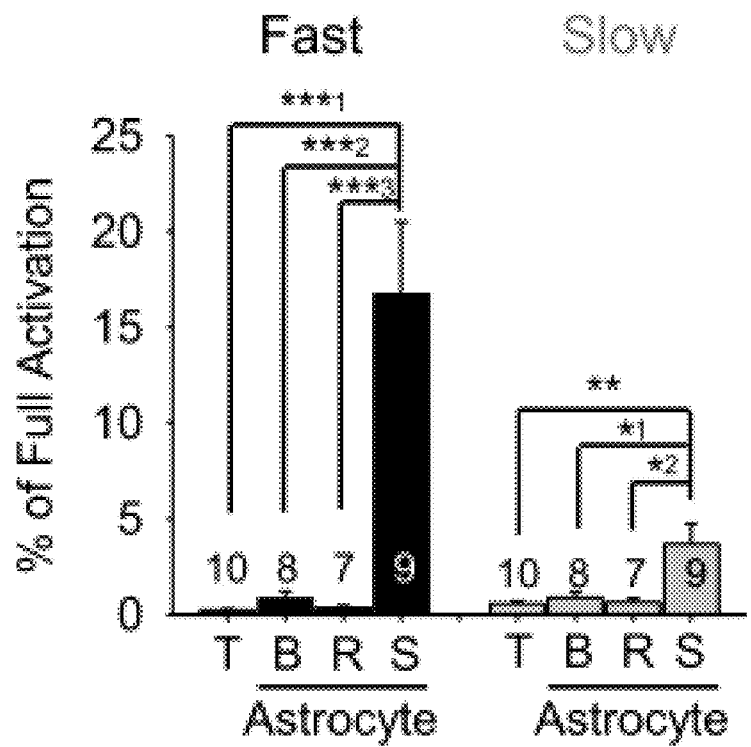
Figure 8E:
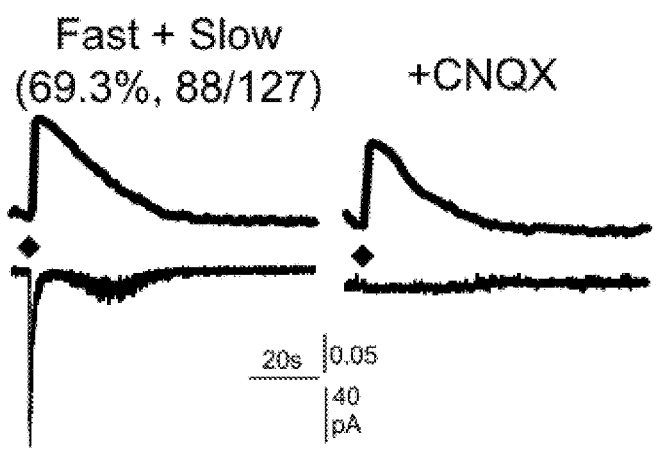
Figure 8F:
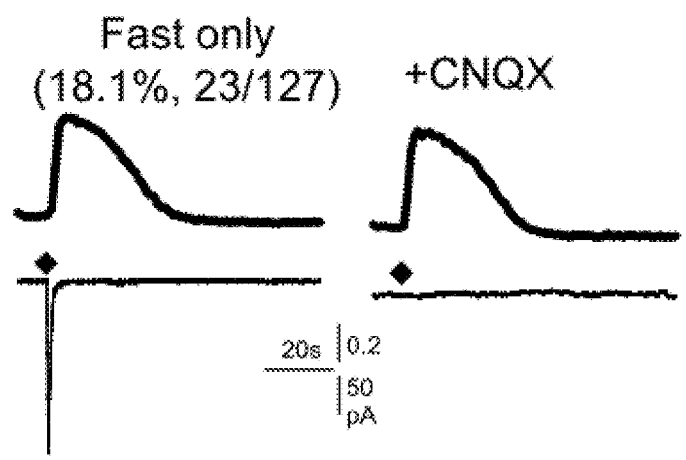
Figure 8G:
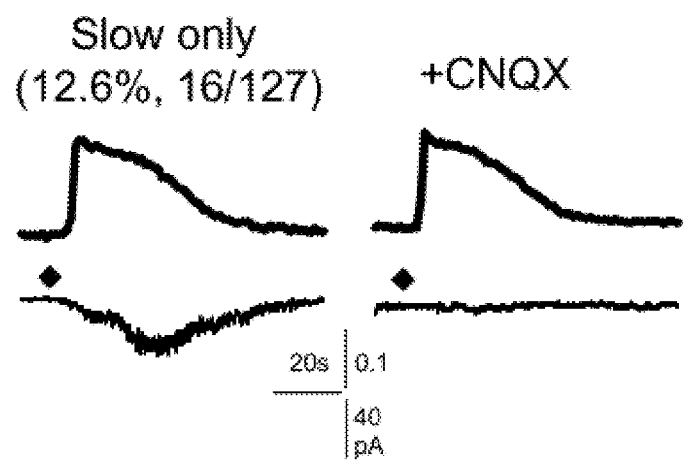
Figure 8H:
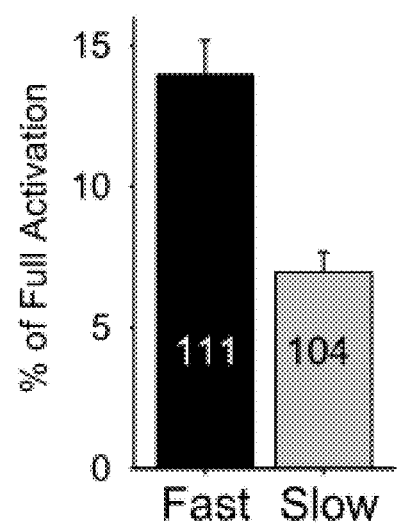
Figure 8I:
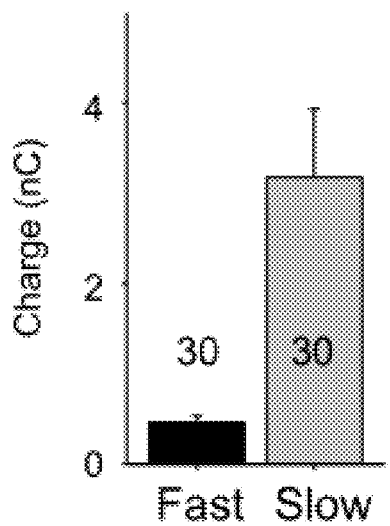
Figure 8J:
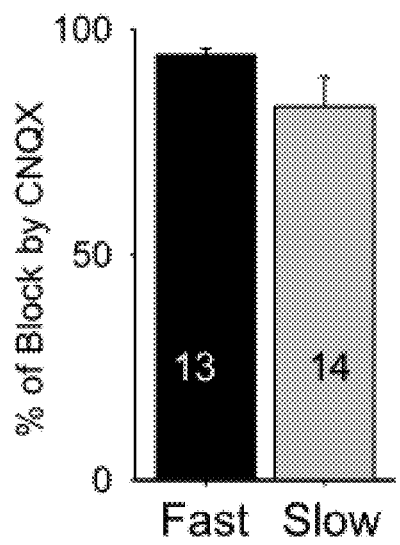
Figure 8K:
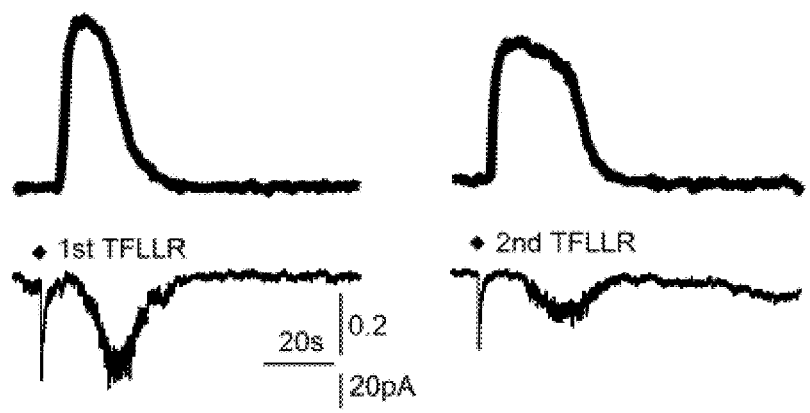
Figure 8L:
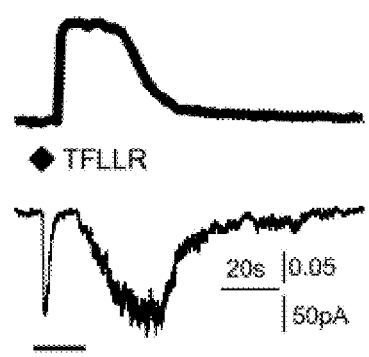
Figure 8M:
Figure 8N:
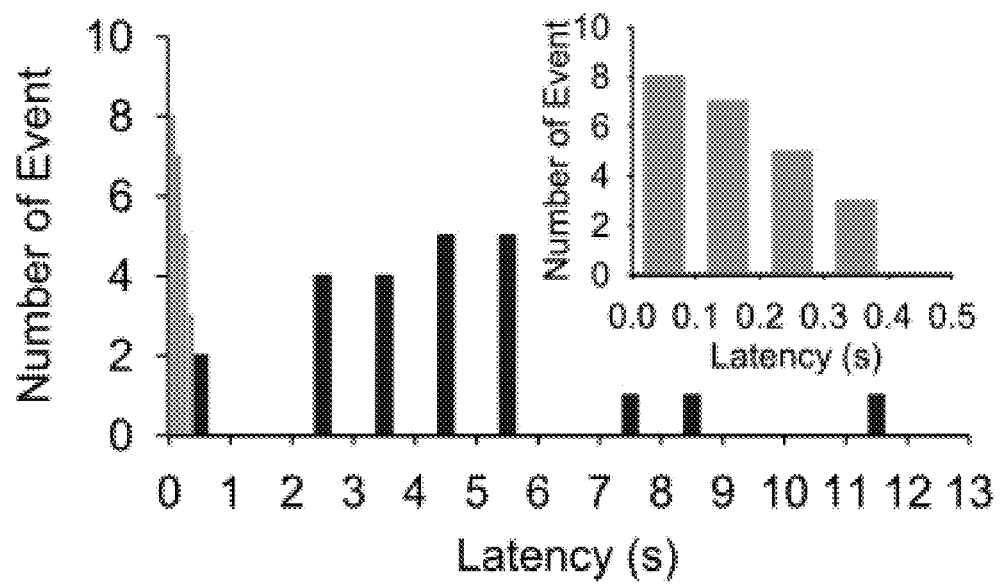
Figure 8O:
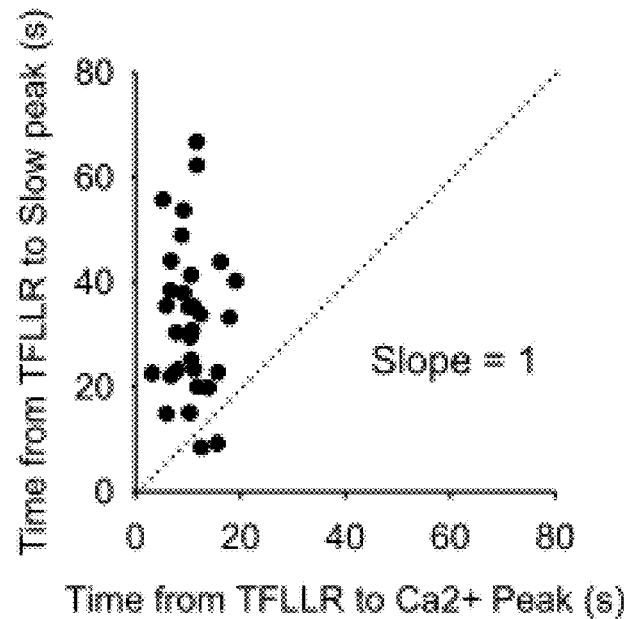
Figure 8P:
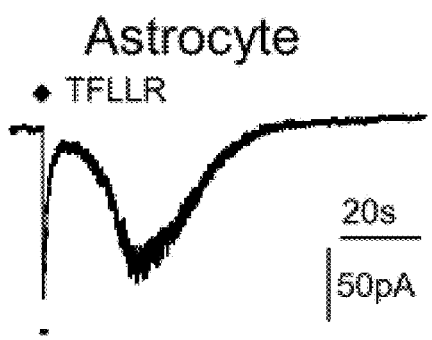
Figure 8Q:
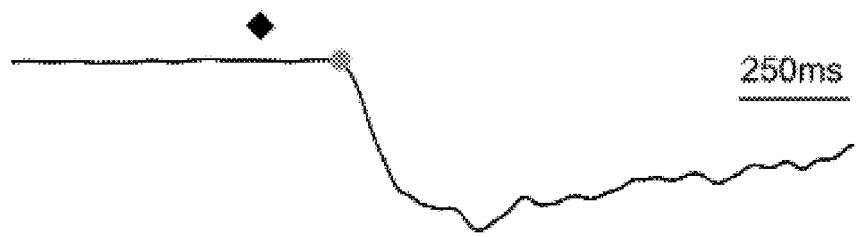
Figure 8R:
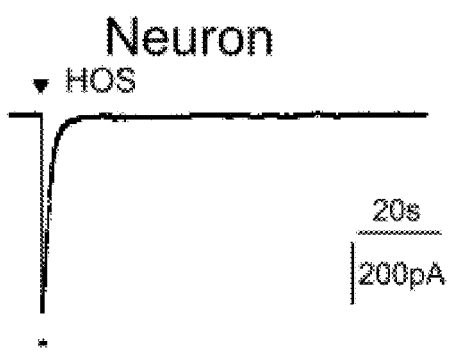
Figure 8S:
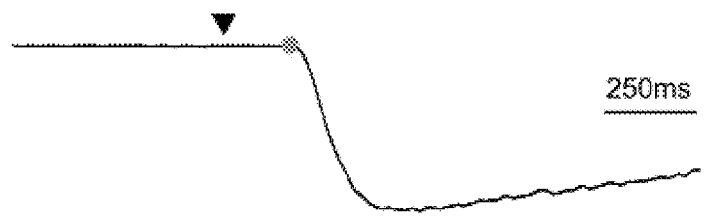
Figure 8T:
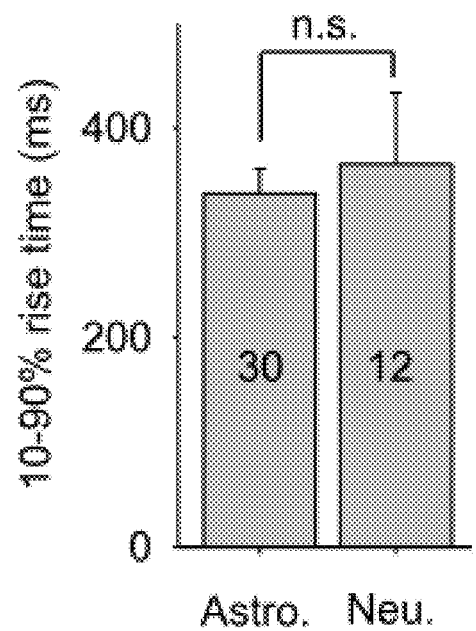
Figure 8U:
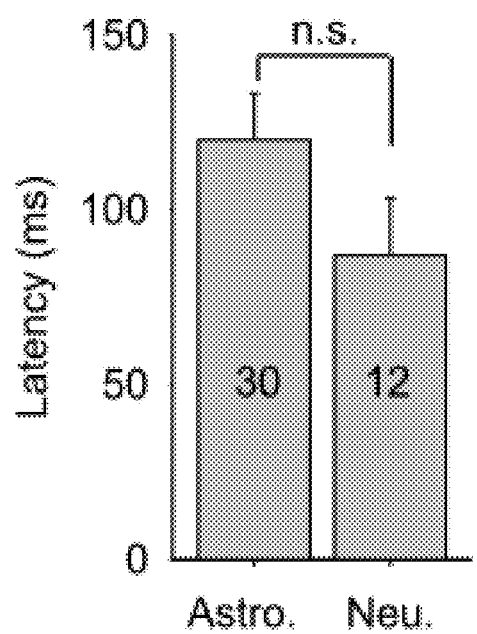

FIG. 8a to FIG. 8u represent the experimental design and the kinetics for fast and slow-modes of sniffer-patch experiment, related to FIG. 1

FIG. 8a represents a schematic diagram for the experimental procedure and timeline of the sniffer-patch. Green lines represent the manipulation of HEK cells. Green arrows show re-plating HEK cells onto naïve and transfected astrocytes. Red lines represent the manipulation of astrocytes. Arrows show the timing of various treatments.

FIG. 8b represents that the pressure-applied TFLLR does not induce any GluR1-mediated current from GluR1-L497Y expressing HEK cell without astrocyte. The diamond indicates pressure application of 500 μM TFLLR for 100 ms.

FIG. 8c represents that bath application of 1 mM glutamate on HEK cell expressing GluR1 induces full activation of GluR1-L497Y expressed in HEK cell.

FIG. 8d is a summary graph which shows the significant difference between with and without astrocyte on % of glutamate evoked-current of fast and slow glutamate release. Values are mean±s.e.m (*, p=0.001; , p=0.008).

FIG. 8e shows the representative traces that shows both fast and slow-modes modes (left) which are blocked by 10 μM CNQX (right), an AMPA receptor blocker.

FIG. 8f shows the representative traces showing additional fast-mode modes (left) which are blocked by 10 μM CNQX (right).

FIG. 8g shows a representative traces showing additional slow-mode modes (left) which are blocked by 10 μM CNQX (right).

FIG. 8h shows a summary for % of full activation {(peak amplitude of TFLLR-induced current/full activation current)×100}.

FIG. 8i shows a summary for charge transfer (area under the curve) for fast and slow-modes.

FIG. 8j shows a summary for percent of CNQX block. All error bars in this study indicate standard error of the mean (FIG. 8g-FIG. 8i). Number on each bar indicates number of cells for each condition.

FIG. 8k represents the repeated pressure-applications of TFLLR show repeated responses of fast and slow-mode in the same astrocyte. The two applications are separated by 10 min recovery time.

FIG. 8l to FIG. 8m represent the extended traces in M are derived from the duration of horizontal bar in L. The onset of TFLLR-induced fast-mode (green dot) occurs before that of $Ca^{2+}$ transient (blue dot). The latency is time from diamond to green or blue dot.

FIG. 8n is a summary graph shows frequency histogram of latencies binned by 100 ms for the latency of fast-mode and by 1 s for the latency of $Ca^{2+}$ response. The latencies of $Ca^{2+}$ and the onset of fast-mode are completely separated. The inset shows the extended graph of the histogram for onset of the fast-mode.

FIG. 8o is a scatter plot of time from TFLLR to peak of $Ca^{2+}$ response versus the peak time of the slow-mode release (time from TFLLR to $Ca^{2+}$ peak: 10.8±0.7 s (n=31), time from TFLLR to slow peak: 32.8±2.6 s (n=31)).

FIG. 8p to FIG. 8s represent the kinetics of fast-mode release from an astrocyte and neuronal vesicular release were compared.

FIG. 8p represents a representative trace showing latency from TFLLR to onset of fast-mode in astrocyte.

FIG. 8q represents the current trace extended by the duration of the horizontal bar in P.

FIG. 8r represents a representative trace showing latency from hyperosmotic solution (HOS, 512 mOsm, balanced with sucrose) application to the onset of (HOS)-induced current in neuronal culture. The reverse triangle indicates the pressure-application of HOS for 100 ms.

FIG. 8s represents the current trace extended from the duration of the horizontal bar in R.

FIG. 8t is a summary graph for 10-90% rise time. Values are mean±s.e.m (n.s., non-significance).

FIG. 8u is a summary graph for latency from pressure application to onset of the current. Values are mean±s.e.m (n.s., non-significance).

FIG. 9a to FIG. 9k show the effects of molecular G protein inhibitors on Ca2+ imaging and $G_{\alpha i}$ activations, but not $G_{\alpha s}$, induce fast-mode.

Figure 9A:
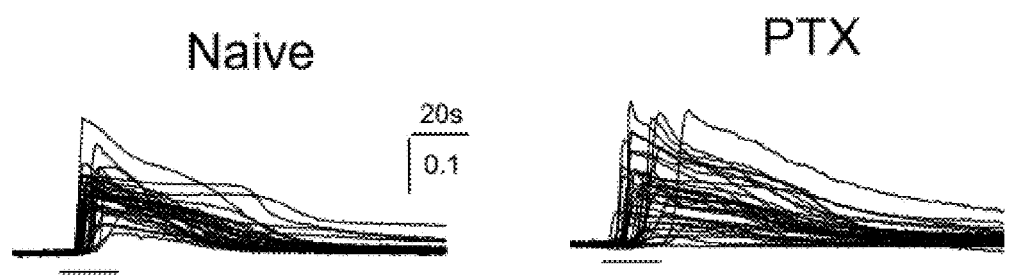

FIG. 9a shows that PTX does not inhibit TFLLR-induced $Ca^{2+}$ transients.

Figure 9B:
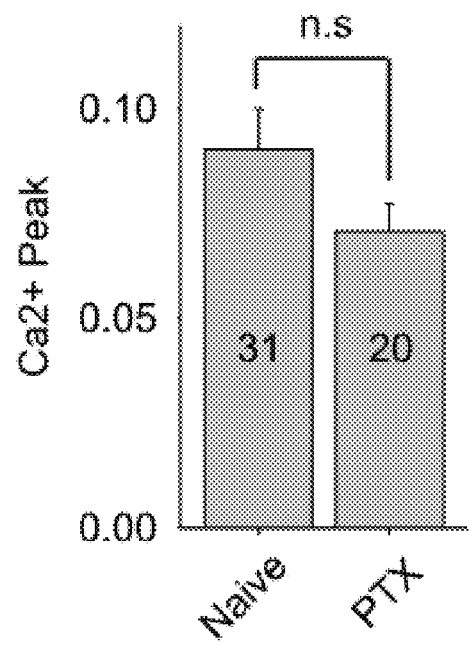

FIG. 9b is a summary graph showing $Ca^{2+}$ peak between Naïve and PTX treatment FIG. 9c shows that Phosducin C-terminal fragment and β-ARK-c term do not inhibit TFLLR-induced $Ca^{2+}$ transient.

Figure 9D:
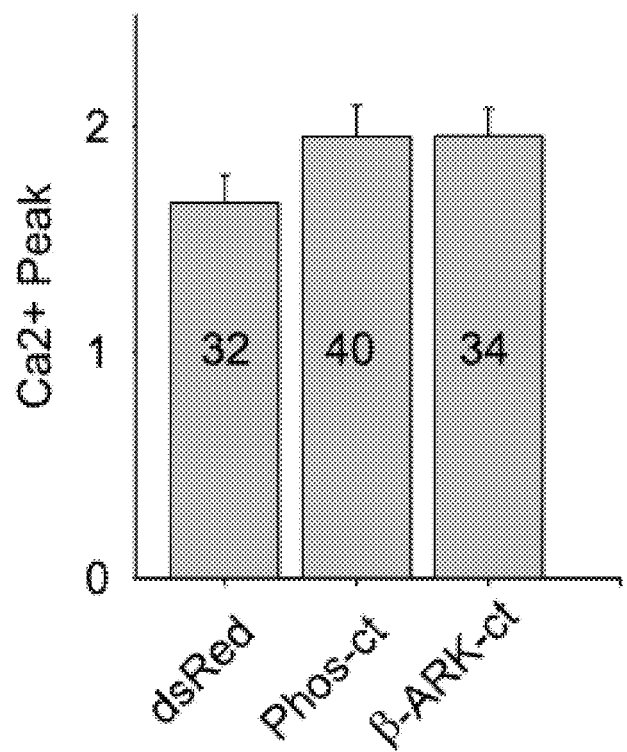

FIG. 9d is a summary graph shows no significance among three groups.

Figure 9E:
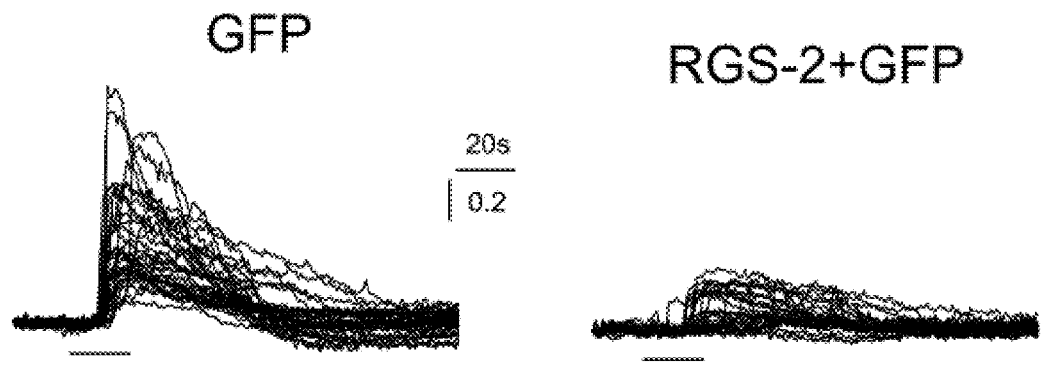

FIG. 9e shows that TFLLR-induced $Ca^{2+}$ transients are greatly and significantly reduced in astrocytes expressing RGS-2 and GFP compared with astrocytes expressing only GFP.

Figure 9F:
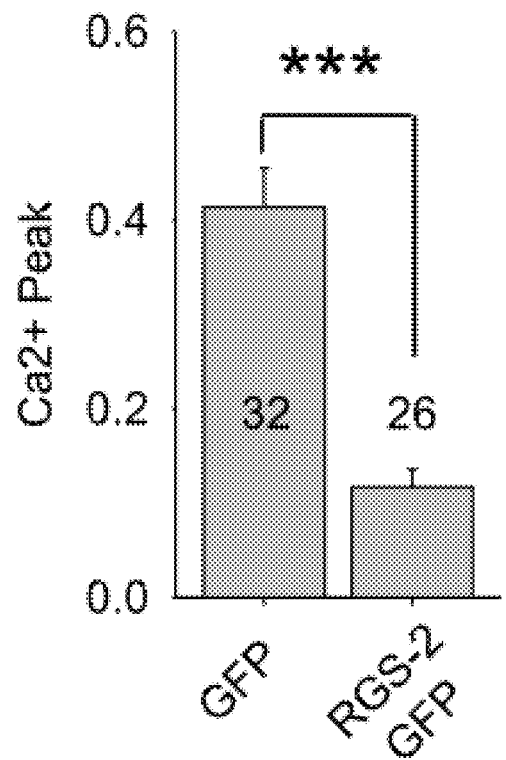

FIG. 9f Summary graph shows significant difference on the peak of $Ca^{2+}$ transient between astrocytes expressing GFP and RGS-2+GFP. Values are mean±s.e.m (***, p<0.00003).

Figure 9G:
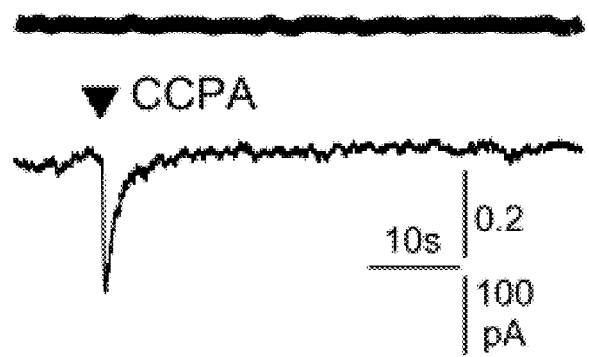

FIG. 9g represents that traces show $Ca^{2+}$ (upper) and GluR1-mediated current (lower) at −70 mV of holding potential ($V_h$=−70 mV). The pressure-applied CCPA for A1R activation induces mainly fast GluR1-mediated inward current, whereas does not induce $Ca^{2+}$ transient. The reverse triangle indicates 1 μM CCPA for 100 ms.

Figure 9H:
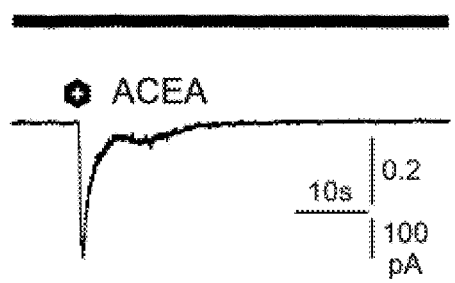

FIG. 9h represents that the pressure-applied ACEA for CB1R activation induces mainly fast-mode. The black hexagon indicates 300 μM ACEA for 100 ms.

Figure 9I:
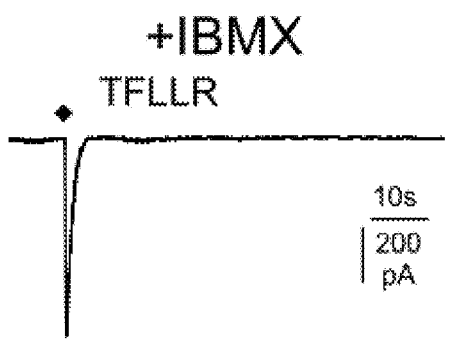
Figure 9J:
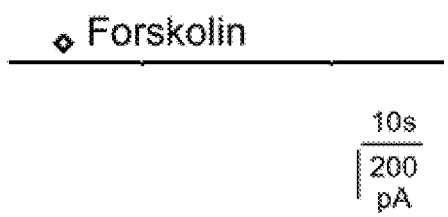
Figure 9K:
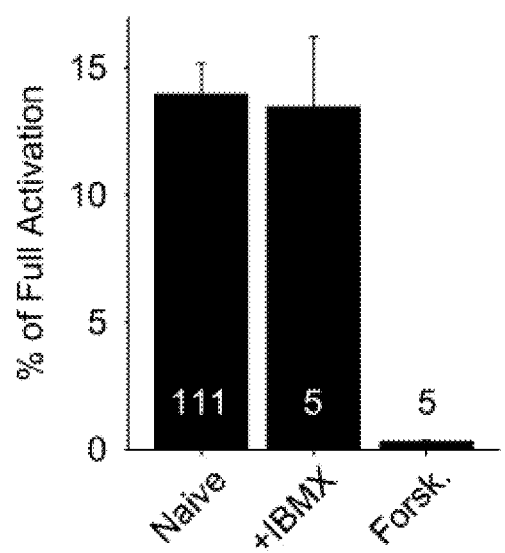

FIG. 9i to FIG. 9k represent that the change of cAMP concentration is not involved in fast-mode release, FIG. 9i Incubation with 100 μM 3-isobutyl-1-methylxanthine (IBMX), an inhibitor for phosphodiesterase (PDE) does not affect TFLLR-induced fast-mode, FIG. 9j The pressure-application of forskolin, an activator of adenylyl cyclase, does not induce fast-mode. The diamond with white diamond indicates 300 μM forskolin for 100 ms, FIG. 9k Summary bar graph on fast-mode.

Figure 10A:
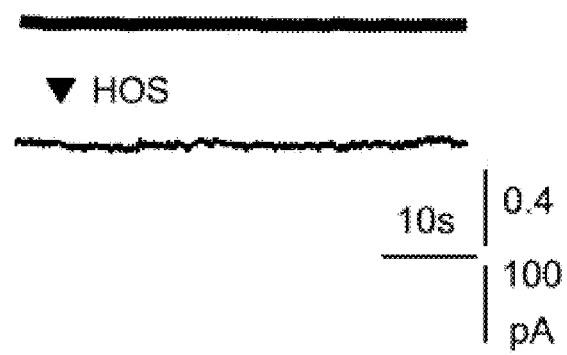
Figure 10B:
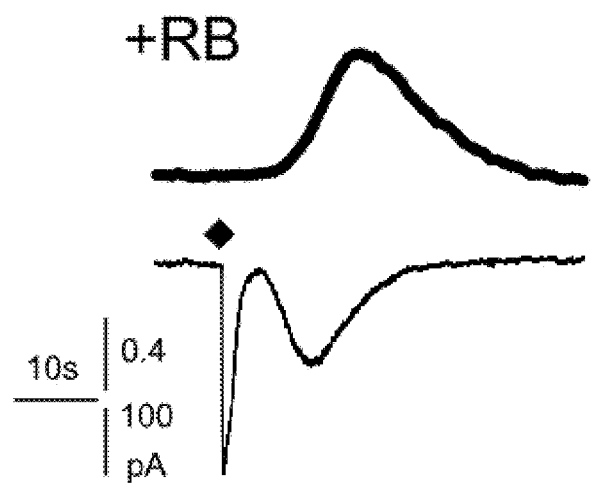
Figure 10C:
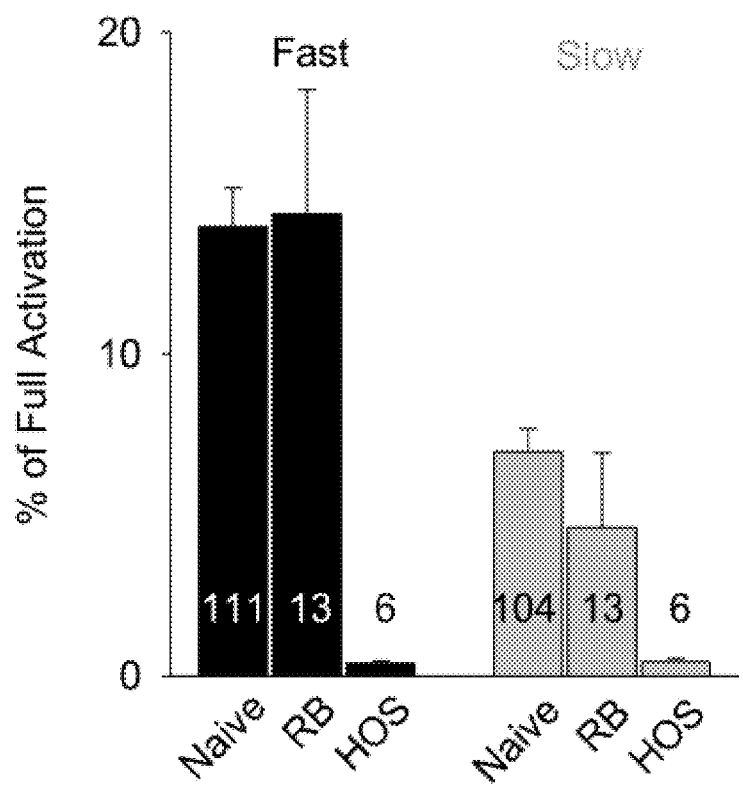

FIG. 10a to FIG. 10c represent that hyperosmotic solution (HOS) does not induce glutamate release and Rose Bengal (RB) does not inhibit TFLLR-induced GluR1LY current, FIG. 10a Pressure application of HOS (510 mOsm, 100 ms), does not induce any GluR1LY-meidated current and $Ca^{2+}$ transient from astrocyte (FIG. 10b). The treatment of RB (1 μM, pre-incubation for 30 min) does not inhibit TFLLR-induced GluR1LY-mediated current. FIG. 10c Summary bar graph.

Figure 10D:
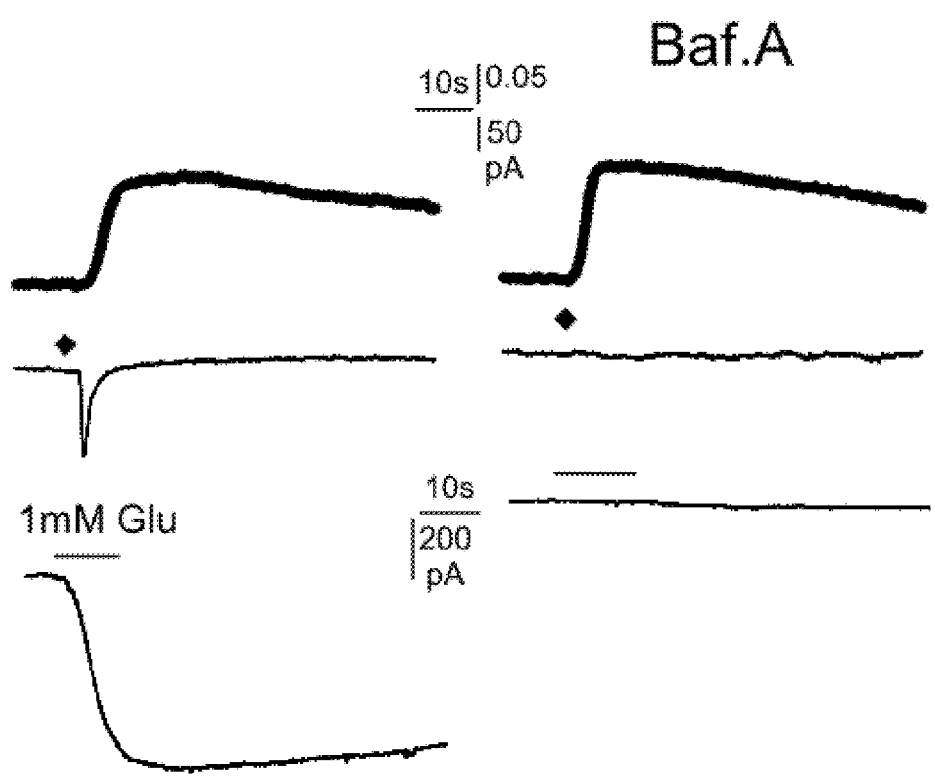

FIG. 10d to FIG. 10k represent that the various blockers of vesicular release reduce GluR1L497Y-mediated current and $Ca^{2+}$ influx, FIG. 10d In the same astrocyte, 5 μM Bafilomycin A1 (Baf.A), an inhibitor for H+-ATPase, pretreated for 30 min shows not only a significantly reduction of TFLLR-induced current (A, right middle), but also a marked reduction of (a, right lower) 1 mM glutamate-induced full activation current of GluR1LY.

Figure 10E:
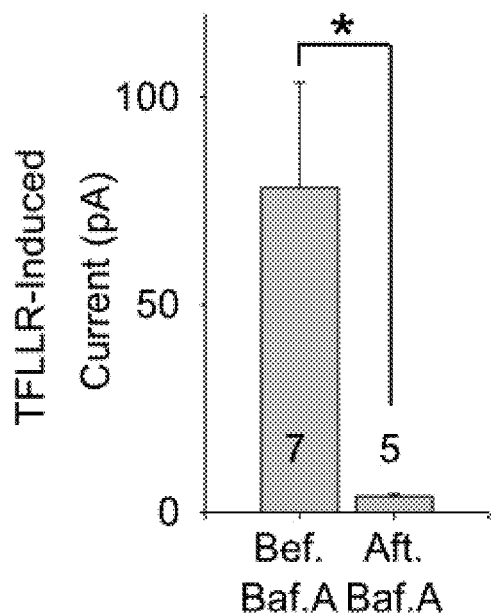

FIG. 10e Summary graph shows significantly reduced TFLLR-induced current in Baf.A treatment. Values are mean±s.e.m (*, p=0.03).

Figure 10F:
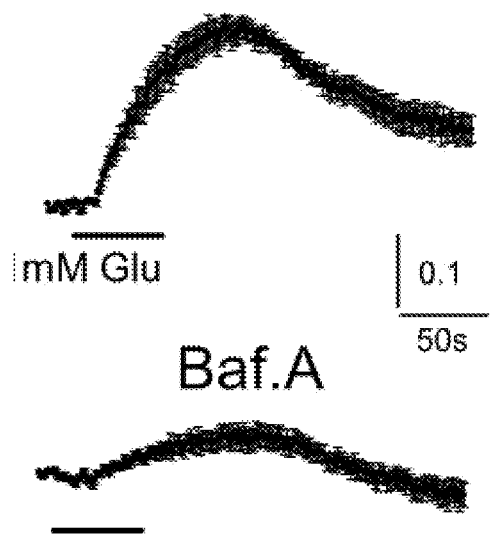

FIG. 10f represents that In HEK cells, Baf.A treatment reduces GluR1LY-mediated $Ca^{2+}$ transient evoked by 1 mM glutamate (right) compared with that of before Baf.A treatment (left).

Figure 10G:
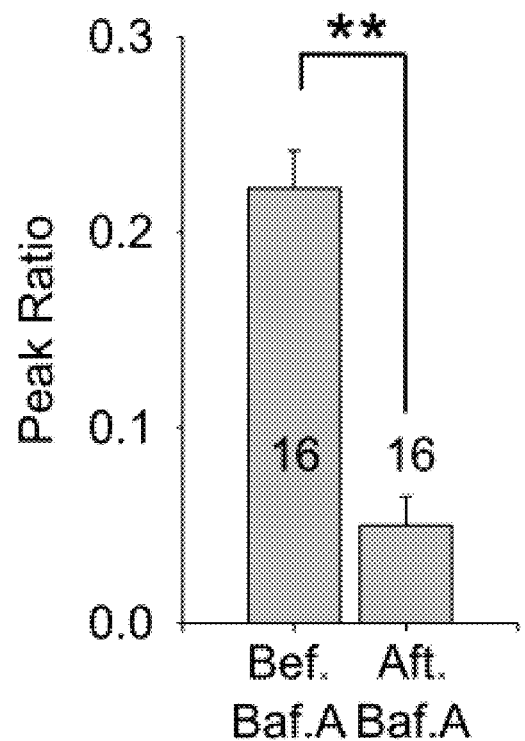
Figure 10H:
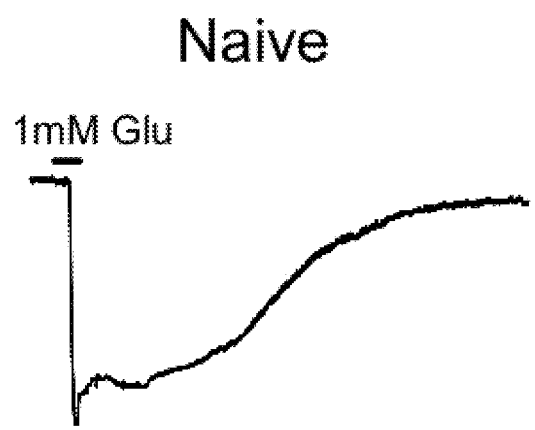
Figures 10I, 10J:
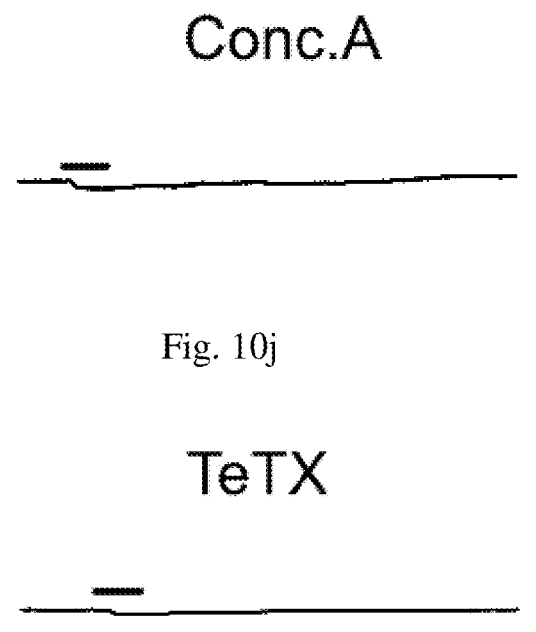

FIG. 10g is a summary graph for the effect of Baf.A treatment on GluR1LY-mediated $Ca^{2+}$ transients. Values are mean±s.e.m (**, p=0.008).

FIG. 10h to FIG. 10k shows Concanamycin A (Conc.A, a blocker for H+-ATPase) incubated for 1 hr (FIG. 10i), and 4 □M tetanus toxin (TeTX, a blocker for vesicle fusion by cleaving synaptobrevin) incubated for 16 hrs (FIG. 10j) reduced 1 mM glutamate-induced GluR1LY-mediated currents; Concanamycin A (Conc.A, a blocker for H+-ATPase) incubated for 1 hr (FIG. 10h), and 4 □M tetanus toxin (TeTX, a blocker for vesicle fusion by cleaving synaptobrevin) incubated for 16 hrs (FIG. 10j) reduced 1 mM glutamate-induced GluR1LY-mediated currents.

Figure 10K:
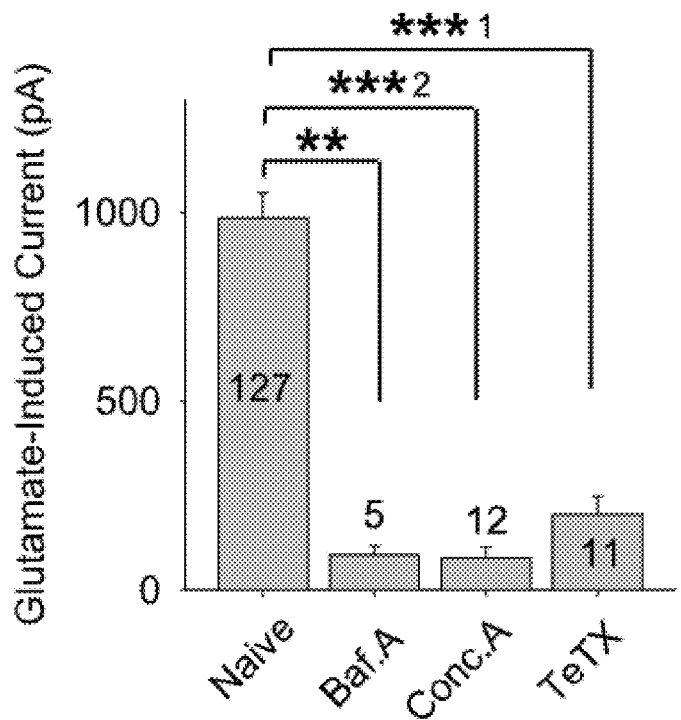

FIG. 10k is a summary graph for the effect of various blockers of vesicular release on currents. Values are mean±s.e.m (*1, p=0.0004;*2, p=0.0006, **, p=0.008). TeTX injection to a single astrocyte reduces GluR1-L497Y-mediated current.

Figure 10L:
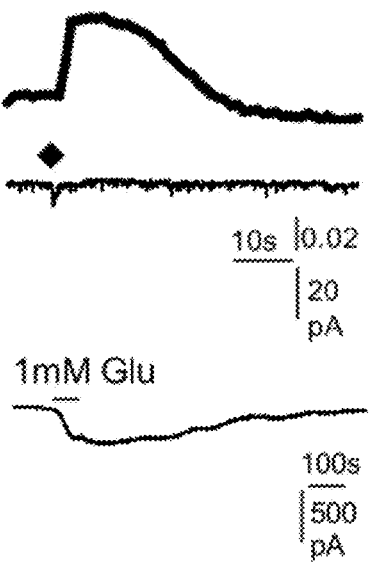
Figure 10M:
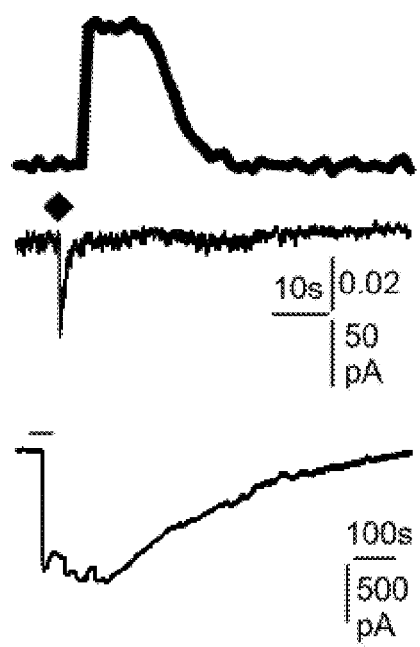
Figure 10N:
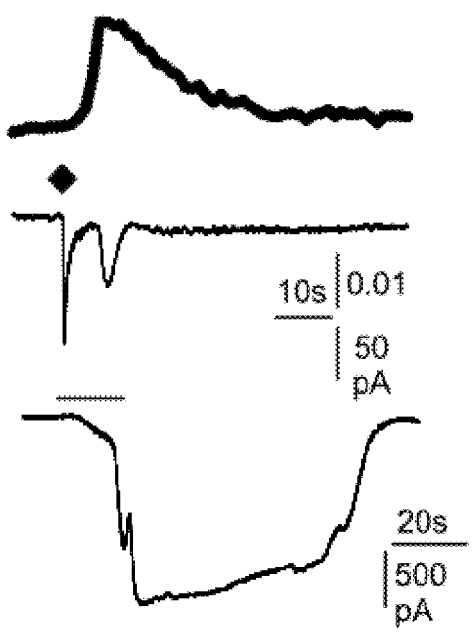

FIG. 10l to 10n show the representative data for astrocytic $Ca^{2+}$ transient and TFLLR-induced glutamate release from TeTX-loaded- (FIG. 10l), BoToxB-loaded- (FIG. 10m), and BSA loaded-single astrocyte (FIG. 10n).

FIG. 10l shows the injection of 4 μg/ml TeTX (injection time: 20 min after rupture) to a single astrocyte apparently reduce TFLLR-induced glutamate release current, and FIG. 10l (right panel) represents that TeTX injections to astrocyte also markedly reduce GluR1-L497Y-mediated current evoked by 1 mM glutamate.

FIG. 10m and FIG. 10n shows the injections of 8 μg/ml BoToxB (FIG. 10m) and BSA (FIG. 10n) as control do not affect TFLLR-induced glutamate release. The diamond indicates 500 μM TFLLR for 100 ms.

Figure 10O:
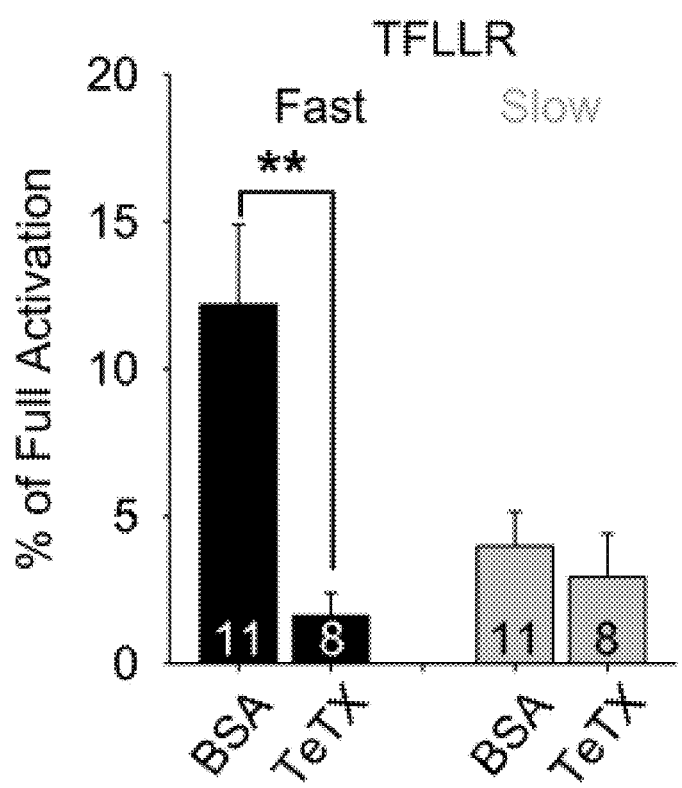

FIG. 10o is a summary graph shows that TeTX injections reduce the fast mode. Values are mean±s.e.m (**, p=0.006).

Figure 10P:
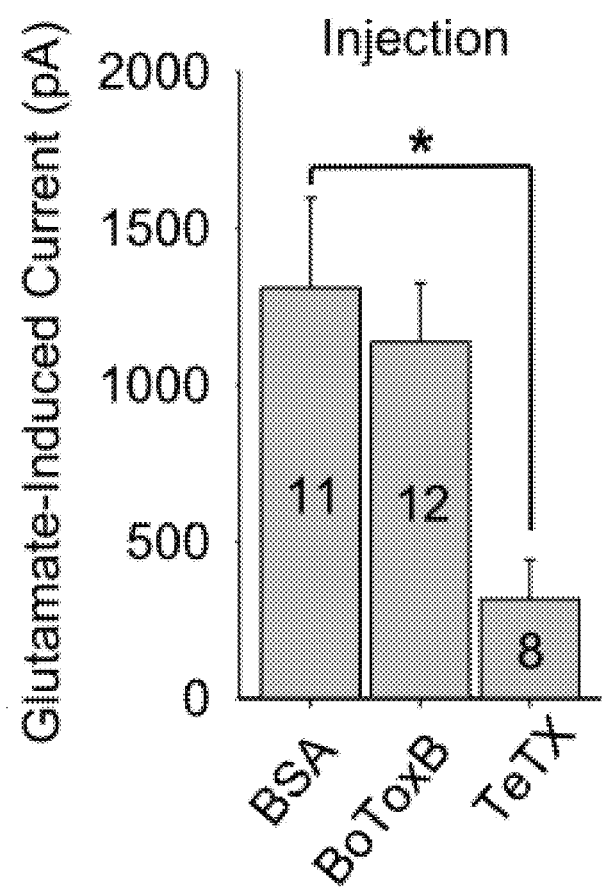

FIG. 10p is a summary graph showing TeTX injection-mediated inhibition on GluR1-L497Y-mediated current evoked by 1 mM glutamate (* indicates p<0.05).

Figure 11A:
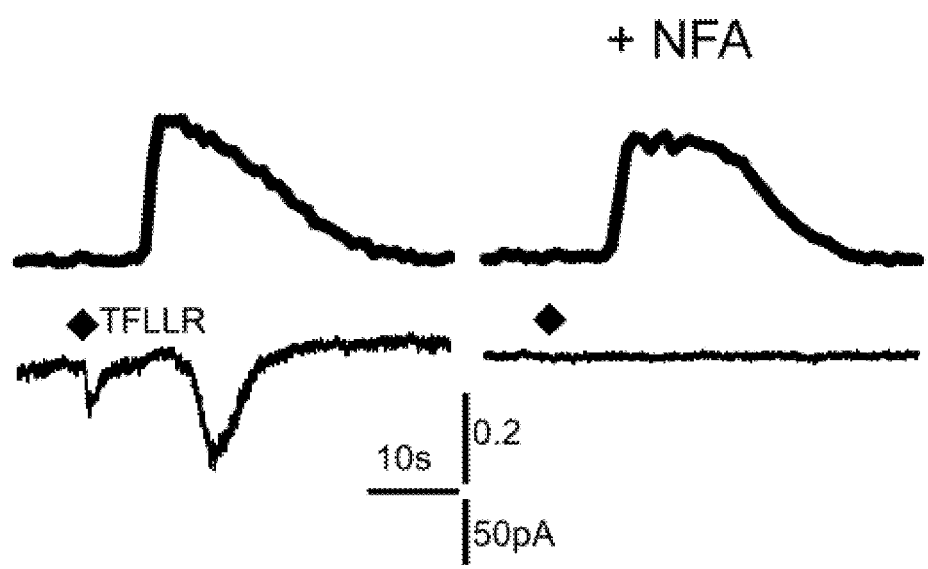
Figure 11B:
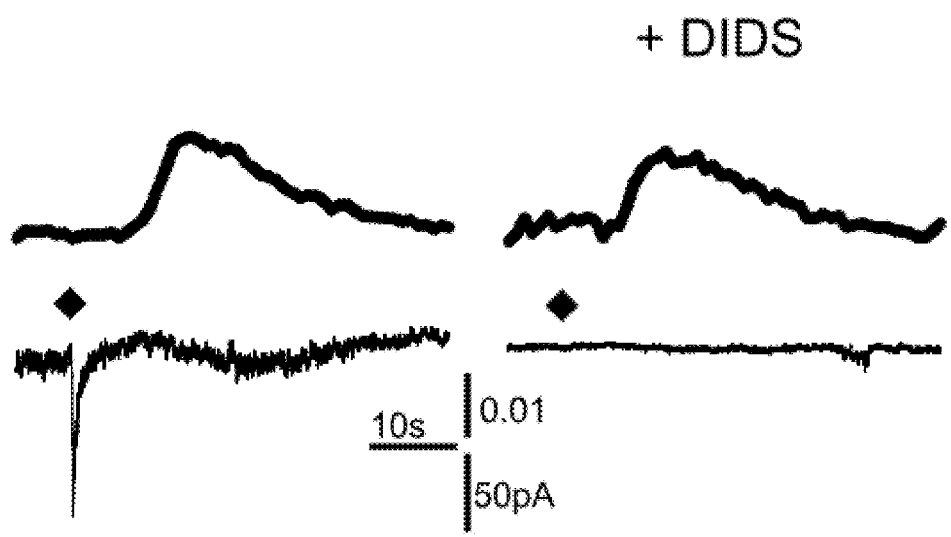
Figure 11C:
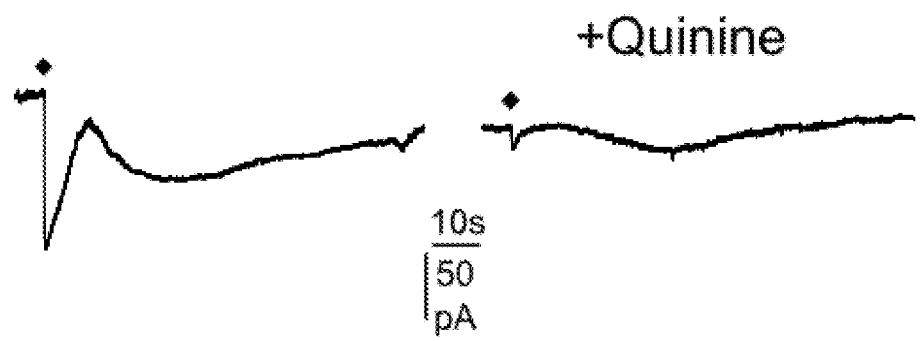

FIG. 11a to FIG. 11c show that various channel blockers reduce TFLLR-induced glutamate release. In the same astrocyte, anion channel blockers, 50 □M niflumic acid (NFA) (FIG. 11a), and 50 □M DIDS (FIG. 11b), and a K2P channel blocker, 100 □M Quinine (FIG. 11c) inhibit TFLLR-induced GluR1 L497Y-mediated current.

Figure 11D:
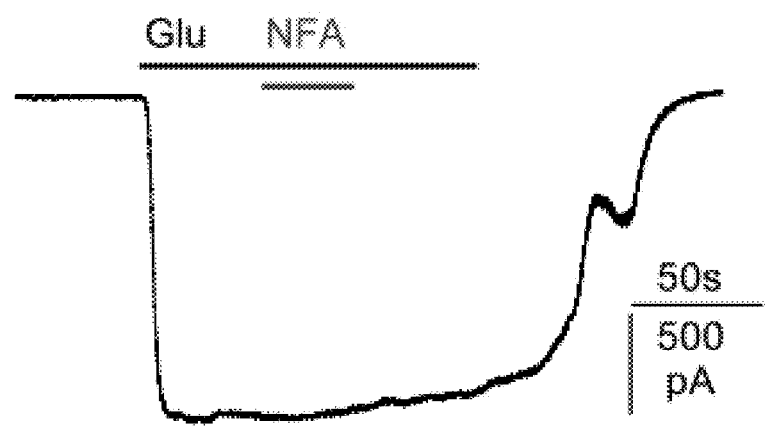
Figure 11E:
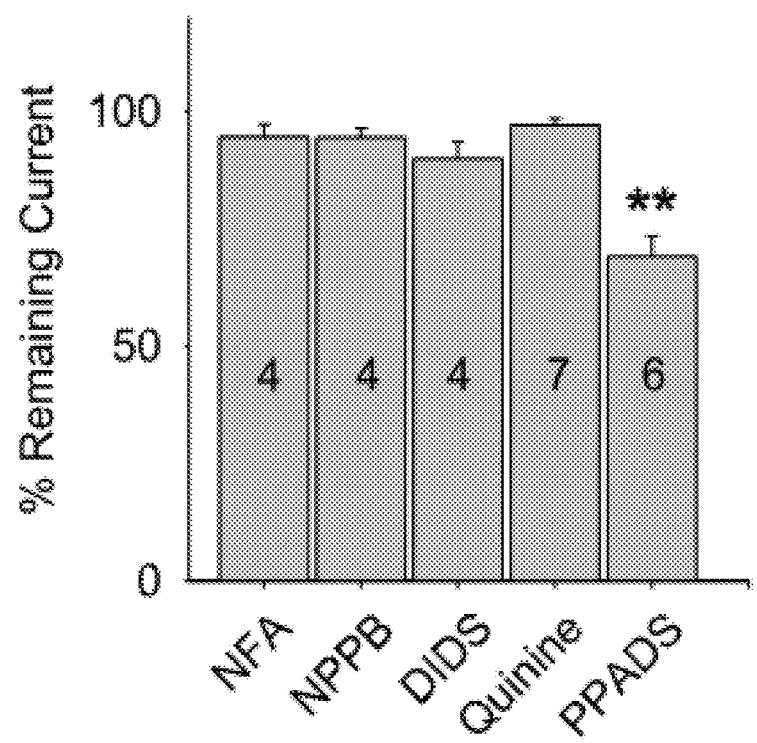

FIG. 11d and FIG. 11e Anion channel blockers do not affect GluR1L497Y, whereas PPADS shows a non-specific effect on GluR1L497Y: FIG. 11d 50□M shows that niflumic acid (NFA) does not affect 1 mM glutamate-induced current (Vh=−70 mV) recorded from FMK cell expressing GluR1L497Y, and FIG. 11e is a summary graph for % of remaining current (the peak from both 1 mM glutamate and blocker/the peak in the presence of only 1 mM glutamate× 100) in the presence of various blockers such as NFA (50 □M), NPPB (50 □M), DIDS (50 □M), Quinine (100 □M), and PPADS (50□M) (**, p=0.008).

Figure 11F:
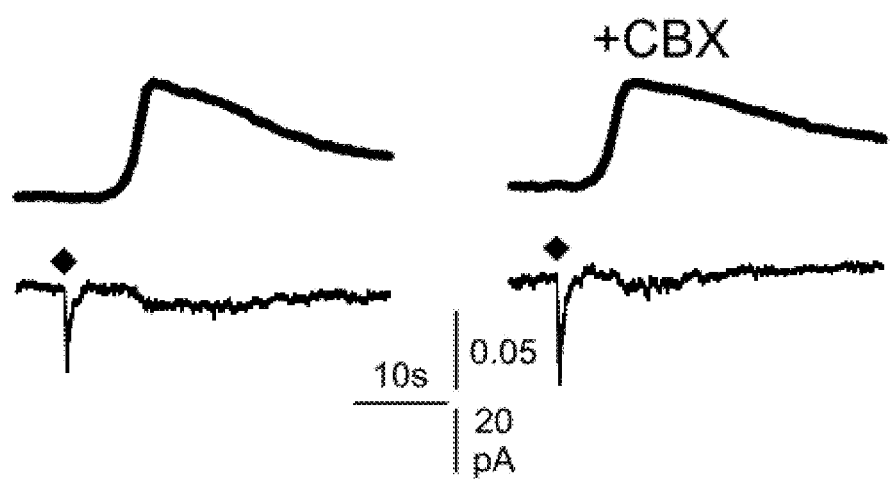
Figure 11G:
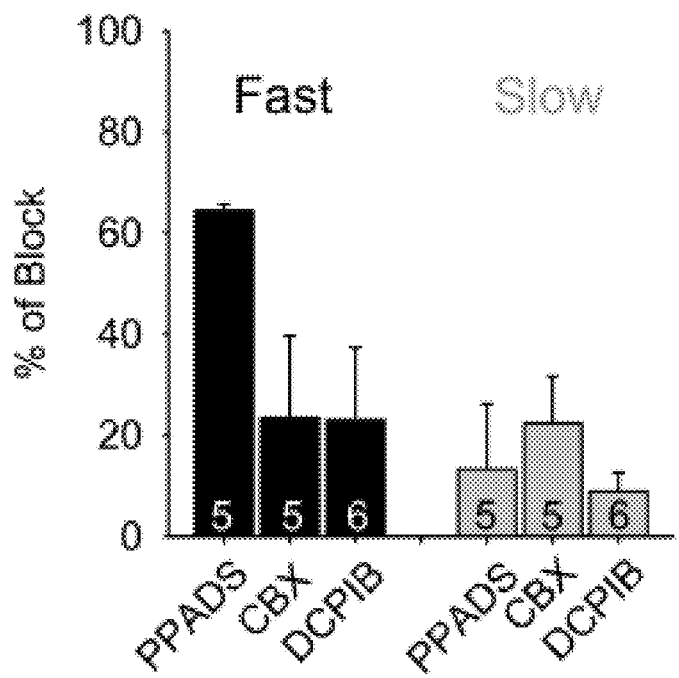

FIG. 11f to FIG. 11j show the effect of various blockers on TFLLR-induced fast and slow glutamate and inhibition of TREK-1 channel by PPADS; FIG. 11f represents a representative data showing that 50 μM Carbenoxolone (CBX, 10 min pre-incubation) does not inhibit TFLLR-induced GluR1-mediated current. +CBX indicates the presence of CBX, and FIG. 11g is a summary graph showing % of block in the presence of 50 μM PPADS (a known P2X channel blocker), 50 μM CBX (hemi-channel blocker), and 50 μM DCPIB (volume-activated chloride channel blocker).

Figure 11H:
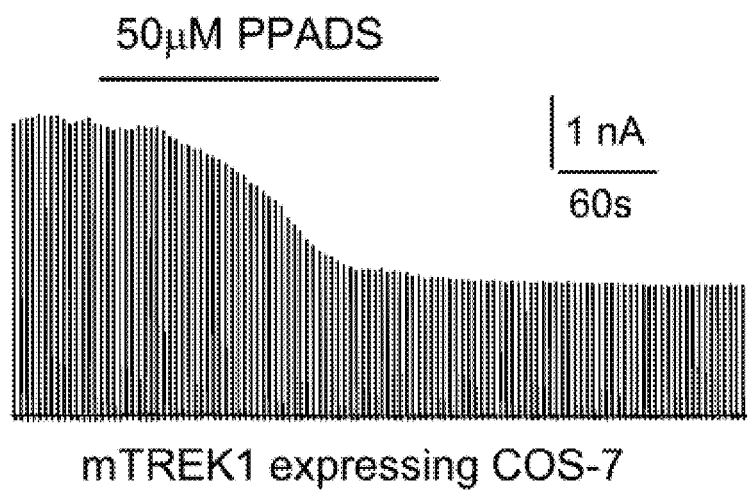

FIG. 11h shows the series of voltage ramp traces (ramp from −150 mV to +50 mV) for instantaneous I-V relationship showing that PPADS inhibits TREK-1-mediated currents in COS-7 cell expressing mouse TREK-1.

Figure 11I:
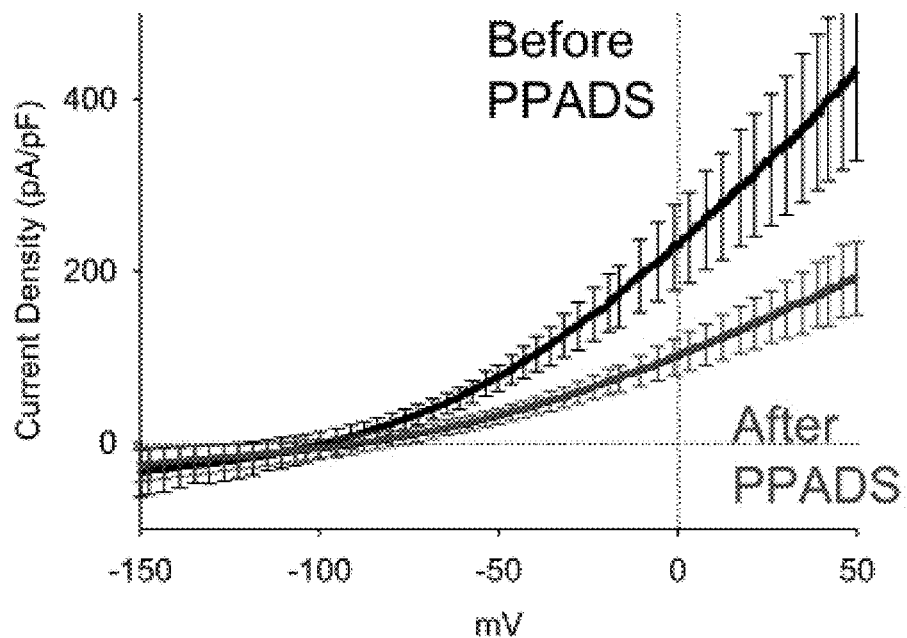

FIG. 11i shows an average current density of I-V relationship of before and after the treatment of PPADS.

Figure 11J:
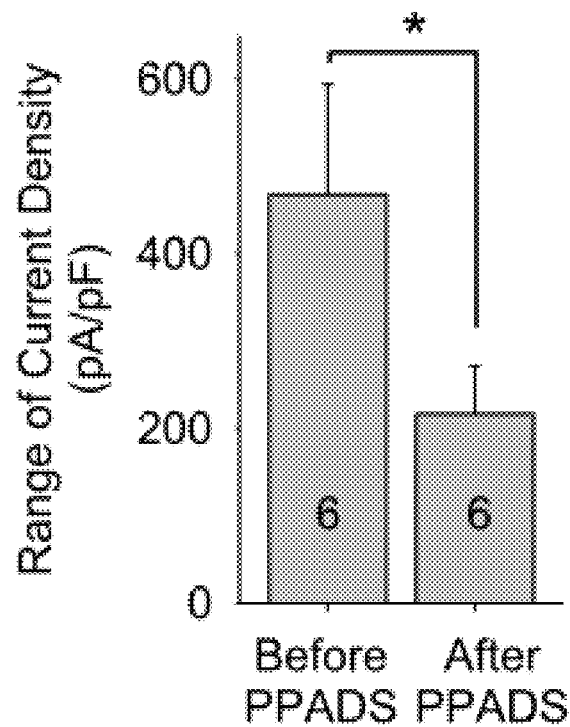

FIG. 11j is a summary graph for the range of current density (from −150 mV to +50 mV) before and after PPADS (*, p=0.023).

Figure 11K:
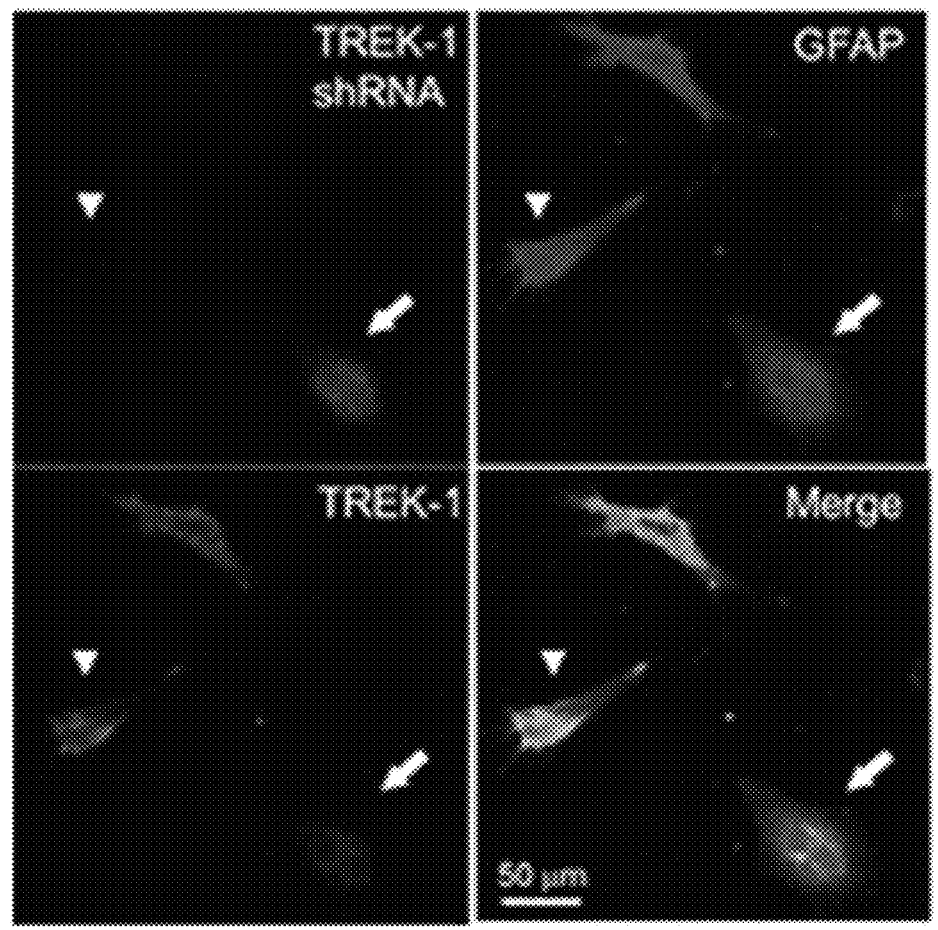
Figure 11L:
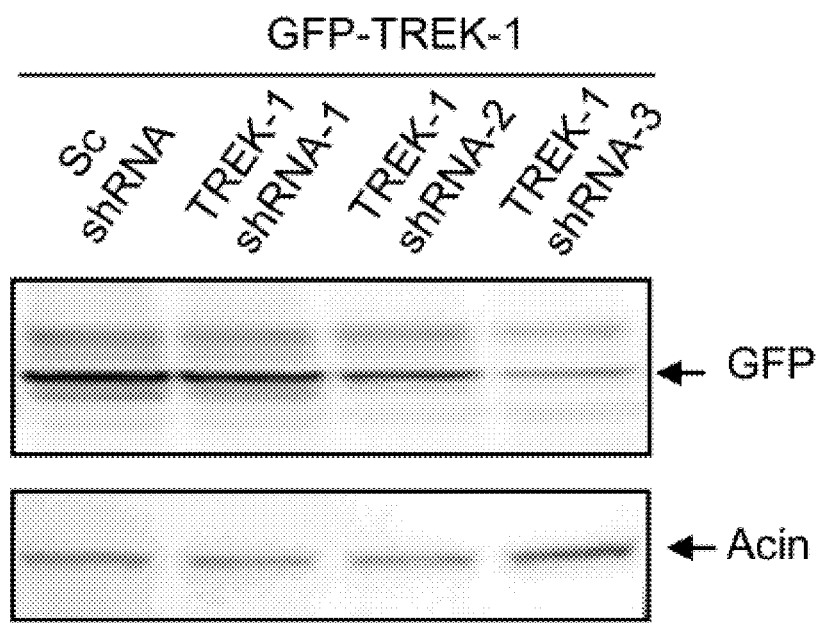
Figure 11M:
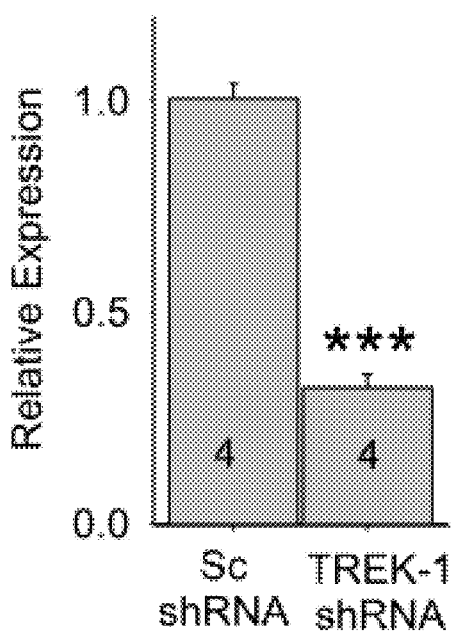

FIG. 11k to FIG. 11m represents the screening of mouse TREK-1 shRNA and validation of the shRNA and TREK-1-specific antibody.

FIG. 11k represents the gene silencing of mouse TREK-1 that was tested by western blotting. Three pre-designed shRNAs were co-transfected with mouse GFP-TREK-1 clone into HEK293T cells.

FIG. 11l shows the TREK-1 mRNA level of TREK-1 shRNA-3-transfected astrocytes was which measured by real-time PCR and normalized to that of astrocyte transfected with scrambled shRNA. Values are mean±s.e.m. (***, p<0.001).

FIG. 11m shows the Validation of TREK-1 antibody. Red color (first panel) represents astrocyte expressing TREK-1 shRNA.

FIG. 12a to FIG. 12f represent that N-terminus of TREK-1 binds to $G_\gamma$ subunit and $G_{\beta\gamma}$ injections induce chloride current.

Figures 12A, 12B:
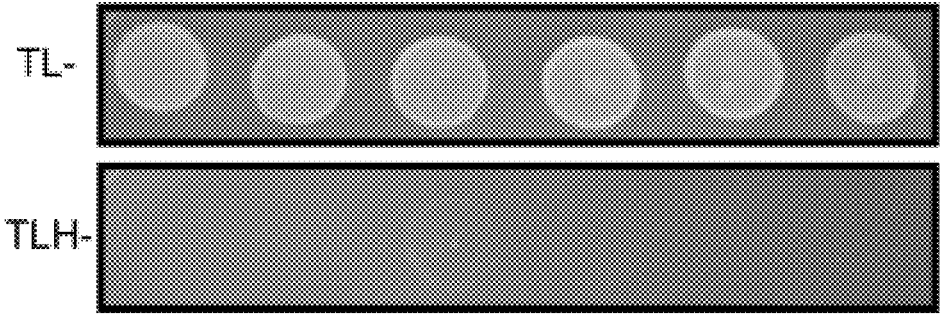

FIG. 12a shows a schematic diagram represents amino acid (a.a.) sequences of TREK-1. 1-46 a.a is divided into 4 domains. Red plus marks represent the degree for interaction between indicated region of TREK-1 and GNG4, a $G_\gamma$ subunit on yeast two hybrid systems.

FIG. 12b shows the negative response as control indicates no interaction between vectors and $G_\gamma$ subunit for yeast two hybrid experiment.

Figure 12C:
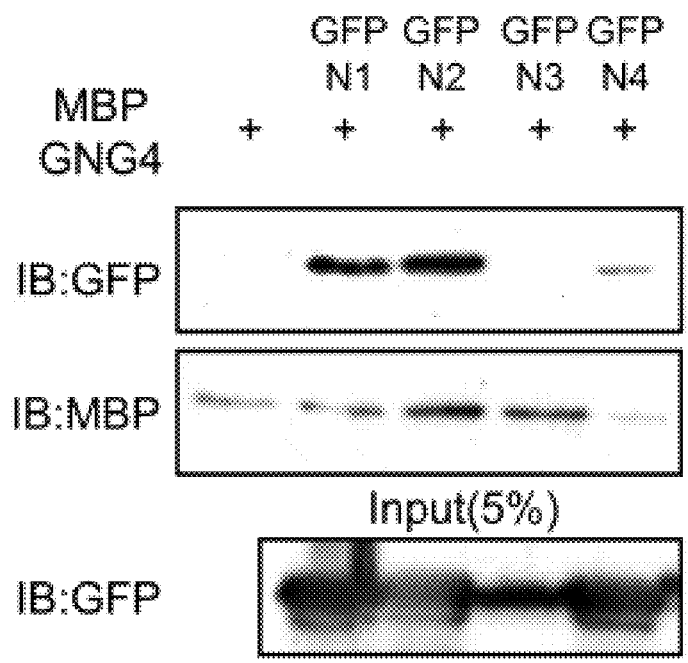

FIG. 12c is an immunoprecipitation result showing that N1, 2, and 4 selectively bind to GNG4 subunit.

Figure 12D:
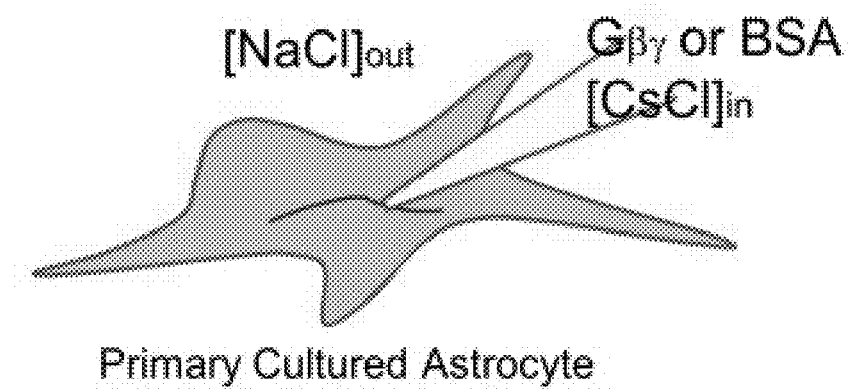
Figure 12E:
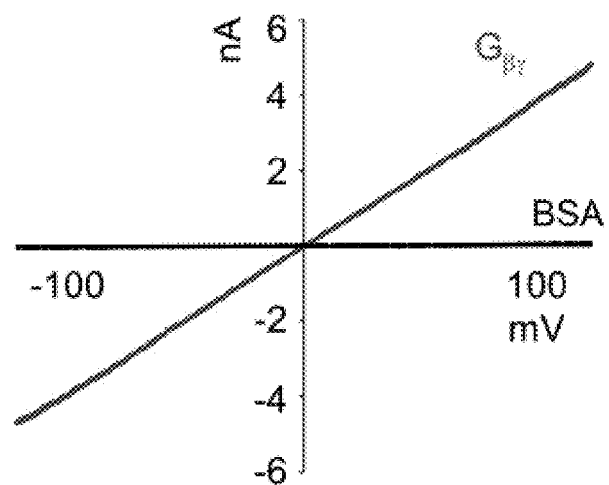

FIG. 12d shows a schematic diagram for the experiment of I-V relationship curve FIG. 12e shows I-V curves of 6.09 nM $G_{\beta\gamma}$ (red) and 6.09 nM BSA-induced current (black) on primary culture astrocytes.

Figure 12F:
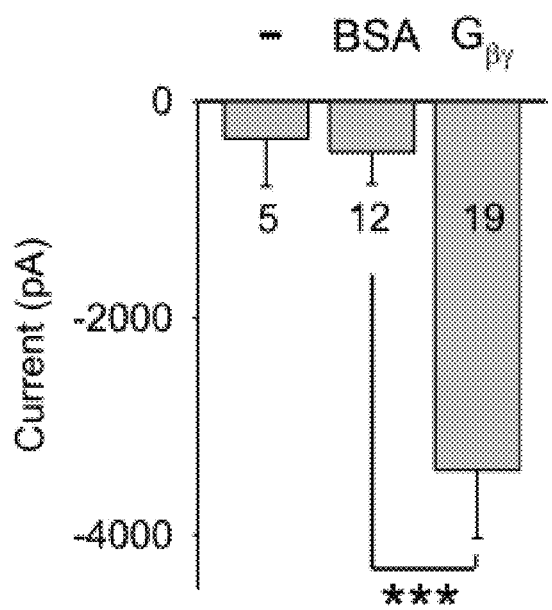

FIG. 12f is a summary bar graph for current amplitudes at −100 mV on the indicated conditions. Values are mean±s.e.m. (**, p=0.005).

FIG. 13a to FIG. 13f are the Electron microscopic immunostainings result showing the surface expressions of Best1 in a microdomain, but not those of TREK-1, Best1 (13a-13c) and TREK-1 (13d-13f) are stained with immunogold with silver enhancement (dark specks, arrowheads), and GFP, representing astrocyte, is stained with immunoperoxidase (dark amorphous deposits, arrows).

Figure 13A:
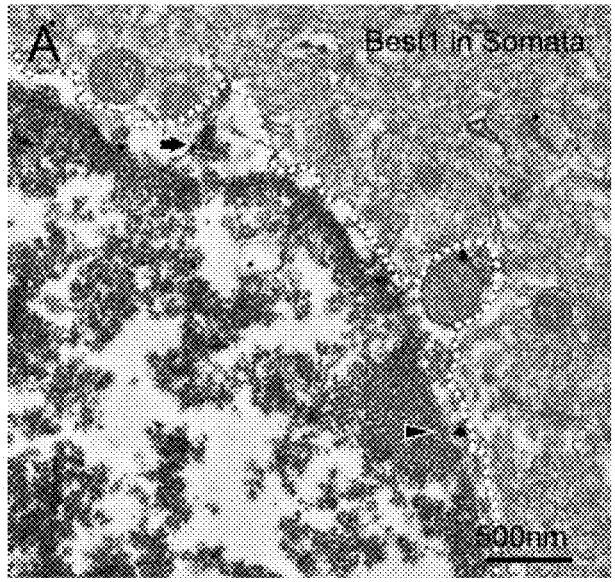

FIG. 13a shows that Best1 immunolabeling is modest in the cell body of the astrocyte.

Figure 13B:
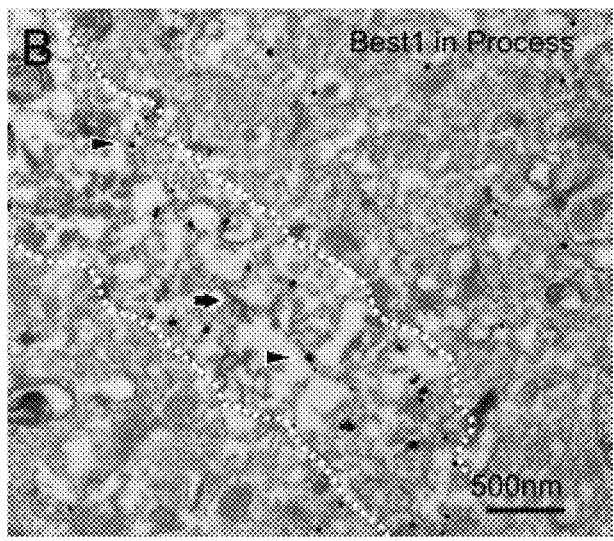

FIG. 13b represents that many gold particles showing mBest1 immunolabeling are observed in the cytoplasm but few in or near the cellular membrane of the stem process.

Figure 13C:
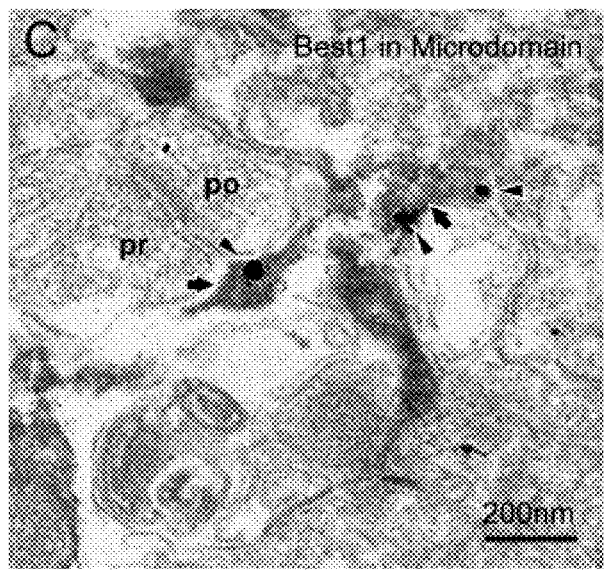

FIG. 13c shows the Best1 immunolabeling result which is largely observed in or near the membrane of the thin peripheral process (microdomain).

Figure 13D:
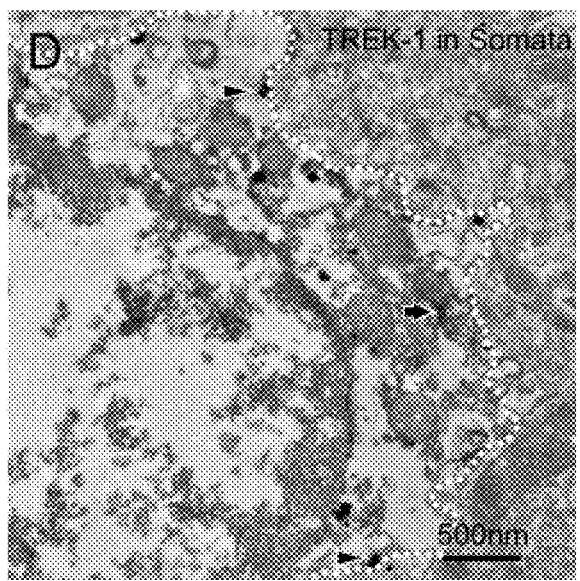
Figure 13E:
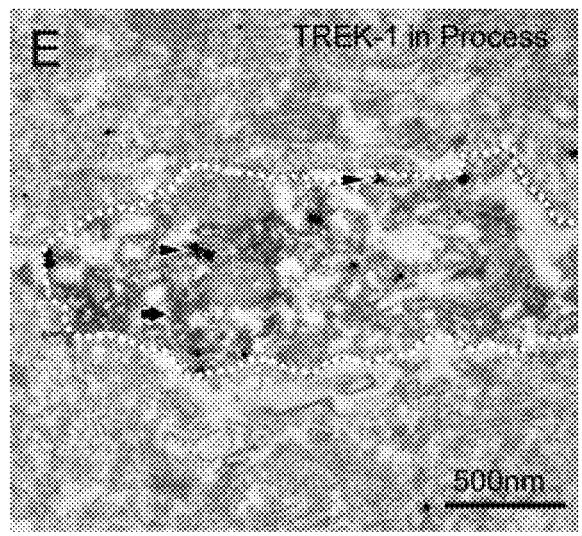

FIG. 13d and FIG. 13e show many gold particles showing TREK-1 immunolabeling are observed in the cytoplasm but predominantly near or at the cellular membrane of cell body (13d), and stem process (13e).

Figure 13F:
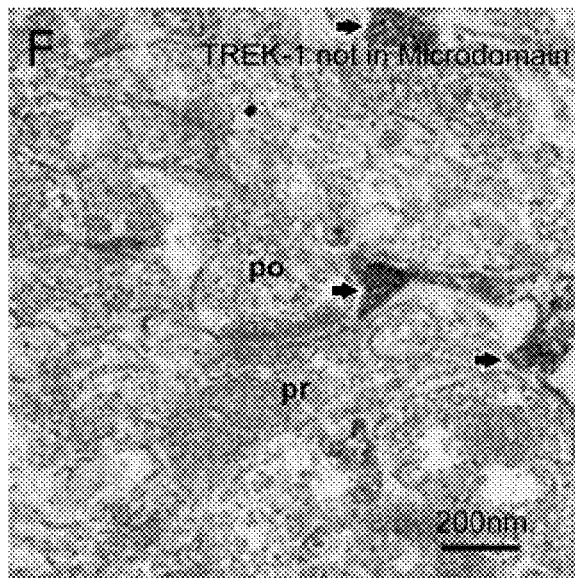

FIG. 13f shows that TREK-1 immunolabeling is not observed in the microdomain.

FIG. 14a to FIG. 14d show that exocytosis inhibitors reduce the TREK-1- and Best1-mediated currents.

Figure 14A:
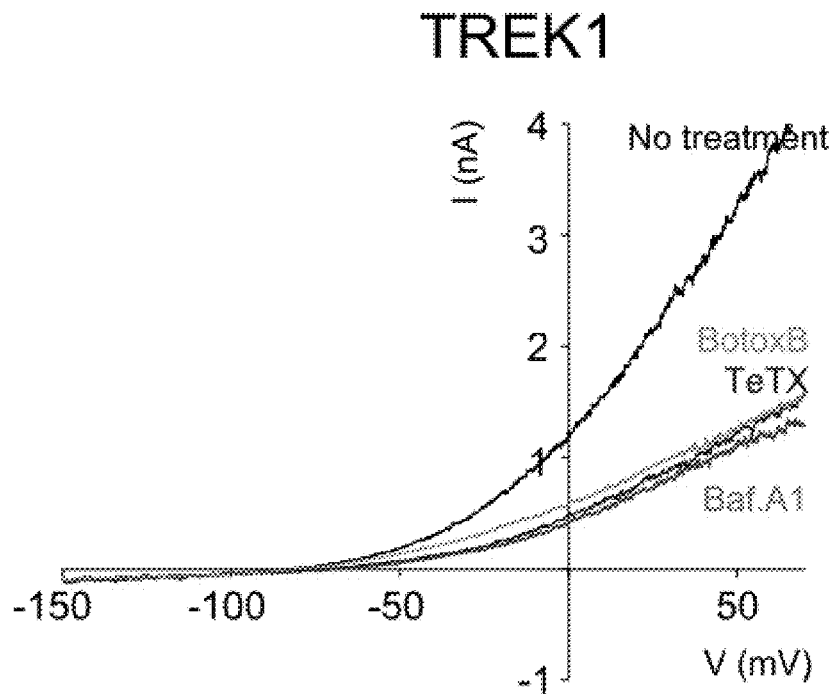

FIG. 14a shows I-V curves of TREK-1-expressing Cos-7 cells with the treatment of Tetanus Toxin (TeTX, blue) or Bafilomycin A1 (Baf. A1, red). 20 nM TeTX was injected to COS-7 cell expressing TREK-1. 2 μM Baf. A1 was pretreated with COS-7 cell expressing TREK-1 for 1 to 1.5 hr, and Ramp is from +70 to −150 mV. Representative traces are collected at 5 min during the indicated condition.

Figure 14B:
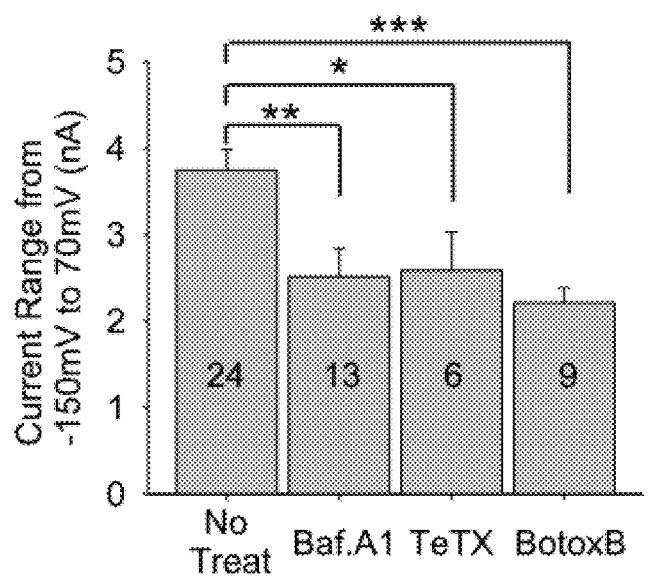

FIG. 14b is a summary bar graph for the current range (current amplitude at +70 mV-current amplitude at −150 mV) shows a significant difference (**, p=0.003, *, p=0.019).

Figure 14C:
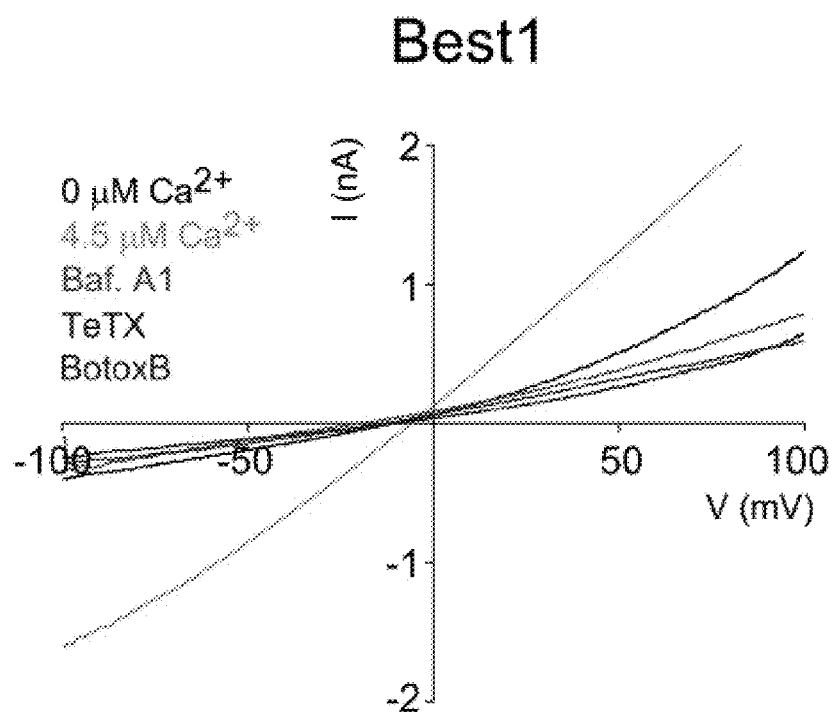

FIG. 14c shows I-V curves for $Ca^{2+}$-activated anion current recorded from cultured astrocyte. The current is inhibited by the injection of 20 nM TeTX or by the pretreatment of 2 μM Baf A1. I-V curves are recorded by internal pipette solutions following conditions (mM); 135 NMDG-Cl+0 μM $Ca^{2+}$ (black), 135 Cl+4.5 μM $Ca^{2+}$ (green), 135 NMDA-Cl+4.5 mM $Ca^{2+}$ (blue), 2 μM Baf. A1 is pretreated extracellularly for 1 hr), 135 NMDG-Cl+4.5 μM $Ca^{2+}$+20 nM TeTX (red). External condition is 150 mM NMDG-Cl.

Figure 14D:
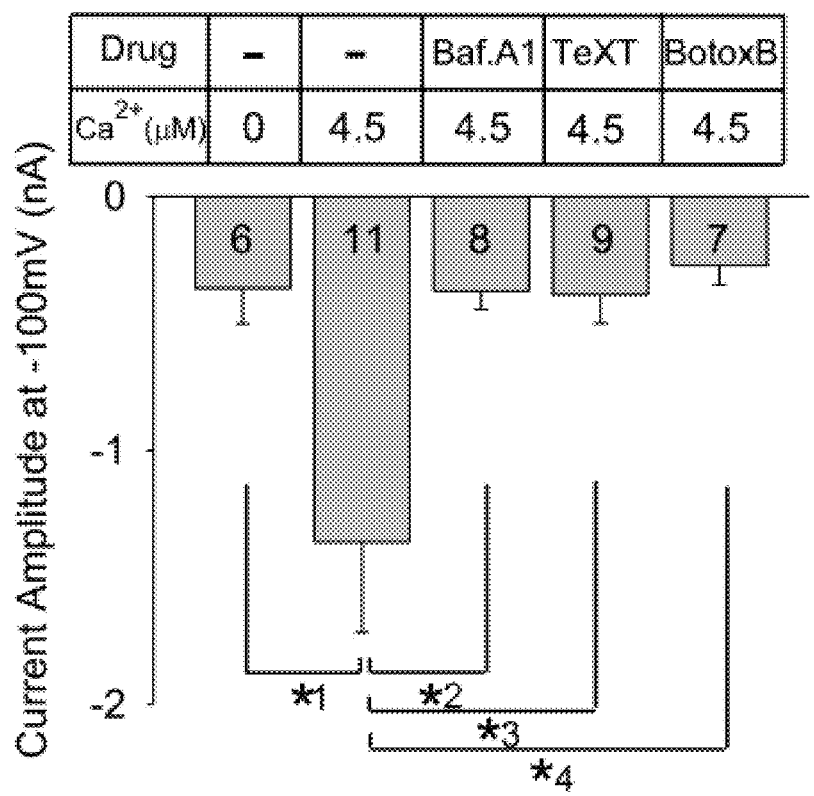

FIG. 14d is a summary bar graph for current amplitudes at −100 mV (*1, p=0.04, *2, p=0.03, *3, p=0.01).

The present invention is further explained in more detail with reference to the following examples. These examples, however, should not be interpreted as limiting the scope of the present invention in any manner.

<Chemicals>

Rose Bengal (RB), Poly-D-lysine (PDL) Niflumic acid (NFA), 5-Nitro-2-(3-phenylpropylamino)benzoic Acid (NPPB), 4,4'-Diisothiocyano-2,2'-stilbenedisulfonic acid (DIDS), 4-(2-butyl-6,7-dichloro-2-cyclopentylindan-1-on-5-yl)oxybutyric acid (DCPIB), Carbenoxolone (CBX), pyridoxal phosphate-6-azophenyl-2',4'-disulfonic acid tetrasodium salt (PPADS), Pertussis Toxin (PTX), 1,2-bis-(o-inophenoxy)ethane-N,N,N',N'-tetraacetic Acid Tetra-(acetoxymethyl) Ester (BAPTA-AM), BAPTA-pentapotassium salt, 2-chloro-N(6)-cyclopentyladenosine (CCPA), Baclofen, N-(2-Chloroethyl)-5Z,8Z,11Z,14Z-eicosatetraenamide (ACEA), Forskolin were purchased from Sigma Chemicals, USA. Bafilomycin A1 (Baf.A), Concanamycin A (Conc.A), Tetanus Toxin (TenT), 6-cyano-7-nitroquinoxaline-2,3-dione (CNQX) 3-isobutyl-1-methylxanthine (IBMX) were purchased from Tocris, USA. Botulinum Toxin B (BoToxB) was purchased List Biological Lab, USA. Effectine was purchased from Qiagen, USA. The 5 amino acid peptide, TFLLR-NH2 was synthesized by Peptron, Korea. Pluronic acid (F-127) and Fura-2 AM were purchased from Molecular Probe, USA

EXPERIMENTATION 1

Gene Cloning and shRNA Vector Design 1-1. G Protein Signaling

Regulatory G protein signaling 2 (pSport6-RGS-2) was purchased from Openbiosystems. GiCG (pcDNA3.1-SS-ECFP-TM-$G_{\Box i}$ C351G) and Gs (pcDNA3.1-SS-ECFP-TM-Gs) were kindly provided by Dr. Nevin Lambert. The C-terminus of Beta-adrenergic receptor kinase (pRK-βArk-ct) was kindly provided by Dr. Lucie Langevin. C-terminus of mouse phosducin (251-278 a.a.) (SEQ ID NO:6: efmvtdqlgedf-favdleaflqefgllpekegsg) was amplified by PCR with a pair of primers (Sense primer: 5'-ggggaattcatggtcactgaccagctgggg-3' SEQ ID NO: 7; antisense primer 3'-cccggatccctattccttttctgggagcaatcc-5' SEQ ID NO: 8) under the PCR conditions of 95° C. 1 minute, annealing: 58° C. 1 minute, extension: 72° C. 30 seconds, 35 cycle, DNA polymerase: taq polymerase (New England Biolabs)). The amplified product was inserted into pIRES2-dsRed vector (Clontech) by using EcoR1 and BamH1 sites.

1-2. Best1-shRNA, shRNA Insensitive Form of Mouse Best1, and Best1-W93C Pore Mutant (shRNA Insensitive Form)

The mouse Best 1 nucleotides (NM_011913.2) from 774 to 793 (5'-tttgccaacttgtcaatgaa-3': SEQ ID NO:9) was selected for the target region of shRNA. The pSicoR-Best1-shRNA was synthesized using the complementary oligomers, 5'-tagccaacttgtcaatgaattcaagagatcattgacaagttggcaattttttc-3' (SEQ ID NO: 10) and 5'-cgagaaaaaatcgcatagcgtatgccg-tactettgaaaacggcatacgctatgcgaa-3' (SEQ ID NO:11). The annealed double-stranded oligomer was inserted into HpaI-XhoI restriction enzyme sites of pSicoR lentiviral vector (Addgene) and verified by sequencing. Scrambled shRNA-containing pSicoR construct was used as control. The shRNA insensitive form of Best1 was generated with the Quikchange Multi Site-Directed Mutagenesis Kit (Stratagene) using oligonucleotide primers; sense 5'-gacagctacattcagctcatctg-catatccttcgttctgggtttc-3 (SEQ ID NO: 12)', antisense 5'-gaaacccagaacgaaggatatgcagatgagctgaatgtagagtc-3' (SEQ ID NO: 13) and confirmed by sequencing.

Best1 pore mutant (Best-W93C) was obtained by performing oligonucleotide-directed mutagenesis using the Quickchange Site-Directed Mutagenesis Kit (Stratagene) using oligonucleotide primers; sense 5'-ggtgagccgctgctggagccagtac-3'(SEQ ID NO:14), antisense 5'-gtactggctccagcagcggctcacc-3'(SEQ ID NO:15) and confirmed by sequencing.

1-3: Rat TREK-1 cDNA encoding full-length rat TREK-1 (GenBank Accession No. AY727922) (SEQ ID NO: 16) was obtained by an RT-PCR-based gateway cloning method as described previously.

1-4: TREK-1-shRNA

TREK-1-shRNA for mouse TREK-1 (NM_001159850) was targeted at the nucleotides from 1043 to 1063 (5'-gcgtg-gagatctacgacaagt-3': SEQ ID NO: 17) and similarly inserted into the pSicoR system as Best 1-shRNA, according to the same method of Experimentation 1-2.

EXPERIMENTATION 2

Cell Culture 2-1. Primary Cortical Astrocytes.

Primary cortical astrocytes were prepared from P0-P3 of C57BL/6 mouse or GFAP-GFP transgenic mouse (Jackson laboratory) according to the guideline of KOREA INSTITUTE OF SCIENCE AND TECHNOLOGY, Seoul, Korea).

The cerebral cortex was dissected free of adherent meninges, minced and dissociated into single cell suspension by trituration. All experimental procedures described were performed in accordance with the institutional guidelines of Korea Institute of Science and Technology (KIST, Seoul, Korea). Cells were grown in Dulbecco's modified Eagle's medium (DMEM, Invitrogen) supplemented with 25 mM glucose, 10% heat-inactivated horse serum, 10% heat-inactivated fetal bovine serum, 2 mM glutamine and 1000 units/ml penicillin-streptomycin. Cultures were maintained at 37° C. in a humidified 5% $CO_2$ incubator. On the $3^{rd}$ day of culture, cells were vigorously washed with repeated pipetting and the media was replaced to get rid of debris and other floating cell types. On the next day ($4^{th}$ day of culture), cells were replated onto coverglass ($1\times10^4$ per coverglass) coated with 0.1 mg/ml Poly D-Lysine (PDL), and during this procedure cultured astrocytes were transfected with various cDNAs and shRNAs by electroporation.

2-2. Human Embryonic Kidney (HEK) 293T Cells Expressing GluR1-L497Y

HEK 293T (HEK) cells were purchased from the Korean Cell Line Bank (Seoul National University) and cultured in DMEM (Invitrogen) supplemented with 10% fetal bovine serum (Invitrogen), 100 units/ml penicillin (Invitrogen), and 100 □g/ml streptomycin (Invitrogen) at 37° C. in a humidified atmosphere of 95% air and 5% $CO_2$. One day before the experiment for sniffer-patch, HEK cells were transfected with 1:10 ratio of green fluorescence protein (pEGFP-N1) and pCINeo-GluR1-L497Y (5 □g per 60 mm dish) or 1:3 red fluorescence protein (pDsRed) and pCINeo-GluR1-L497Y using Effectine (Qiagen). 5 □M CNQX (Toris USA) was always supplemented in the medium to block the AMPA receptor-mediated cytotoxicity.

2-3. Preparation of Astrocytes and HEK Cells Expressing GluR1-L497Y for Sniffer-Patch.

On the $5^{th}$ day of culture, on the day of sniffer-patch, HEK cells expressing GluR1-L497Y were dissociated, triturated, and added ($5\times10^3$ cells per coverglass) onto the coverglass with primary cultured astrocytes. 5 µM CNQX was added to the mixed culture of astrocyte and HEK cells. HEK cells were allowed to settle for at least 1 hr before sniffer-patch. Sniffer-patch was performed always on the same day of mixing.

2-4. Preparation of Cortical Neurons and HEK Cells Expressing GluR1-L497Y for Sniffer-Patch.

For sniffer-patch from neurons, primary cortical cultured neurons were prepared from mouse P0-P1 as described. Cortex was dissected, and incubated with $Mg^{2+}$- and $Ca^{2+}$-free HBSS containing 0.025% trypsin, 6 µg/ml DNase, 1 mg/ml bovine serum albumin, and 10 mg/ml glucose for 15 min at 37° C. Trypsinization was stopped by adding 1 mg/ml soybean trypsin inhibitor, and digested tissue was centrifuged for 5 min at 1500 rpm. Resulting pellets were triturated with 10% FBS and 10% horse serum containing trypsin inhibitor and DNase. The cell suspension was passed through fire polished Pasteur pipette and centrifuged for 3 min at 1500 rpm. Cells were re-suspended in culture medium consisting of neurobasal medium (Invitrogen), 2% B27 supplement, 2 mM L-glutamine, and 1% penicillin-streptomycin (50 units/ml penicillin and 50 □g/ml streptomycin) (Invitrogen). Cells were plated at $2.5\times10^5$ cells per coverglass. Cultures were maintained in a humidified atmosphere containing 5% $CO_2$/95% $O_2$ at 37° C. On the day of sniffer-patch, HEK cells expressing GluR1-L497Y were added to cultured cortical neuron.

2-5. Preparation of Acutely Dissociated Astrocytes and HEK Cells Expressing GluR1-L497Y for Sniffer-Patch For the acutely dissociated hippocampal astrocytes, brains from GFAP-GFP mouse of 9-12 week age were sliced horizontally at 350 µm thickness (Leica VT1000s). The CA1 hippocampal region of each slice was mechanically dissociated with a tip of vibrating polished glass pipette, connected to an alternating electronic relay switch (Omron G2R-2-S) under the control of function generator (EZ digital, Korea) at 1 KHz sine wave function. After about 5 min of mechanical dissociation, the ACSF solution containing dissociated cells were collected and centrifuged for 5 min at 1000 rpm. Collected cells were plated on 0.1 mg/ml PDL-coated cover glass, and placed in an incubator for about 2 hrs before use. Then HEK cells expressing GluR1-L497Y were added onto the coverglass with acutely dissociated GFP-positive astrocytes. Sniffer-patch from acutely dissociated astrocytes was performed within 6 hrs of plating.

2-6. Transfection of Astrocytes

On the 4th day of culture when astrocytes were replated onto coverglass, primary cultured astrocytes were electroporetically transfected with various cDNAs or shRNAs with an optimized voltage protocol (1200V, 20 pulse width, 2 pulses) using the Microporator (Invitrogen). Cell number for each transfection was $2 \times 10^6$. The transfected cells were loaded onto coverglass and cultured for at least 36 hrs. On the day of sniffer-patch, transfected astrocytes were mixed with HEK cells expressing GluR1-L497Y. The following cDNAs and shRNAs were used.

5 g pSPORT6-RGS-2 (see Experimentation 1-1) and 0.5 g pDsRed for blocking $G_q$ signaling, 5 g pcDNA3.1-SS-ECFP-TM-Gil-CG (GiCG) or 5 g pcDNA3.1-SS-ECFP-TM-Gs for investigating $G_{\alpha i}$ signaling (received from Nevin A. Lambert; see Some G protein heterotrimers physically dissociate in living cells, Gregory J. Digby, Robert M. Lober, Pooja R. Sethi, and Nevin A. Lambert, PNAS, Nov. 21, 2006 vol. 103 no. 47 17789-17794), 5 g pRK-βArk-C terminus and 0.5 g pDsRed or 5 g pIRES2-dsRED-Phosducin-c terminus for inhibiting $G_{\alpha i}$-$G_{\beta \gamma}$ dissociation, 5 g pSicoR-Best1-shRNA for blocking Best1 expression, 5 g pSicoR-Best1-shRNA and 5 g pIRES2-dsRed-Best1 (shRNA insensitive form) for rescue experiment, 5 g pSicoR-Best 1-shRNA and 5 g pSicoR-TREK-1-shRNA for blocking fast and slow-modes, and 5 g pSicoR-TREK-1-shRNA and 5 g pIRES2-GFP-TREK-1 (rat) for the rescue experiment of fast-mode.

EXPERIMENTATION 3

Simultaneous Recording of Astrocytic $Ca^{2+}$ and HEK Cell Current for Sniffer Patch 3-1. Sniffer-Patch On the day of sniffer-patch, cultured astrocytes (HEK cells added) were incubated with 5 μM Fura-2 AM (mixed with 5 μl of 20% Pluronic acid) (Invitrogen) for 40 min and washed at room temperature, and subsequently transferred to a microscope stage for imaging. External solution contained (in mM): 150 NaCl, 10 Hepes, 3 KCl, 2 $CaCl_2$, 2 $MgCl_2$, 5.5 glucose, pH adjusted to pH 7.3 and osmolarity to 325 mOsmol $kg^{-1}$. Intensity images of 510 nm wavelength were taken at 340 nm and 380 nm excitation wavelengths using either iXon EMCCD (DV887 DCS-BV, ANDOR technology). Two resulting images were used for ratio calculations in Axon Imaging Workbench version 6.2 (Axon Instruments). GluR1LY-mediated currents were recorded from HEK cells expressing GluR1L497Y under voltage clamp ($V_h$=−70 mV) using Multiclamp 700B amplifier (Molecular Devices), acquired with pClamp 9.2. Recording electrodes (4-7Ω) were filled with (mM): 110 Cs-Gluconate, 30 CsCl, 0.5 $CaCl_2$, 10 Hepes, 4 Mg-ATP, 0.3 Na3-GTP and 10 BAPTA (pH adjusted to 7.3 with CsOH and osmolarity adjusted to 290-310 mOsm/kg with sucrose). For simultaneous recording, Imaging Workbench was synchronized with pClamp 9.2.

3-2. Pressure-Application of GPCR Agonists

During sniffer-patch, astrocytic PAR1 receptor was activated by pressure application of the PAR1 agonist, TFLLR through glass pipette containing 500 μM TFLLR, positioned near an astrocyte, using Picospritzer (Parker Instruement) for 100 ms. To activate G1 coupled GPCR, 1 μM CCPA (A 1 receptor agonist), 300 μM ACEA (CBI receptor agonist), or 300 μM Baclofen ($GABA_B$ agonist) was pressure-applied for 100 ms.

3-3. Pharmacology

To block GluR1-L497Y-mediated current, cells were pretreated with 10 μM CNQX for 5 min. For blocking $G_i$ signaling pathway, astrocytes were pretreated with culture media containing 1 μg/ml Pertussis Toxin (PTX) for 12-20 hrs before sniffer-patch. For blocking vesicular glutamate transporter (VGluT), mixed cells of astrocytes and HEK cells were pretreated with 1 μM Rose Bengal for 30 min. For blocking $H^+$-ATPase, mixed cells were pretreated with 5 μM Bafilomycin A 1 (for 30 min) or 1 μM Conconomycin A (for 1 hr). For blocking exocytosis, astrocytes were pretreated with the media supplemented with 4 μg/ml Tetanus Toxin (TenT) for 12-18 hrs. For injection of TenT, 4 μg/ml TenT and 200 □M Fura-2 penta-potassium salt (impermeable form) were added to internal pipette solution and injected into a single astrocyte using patch-pipette, following whole-cell patch. For Botulinum Toxin B (BoToxB) injection, 8 μg/ml of BoToxB (8 μg/ml bovine serum albumin as a control) and 200 μM Fura-2 penta-potassium salts were similarly injected. Injection time was 20 min and Fura-2 was used as an indicator for successful injection. Following blockers were used at 50 μM: NPPB, NFA, DIDS, DCPIB, PPADS, and CBX. Quinine was used at 100 μM. These drugs were pretreated for 10 min after the first 500 μM TFLLR application. Then the second TFLLR was applied in the presence of these blockers. For chelating cytosolic $Ca^{2+}$, mixed cells were pretreated with 20 μM BAPTA-AM for 30 min. BAPTA-AM treatment for 30 min was sufficient for completely block TFLLR-mediated $Ca^{2+}$ increase in $Ca^{2+}$ imaging (data not shown). To eliminate the possibility that the change in cAMP concentration induce any astrocytic glutamate release, 500 μM forskolin (to activate adenylate cyclase) was pressure-applied for 100 ms. For inhibition of phosphodiesterase activity to increase cAMP, cells were pretreated with 100 μM IBMX for 5 min, and then TFLLR was applied in the presence of 100 μM IBMX.

EXPERIMENTATION 4

Two Cell Sniffer Assay

On the day of sniffer-patch, cultured astrocytes (HEK cells added) were transferred to a microscope stage for imaging. External solution contained (in mM): 150 NaCl, 10 Hepes, 3 KCl, 2 $CaCl_2$, 2 $MgCl_2$, 5.5 glucose, pH adjusted to pH 7.3 and osmolarity to 325 mOsmol kg* Rupture current were recorded from astrocyte under voltage ($V_h$=−70 mV) using Multiclamp 700B amplifier (Molecular Devices), acquired with pClamp 9.2. Recording electrodes (4-7MΩ) were filled with (mM): 5 glutamate, 135 CsCl, 0.5 $CaCl_2$, 10 Hepes, 4 Mg-ATP, 0.3 Na3-GTP, 10 BAPTA and 6.09 nM $G_{\beta \gamma}$ (pH adjusted to 7.3 with CsOH and osmolarity adjusted to 290-310 mOsm/kg with sucrose). In the case of gene silencing, transfection method is the same as simultaneous recording for sniffer patch. In competition assay, 100 μM N1-N4 synthesized peptides were added to pipette for recording astrocyte. GluR1LY-mediated currents were recorded from HEK cells expressing GluR1-L497Y under voltage clamp ($V_h$=−70 mV) using Multiclamp 700B amplifier (Molecular Devices), acquired with pClamp 9.2. Recording electrodes (4-7MΩ) were filled with (mM): 110 Cs-Gluconate, 30 CsCl, 0.5 $CaCl_2$, 10 Hepes, 4 Mg-ATP, 0.3 Na3-GTP and 10 BAPTA (pH adjusted to 7.3 with CsOH and osmolarity adjusted to 290-310 mOsm/kg with sucrose). After rupture on the side of HEK cell, GluR1-L497Y-meidated full activation was induced by the treatment of 1 mM glutamate. And then $G_{\beta\gamma}$ on the side of astrocyte was injected with the rupture after 10 min later. This rupture induced both inward current on both recording between astrocyte and HEK cell expressing GluR1-L497Y.

EXPERIMENTATION 5

Yeast Two Hybrid System

The TREK-1-N 1-4 were ligated into pGBKT7 encoding for the GAL4 DNA binding domain (BD) and the gamma 4 was cloned into pGADT7 encoding for the activation domain (AD). To assess the protein-protein interaction between TREK-1-N and gamma 4, both BD/TREK-1-N and AD/gamma 4 were co-transformed into the yeast strain AH109. AH109 is unable to synthesize histidine. However, interaction between TREK1-N and gamma 4 enables the yeast to make the His3 enzyme, thereby permitting histidine biosynthesis and growth on His minimal medium.

EXPERIMENTATION 6

Pull Down Assay

GFP-gamma 4 and hemagglutinin (HA)-TREK-1 were co-expressed in HEK293T cells and extracted 24 h post-transfection. HA-IRK1 and HA-GirK1 were used as negative and positive controls for binding affinity. Cell lysates were immunoprecipitated with HA. After 2 h incubation at 4° C., the beads were washed four times with ice cold phosphate-buffered saline (PBS). Bound proteins were eluted with SDS sample buffer, separated on 12% SDS-PAGE gels. The blots incubated overnight at 4° C. with anti-HA antibody (1:1000; Santa Cruz Biotechnology) or anti-GFP antibody (1:1000; Ab cam). Blots were then washed and incubated with horseradish peroxidase-conjugated goat anti-mouse or antirabbit IgG, followed by washing and detection of immunoreactivity with enhanced chemiluminescence (Amersham Biosciences).

EXPERIMENTATION 7

Western Blotting

Gene silencing of TREK-1 was tested by western blotting. To observe shRNA-mediated inhibition of TREK-1 expression, both 1 μg of mouse pDS-GFP-DEST-TREK-1 and 1.5 pig of pSicoR-TREK-1-shRNA (see Experimentation 1-4) or 1.5 pig of pSicoR-scrambled-shRNA (5'-TCGCATAGCG-TATGCCGCAAGAGAAACGGCATACGC-TATGCGATTTTTTC-3', SEQ ID NO: 18) as control were co-transfected to $5\times10^5$ of HEK293T cells seeded on 35 mm dishes by using the transfection reagent, Effectine (Qiagen) (see Experiment 1-2). After 48 hr incubation, cells were lysed with RIPA buffer. 30 pig of proteins were separated by SDS-PAGE using 10% gels and blotted onto PVDF membranes. The blots were incubated overnight at 4° C. with anti-GFP antibody (1:1000; Santa Cruz Biotechnology). Blots were then washed and incubated with horseradish peroxidase-conjugated goat anti-mouse or anti-rabbit IgG, followed by washing and detection of immunoreactivity with enhanced chemiluminescence (Amersham Biosciences). The band intensity was acquired and analyzed by ImageQuant LAS 4000 (General Electric Company).

EXPERIMENTATION 8

Quantitative RT-PCR

Total RNA was extracted using RiboEx kit (GeneAll, Korea) from scrambled shRNA or TREK-1 shRNA transfected cultured astrocytes according to the manufacturer's recommendations. The purity and concentration of RNA was determined by measuring the absorbance at 260 nm and 280 nm. RNA was reverse-transcribed into cDNA (Superscript VILO cDNA synthesis kit, Invitrogen) in a total volume of 100 μl according to the manufacturer's instructions. All primers for mouse TREK-1 (NM_001159850) and GADPH (NM_008084) were designed and blasted using IDT Primerquest software (www.idtdna.com/primerquest).

The primer sequences for TREK-1 are shown.

```
Probe:
5'-/56-FAM/ccgcctcct/ZEN/cgtttccttgaact/3IABkFQ/-
3'.

Primer 1:
                                        (SEQ ID NO: 19)
5'-tggctacgggtgatctctaag-3'.

Primer 2:
                                        (SEQ ID NO: 20)
5'-gctggaacttgtcgtagatctc-3'.
```

The primer sequences for GAPDH are shown.

```
Probe:
5'-/56-FAM/tgcaaatgg/ZEN/cagccctggtg/3IABkFQ/-3'.

Primer 1:
                                        (SEQ ID NO: 21)
5'-gtggagtcatactggaacatgtag-3'.

Primer 2:
                                        (SEQ ID NO: 22)
5'-aatggtgaaggtcggtgtg-3'.
```

Real-time PCRs were performed in 96 well plates on an ABI Prism 7500 Sequence Detection System (Applied Biosystems StepOnePlus™ Real Time PCR System). Final reaction volumes were 20 μl. Each sample was analyzed in triplicate. Thermal cycler conditions were as follows: 2 min at 50° C., 15 min at 95° C., followed by 40 cycles of 15 s at 95° C. and 1 min at 60° C. Sequence Detector Software (Applied Biosystems) was used to extract PCR data, which were exported into Excel 2010 (Microsoft Corporation, Redmond, Wash.) for further analyses. The amount of targeted gene expressed was normalized to an endogenous reference and relative to a calibrator. GAPDH was used as an endogenous reference in these experiments. The formula $2^{-\Delta\Delta Ct}$ was used to calculate the amount of target gene expression normalized to the endogenous control and relative to the calibrator.

EXPERIMENTATION 9

Immunocytochemistry of Cultured Astrocytes

The specificity of TREK-1 antibody (Alomone labs, rabbit polyclonal antibody 1:100) was tested by immunocytochemistry in cultured astrocytes in combination with TREK-1-shRNA. Primary cultured astrocytes were transfected with TREK-1-shRNA, grown on coverslips for additional 48 hr. The cells were fixed in 4% paraformaldehyde for 30 min at room temperature, then permeabilized with PBS with 0.5%

NP40 for 5 min. Non-specific binding was prevented with a 1 hr incubation with 2% donkey serums. Cells were incubated with the anti-TREK-1, and anti-GFAP (Millipore, chicken polyclonal antibody 1:500) primary antibodies for overnight at 4° C. After washing, DyLight 488 or 649-conjugated secondary antibody (Jackson lab, 1:400) was added and incubated for 2 hr at room temperature. The cells were washed and mounted, and then observed under a Nikon A 1 confocal microscope.

EXPERIMENTATION 10

Modeling Using Diffusion Equation

To estimate the total glutamate released from a single astrocyte, we utilized a mathematical model, the diffusion equation, considering the geometrical constraints of the sniffer-patch technique. We have assumed that each astrocyte releases glutamate on an impermeable boundary wall and homogenously on the top surface of the cell. If we assume the diffusion coefficient of glutamate D is constant in space and there is no external potential, the diffusion equation (It*o, 1992) can be written by $$\frac{\partial \phi}{\partial t}(x, t) = D\nabla^2 \phi(x, t) \quad \text{(Equation 1)}$$

where $\phi$ is concentration, t time, and x position in three dimension. Note that the operator $$\frac{\partial}{\partial t}$$

is the partial derivative with respect to t and $\nabla^2$ is the Laplace operator defined as following in the Cartesian coordinate system;

$$\nabla^2 = \frac{\partial^2}{\partial x_1^2} + \frac{\partial^2}{\partial x_2^2} + \frac{\partial^2}{\partial x_3^2} \quad \text{(Equation 2)}$$

with the definition of $x=(x_1, x_2, x_3)$.

We use $D \equiv 0.3 \ \mu m^2/ms$ as the glutamate diffusion coefficient (Beenhakker and Huguenard, 2010). If glutamate is released from a point source at $x=x_0$ and at time $t=0$, the initial condition of a point impulse of glutamate release is, $\phi_{x_0}(x,0) \equiv \delta(x-x_0)$ where $\delta$ is the Dirac delta function. Then, by solving the partial differential equation (Equation 1), we can derive the solution for this initial condition as, $$\phi_{x_0}(x, t) \equiv (4\pi Dt)^{-3/2} e^{-\frac{|x-x_0|^2}{4Dt}}$$

for three-dimensional space. Therefore, for an arbitrary initial condition, $\phi(x,0)$, we have the general solution of Equation 1, $$\phi(x,t) = \int \phi_{x_0}(x,t)\phi(x_0,0)dx_0 \quad \text{(Equation 3)}$$

where this general solution is an integral of the impulse response of glutamate release at a point ($\phi_{x_0}(x,t)$) multiplied by the initial condition depending on the shape of the glutamate source ($\phi(x_0,0)$). We used the shape of a single astrocyte as a square with dimensions of 100 ☐m×100 ☐m. In our sniffer-patch experiment to detect glutamate release from an astrocyte, the sensor detected the glutamate by current measurement which is then converted to concentration (using the concentration-response relationship of GluR1-L497Y for glutamate) as, $\phi_e(x_d,t)$, at a detection point $x_d$, which is unknown. By computer simulation of the model (Equation 2) and comparing with the experimental concentration profile, $\phi_e(x_d,t)$, we have obtained the best-fit detection point $x_d$. Once the detection point $x_d$ is calculated, we can determine the ratio between the concentrations at the original source and at the detection point, which then can be used to calculate the original quantity of the glutamate release from a single astrocyte.

After the quantity of glutamate release from a single astrocyte is calculated, we varied the distance of detection point in Equation 2 to simulate the concentration of glutamate that a target glutamate receptor can sense on the opposing neuronal membrane. The distance was varied from 10 nm to 40 nm to mimic the distance between the astrocytic membrane and neuronal membrane. The resulting concentration profile for the fast-mode glutamate release reached about 100 ☐M at the peak, ranging from 130 to 100 µM with respect to distance of 10 to 40 nm. Because the rise time of the detected concentration profile showed a very fast kinetics, we assumed an impulse release of glutamate, which fit very well with the experimental concentration profile. However, for the slow-mode release of glutamate, the impulse release did not fit well with the experimental concentration profile. Therefore, we assumed continuous release of glutamate and used a $4^{th}$ order polynomial to fit the experimental concentration profile. The predicted concentrations of glutamate at different distances of 10-40 nm came out to be very similar, as 0.8-0.9 µM. Therefore, the concentration of fast-mode was about 100 times more than the slow-mode at the peak. From these estimated concentrations of glutamate at the opposing neuronal membrane, we predicted the receptor type by comparing them to the known concentration-response relationships of glutamate receptor types for glutamate. We predicted that the slow-mode can preferentially activate NMDA receptors whereas the fast-mode can activate both NMDA receptors and metabotropic glutamate receptors (mGluR).

EXPERIMENTATION 11

Electron Microscopic Immunohistochemistry

Three GFP-GFAP transgenic mice weighing 20-25 g were used for this study. For tissue fixation, mice were deeply anesthetized with sodium pentobarbital (80 mg/kg, i.p.) and perfused transcardially with 10 ml of heparinized normal saline, followed by 50 ml of a freshly prepared mixture of 4% paraformaldehyde and 0.01% glutaraldehyde in 0.1 M phosphate buffer, pH 7.4 (PB). Hippocampus were removed and postfixed in the same fixative for 2 hrs at 4° C. Sections were cut sagittally on a Vibratome at 60 um and cryoprotected in 30% sucrose in PB overnight at 4° C. Sections were frozen on dry ice for 20 minutes, thawed in phosphate-buffered saline (PBS; 0.01 M, pH 7.2) to enhance penetration. They were pretreated with 1% sodium borohydride for 30 min to quench glutaraldehyde and then blocked with 3% $H_2O_2$ for 10 min to suppress endogenous peroxidases and with 10% normal donkey serum (NDS, Jackson ImmunoResearch, West Grove, Pa.) for 30 minutes to mask secondary antibody binding sites. For double immunostaining for GFP and Best1 or TREK-1, sections of hippocampus pretreated as above were incubated overnight in a mixture of chicken anti-GFP (1:400; GFP-1020, 1229FP08, Aves labs, St. Tigard, Oreg.) and rabbit anti-Best 1 (1:200) or rabbit anti-TREK-1 (1:50; APC-047, AN-02, Alomone labs, Jerusalem, Israel) antibodies. The specificity of the Best1 antibody has been extensively tested in previous studies. After rinsing in PBS, sections were incubated with a mixture of biotinylated donkey anti-chicken (1:200, Jackson ImmunoResearch) and 1 nm gold-conjugated donkey anti-rabbit (1:50, EMS, Hatfield, Pa.) antibodies for 2-3 hrs. The sections were postfixed with 1% glutaraldehyde in PB for 10 minutes, rinsed in PBS several times, incubated for 8 min in silver intensification solution (IntenSE™ M, Amersham, Arlington Heights, Ill.), and rinsed in 0.1 M sodium acetate and PB. They were then incubated with ExtrAvidin peroxidase (1:5,000, Sigma, St. Louis, Mo.) for 1 hr and the immunoperoxidase was visualized by nickel-intensified 3,3'-diaminobenzidine tetrahydrochloride (DAB). Sections were further rinsed in PB, osmicated (0.5% osmium tetroxide in PB) for 30 min, dehydrated in graded alcohols, flat-embedded in Durcupan ACM (Fluka, Buchs, Switzerland) between strips of Aclar plastic film (EMS), and cured for 48 hrs at 60° C. Chips containing prominent staining for GFP and Best1 or TREK-1 in the CA1 region of the hippocampus were cut out of the wafers and glued onto blank resin blocks with cyanoacrylate. Serially cut thin sections were collected on Formvar-coated single-slot nickel grids and stained with uranyl acetate and lead citrate. Grids were examined on a Hitachi H 7500 electron microscope (Hitachi, Tokyo, Japan) at 80 kV accelerating voltage. Images were captured with Digital Montage software driving a MultiScan cooled CCD camera (ES1000W, Gatan, Pleasanton, Calif.) attached to the microscope and saved as TIFF files. To control for specificity of primary antibodies, we processed sections of CA1 region from three rats according to the above-described protocols, except that primary or secondary antibodies were omitted. Omission of primary or secondary antibodies completely abolished specific staining. In addition, specificity of the immunoreaction was also confirmed by the consistency of immunostaining in adjacent serial thin sections of the same astrocytes.

EXPERIMENTATION 12

TREK-1 and Best1 Mediated Whole Cell Current Recording

Current-voltage (I-V) curves were recorded from COS-7 expressing TREK-1. I-V curves were established by applying 1000-ms-duration voltage ramps from +70 to −100 mV. Data were acquired by an Axopatch 200A amplifier controlled by Clampex 9.2 via Digidata 1322A data acquisition system (Molecular Devices). Internal solution contained the following (in mM: 150 KCl, 5 EGTA, 10 HEPES, 0.5 $CaCl_2$, 1 $MgCl_2$, pH 7.3, 280 osm). Bath solution contains the following (in mM: 150 NaCl, 10 HEPES, 3 KCl, 2 $CaCl_2$, 2$MgCl_2$, and 5.5 glucose, pH 7.3). The pipette solution for observing $Ca^{2+}$ activated $Cl^-$ current (Best1 channel current) whole-cell patch clamp in astrocytes contained the following (in mM: 135 NMDG-Cl, 5 $MgCl_2$, 5 ($Ca^{2+}$)-EGTA-N-methyl-D-glucamine (NMDG), 10 HEPES, and 10 glucose, pH 7.3, adjusted with NMDG). We used $Ca^{2+}$-free intracellular solution composed of the following (in mM: 135 NMDG-Cl, 5 EGTA-NMDG, 2 $MgCl_2$, 8 HEPES, and 10 sucrose, pH 7.3, adjusted with NMDG). I-V curves were established by applying 1000-ms-duration voltage ramps from +100 to −100 mV.

EXAMPLE 1

Characterization of Fast and Slow-Modes of Glutamate Release 1-1. Effect of $Ca^{2+}$ Concentration in an Astrocyte on the Glutamate Release To examine the signaling pathways mediating the fast and slow-modes of glutamate release, we utilized various molecular and pharmacological tools. Because the PAR1 receptor is linked to both $G_{110}$ and $G_{O2}$, we selectively inhibited the $G_i$ pathway by pre-incubating astrocytes with pertussis toxin (PTX), which is known to inhibit the action of $G_i$ subunit by ADP-ribosylation. Specifically, for blocking $G_i$ signaling pathway, astrocytes were pretreated with culture media containing 1 μg/ml Pertussis Toxin (PTX) for 12-20 hrs before sniffer-patch and then performed for sniffer-patch (see Experimentations 3-1 and 3-3). The results were shown in FIG. 1e, FIG. 1f, FIG. 1g, FIG. 9a and FIG. 9b.

As shown in FIG. 1e, FIG. 1f, FIG. 1g, FIG. 9a and FIG. 9b, we found that PTX selectively and almost completely blocked the fast but not the slow component of glutamate release, without affecting astrocytic $Ca^{2+}$ responses. This selective inhibition by PTX was significantly rescued by over-expression of a PTX-insensitive form of $G_1$, but not by over-expression of the $G_s$ subunit.

1-2. The Effect of Dissocation $G_{\beta\gamma}$ on the Glutamate Release

Activation of GPCRs is known to dissociate the $G_{s8}$ □ complex from the trimeric $G_i$-$G_{□□}$ complex, we further tested the role of $G_i$ by asking whether disturbing the $G_{□□}$ dissociation affects the fast-mode.

Specifically, the primary cultured astrocytes were electroporetically transfected according to an optimized voltage protocol (1200V, 20 pulse width, 2 pulses) using the Microporator (Invitrogen), with 5 g pcDNA3.1-SS-ECFP-TM-Gil-CG (GiCG) or 5 g pcDNA3.1-SS-ECFP-TM-Gs for investigating $G_{\alpha i}$ signaling, and 5 μg pRK-β-Ark-C terminus and 0.5 μg pDsRed or 5 μg pIRES2-dsRED-Phosducin-c terminus for inhibiting $G_{\alpha 1}$-$G_{\beta\gamma}$ dissociation (see Experimentation 2-6). Then, the sniffer-patch was performed. The results were shown in FIG. 1h to FIG. 1k, FIG. 9c, FIG. 9b, FIG. 9g and FIG. 9h.

As represented in FIG. 1h to FIG. 1k, FIG. 9c, FIG. 9b, FIG. 9g and FIG. 9h, Over-expression of the C-termini of phosducin and □-ARK, which have been reported to inhibit $G_{□□}$ dissociation, almost completely inhibited the fast-mode (FIG. 1h to FIG. 1i), without affecting the $Ca^{2+}$ responses (FIG. 9c and FIG. 9d).

The well-known agonists of $G_i$-coupled GPCR could induce fast glutamate release: baclofen, $GABA_B$ agonist, 2-chloro-N(6)-cyclopentyladenosine (CCPA), adenosine receptor A 1 agonist, and arachidonyl-2'-chloroethylamide (ACEA), cannabinoid receptor CB 1 agonist, all activated a fast-mode of glutamate release similar to that induced by TFLLR, without a measurable $Ca^{2+}$ increase or a slow-mode of glutamate release (FIG. 1j, 1k, FIG. 9g and FIG. 9h).

1-3. The Effect of $G_q$ Signaling on the Glutamate Release

To examine the involvement of $G_q$ signaling, we over-expressed RGS-2, which is reported to selectively inhibit the $G_q$ subunit. Particularly, the primary cultured astrocytes were electroporetically transfected with pSport6-RGS-2 (Regulatory G protein signaling 2) and then performed with sniff patch. The results were shown in FIG. 1*l*, FIG. 1*m*, FIG. 9*e*, and FIG. 9*f*.

As indicated in FIG. 1*l*, FIG. 1*m*, FIG. 9*e*, and FIG. 9*f*, we found that RGS-2 over-expression selectively and significantly inhibited both the slow component of glutamate release and the associated $Ca^{2+}$ increase, while not affecting the fast-mode.

$G_q$ signaling activates phospholipase $C_\square$, producing $IP_3$ and releasing $Ca^{2+}$ through the $IP_3R$ channel (Clapham, 2007). Thus, we tested the sensitivity of slow component to the $Ca^{2+}$ chelator, BAPTA (see Experimentation 3-3).

Specifically, for chelating cytosolic $Ca^{2+}$, mixed cells were pretreated with 20 µM BAPTA-AM for 30 min, and then performed with sniff patch. The results were shown in FIG. 1*n* and 1*o*. BAPTA-AM treatment for 30 min was sufficient for completely block TFLLR-mediated $Ca^{2+}$ increase in $Ca^{2+}$ imaging.

Figure 1A:
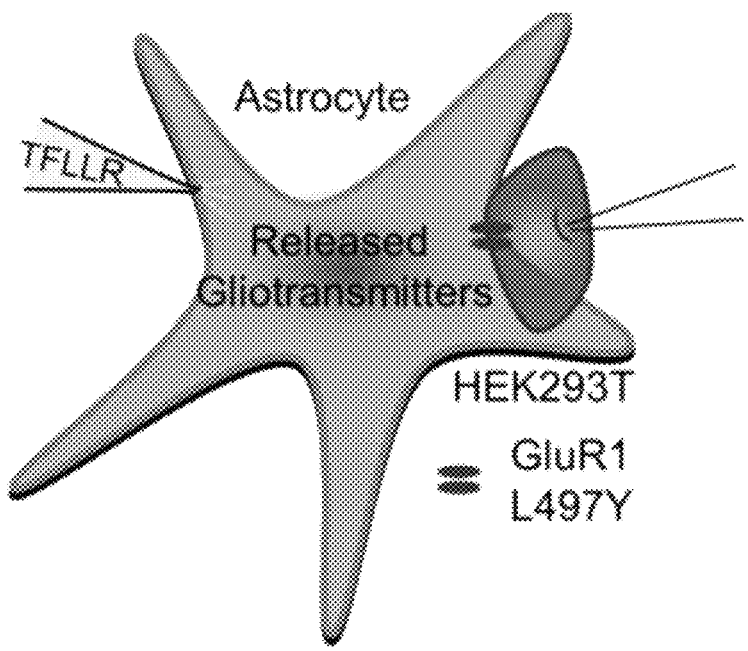
FIG. 1a illustrates Schematic illustration for sniffer patch technique. Left pipette (yellow) indicates the pressure-application of TFLLR, right pipette indicates recording pipette for HEK cell expressing GluR1-L497Y (green, sensor cell), and Red cloud indicates gliotransmitters released from primary culture astrocyte (blue) upon TFLLR application.
Figure 1B:
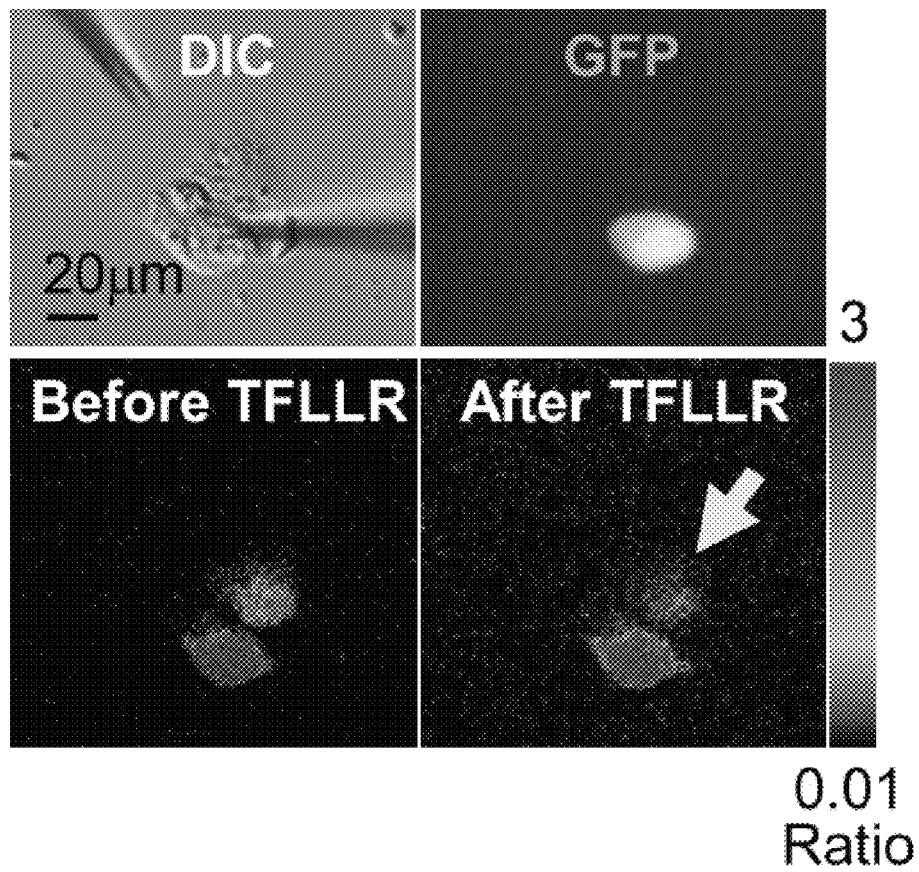
FIG. 1b shows the experimental images for sniffer patch technique. DIC image (upper left) showing two cells with two glass pipettes, GFP indicates sensor cell expressing GluR1-L497Y and EGFP (upper right), Fura-2 loaded astrocyte (source cell) and sensor cells are shown before TFLLR (lower left) and after TFLLR (lower right), and Yellow arrow indicates increased $Ca^{2+}$ in astrocyte.
Figure 1C:
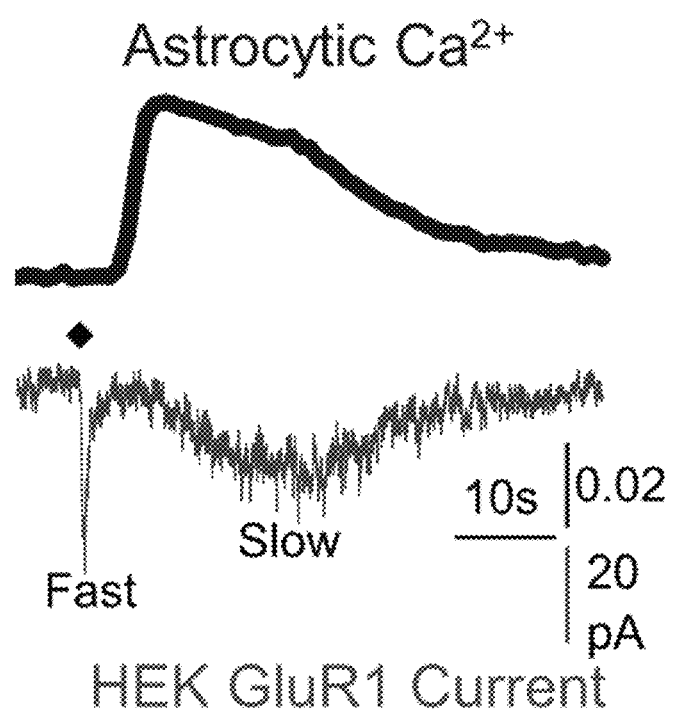
FIG. 1c shows the representative traces recorded from sniffer patch technique. Blue trace shows $Ca^{2+}$ transient recorded from astrocyte and green trace shows whole-cell current recorded from sensor cell ($V_h=-70$ mV) upon TFLLR-pressure application, and Diamond indicates TFLLR application (100 ms, 500 μM).
Figure 1D:
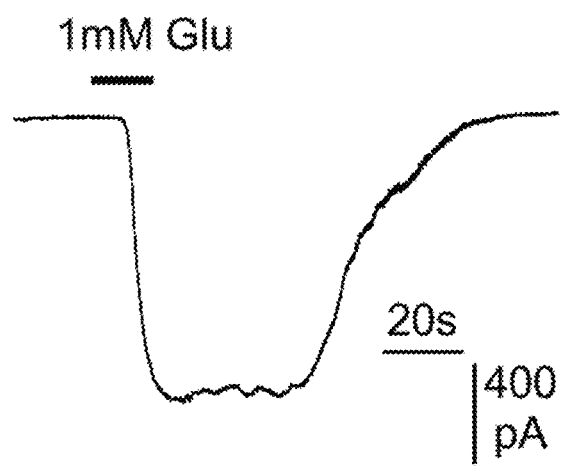
FIG. 1d shows the full activation current recorded by bath application of 1 mM glutamate in sensor cell to measure the level of surface expression of GluR1-L497Y.
Figure 1E:
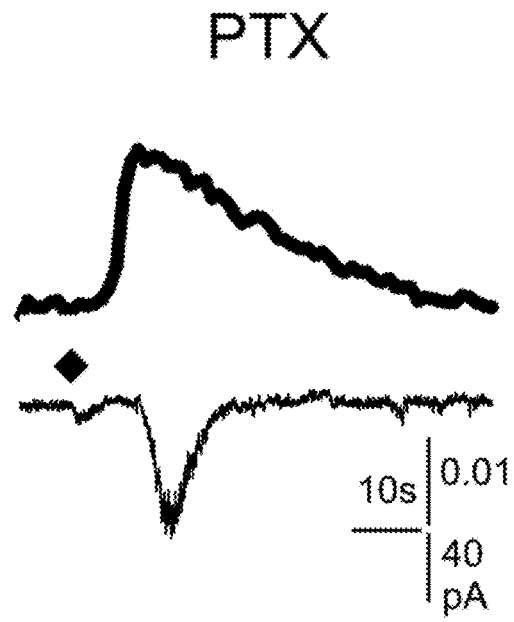
FIG. 1e represents that Lower current trace shows almost complete inhibition of fast-mode in the presence of 1 μg/ml PTX (12-18 hour). The diamond indicates TFLLR application (100 ms, 500 μM).
Figure 1F:
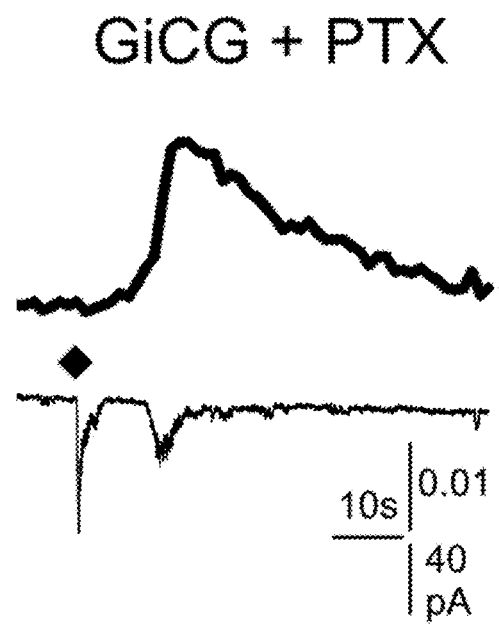
FIG. 1f represents that Lower current trace shows a rescue of fast-mode from PTX-mediated inhibition in PTX treated astrocyte, over-expressing GiCG, a PTX-insensitive form of $G_{ai}$.
Figure 1G:
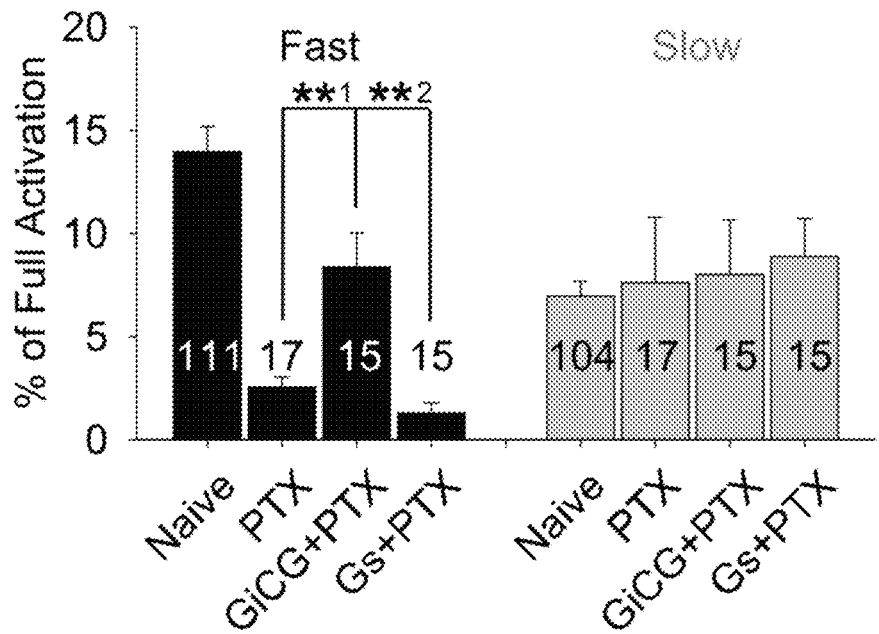
FIG. 1g is a summary bar graph for % of full activation in each indicated conditions. (, p=0.005; *, p=0.001).
Figure 1H:
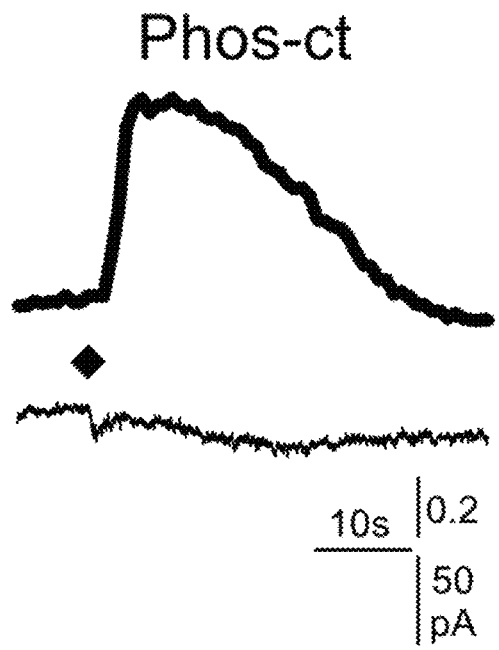
FIG. 1h represents that Lower current trace shows the inhibition of the fast-mode in astrocyte over-expressing the C-terminus of Phosducin which is known to inhibit $G_{ai}$-$G_{\beta\gamma}$ dissociation. The diamond indicates TFLLR application (100 ms, 500 μM).
Figure 1I:
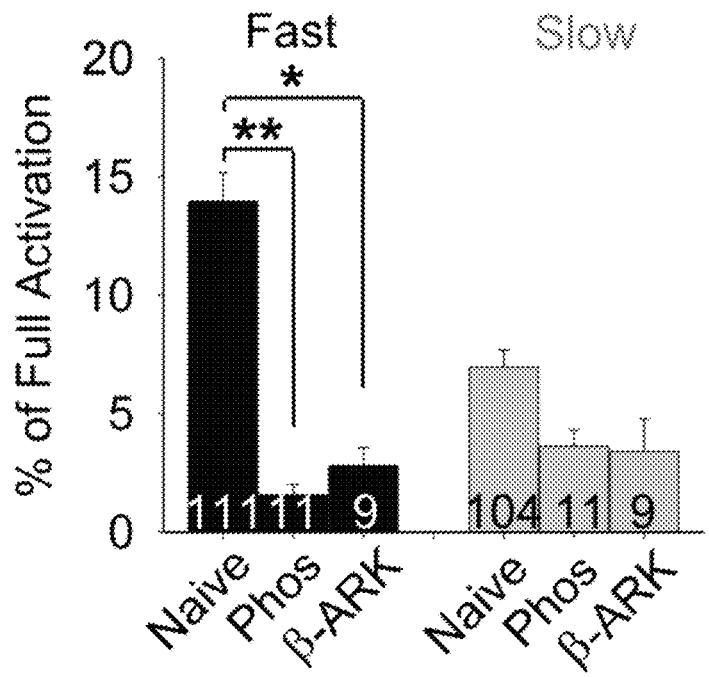
FIG. 1i is a summary bar graph for % of Full activation for inhibition of $G_{ai}$-$G_{\beta\gamma}$ dissociation by C-terminus of Phosducin and β-ARK. (*, p=0.015; ***, p=0.002).
Figure 1J:
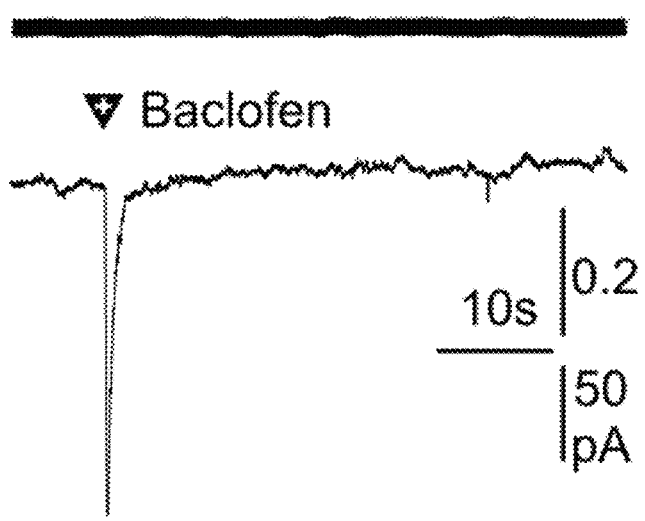
FIG. 1j shows that a representative trace shows that Baclofen (inverted triangle, 100 ms, 300 μM), a $GABA_B$ receptor agonist, induces fast-mode without a $Ca^{2+}$ transient.
Figure 1K:
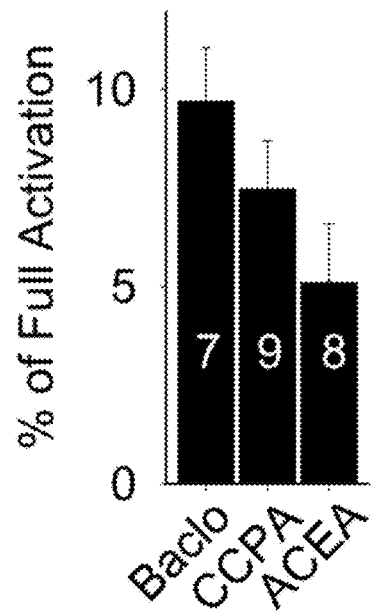
FIG. 1k is a summary graph for the % of full activation of $G_i$-coupled GPCR agonists. CCPA (agonist of Adenosine receptor 1, 100 ms, 1 μM) and ACEA (agonist of Cannabinoid receptor 1, 100 ms, 300 μM) induce fast-mode.
Figure 1L:
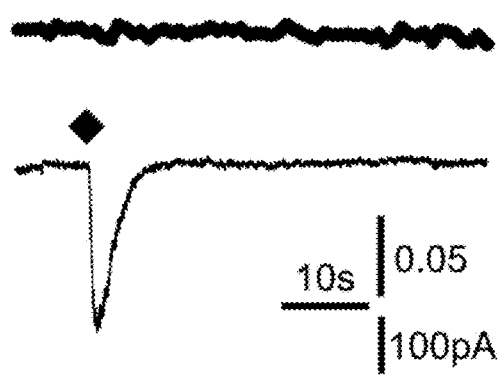
FIG. 1l represents that the Lower trace shows the inhibition of the slow-mode in astrocyte over-expressing RGS-2 inhibiting $G_q$ subunit. The diamond indicates TFLLR application (100 ms, 500 μM).
Figure 1M:
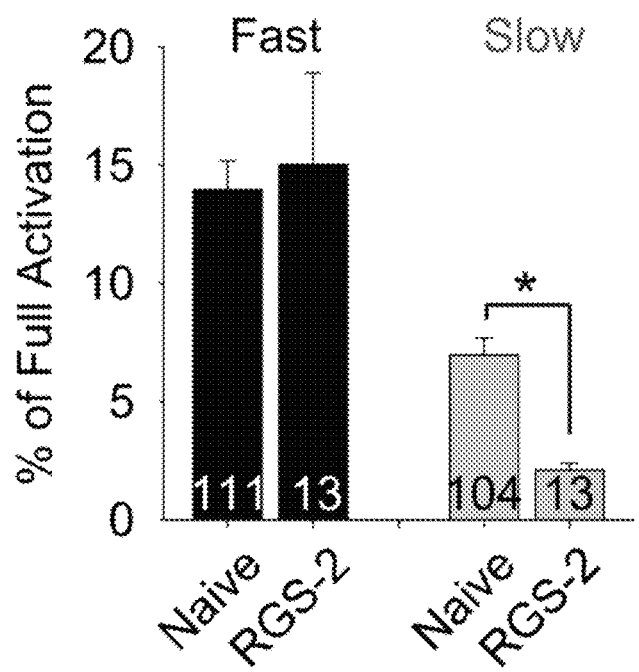
FIG. 1m is a summary graph for % of full activation for RGS-2 expressing astrocytes. (*, p=0.032).

As indicated in FIG. 1*n* and FIG. 1*o*, BAPTA-AM treatment for 30 min eliminated the $Ca^{2+}$ increase, and significantly reduced the low mode of glutamate, but not the fast-mode.

1.4: The Effect of cAMP on the Glutamate Release

To eliminate the possibility that the change in cAMP concentration induce any astrocytic glutamate release, 500 µM forskolin (to activate adenylate cyclase) was pressure-applied for 100 ms. For inhibition of phosphodiesterase activity to increase cAMP, cells were pretreated with 100 µM IBMX for 5 min, and then TFLLR was applied in the presence of 100 µM IBMX (see Experimentation 3-3). The results were shown in FIG. 9*i* to FIG. 9*k*.

As indicated in FIG. 9*i* to FIG. 9*k*, both modes of glutamate release did not affected or involved by cAMP.

1.5: Test for Involvement of Vesicular Exocytosis

We examined whether vesicular exocytosis is involved in the fast and slow-modes of glutamate release. First, we applied hyperosmotic solution which causes exocytotic release of glutamate in neurons.

As indicated in FIGS. 10*a* and 10*c*, it was founded that this evoked no glutamate release from astrocytes. Unlike neurons, astrocytes apparently do not possess glutamate-containing vesicles sensitive to hyperosmotic solution. As additional experiment, Rose Bengal, which inhibited glutamate released by mechanical stimulation did not have any effect on the fast or slow-mode of glutamate released by TFLLR (FIGS. 10*b* and 10*c*).

Treatment of astrocytes with Bafilomycin A1 and Concanamycin A, which should deplete glutamate from synaptic vesicles, appeared to block both fast and slow-modes, presumably due to the fact that these compounds almost completely eliminated the surface expression of GluR1-L497Y in the sensor cell (FIG. 10*d*-10*g*, 10*j*, and 10*k*). Tetanus toxin (TeTX) also caused the similar effect of removing surface GluR1-L497Y (FIG. 10*j* and 10*k*), complicating the interpretation of any results obtained using this toxin (see Experimentation 12).

To avoid the effects of drugs and toxins on the sensor cell, we injected Botulinum toxin B (BoToxB) together with $Ca^{2+}$ indicator dye Fura-2, into individual astrocytes through the patch-pipette. This did not cause any significant effect on the surface expression of GluR1-L497Y on the sensor cell (FIG. 10*m* and 10*p*). We found that BoToxB injection did not have any effect on TFLLR-induced fast and slow-mode (FIGS. 2*a*, and 2*c*), although it completely eliminated glutamate release in the same astrocyte in response to mechanical stimulation (FIGS. 2*a* and 2*d*), as previously reported.

Figure 2A:
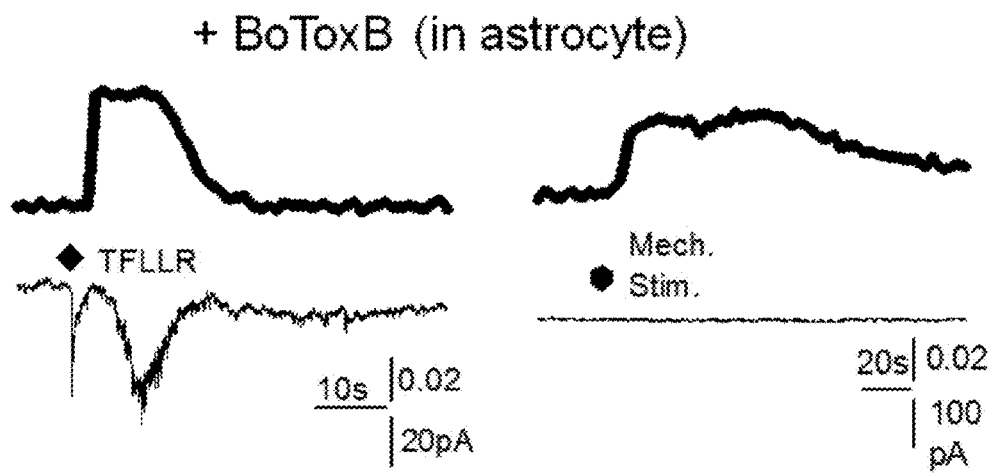
FIG. 2a shows the traces for BoToxB (8 μg/ml, 20 min) injected astrocyte, stimulated with TFLLR (left) and mechanical stimulation (right). The diamond indicates TFLLR and hexagon indicates the mechanical stimulation (touching astrocyte).
Figure 2B:
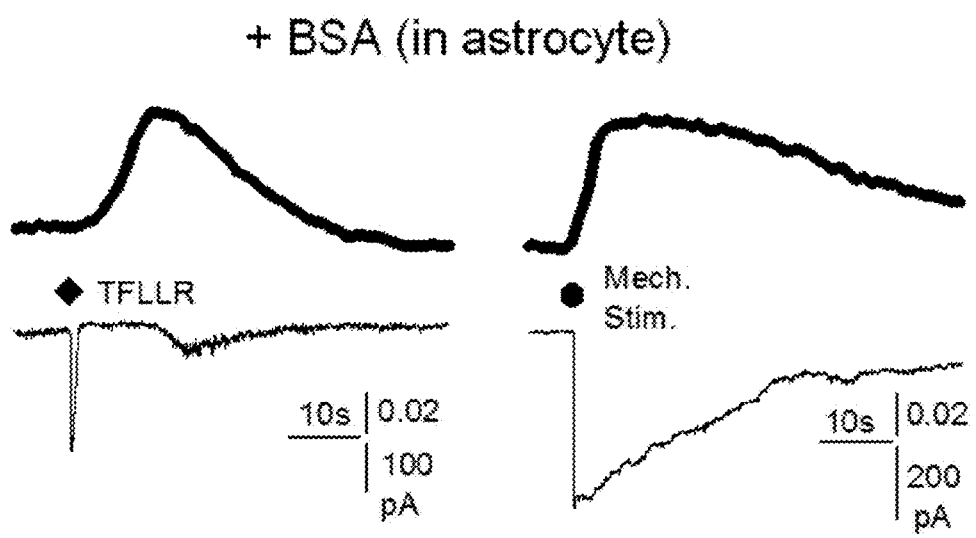
FIG. 2b shows traces for BSA (8 μg/ml, 20 min) injected astrocyte.
Figure 2C:
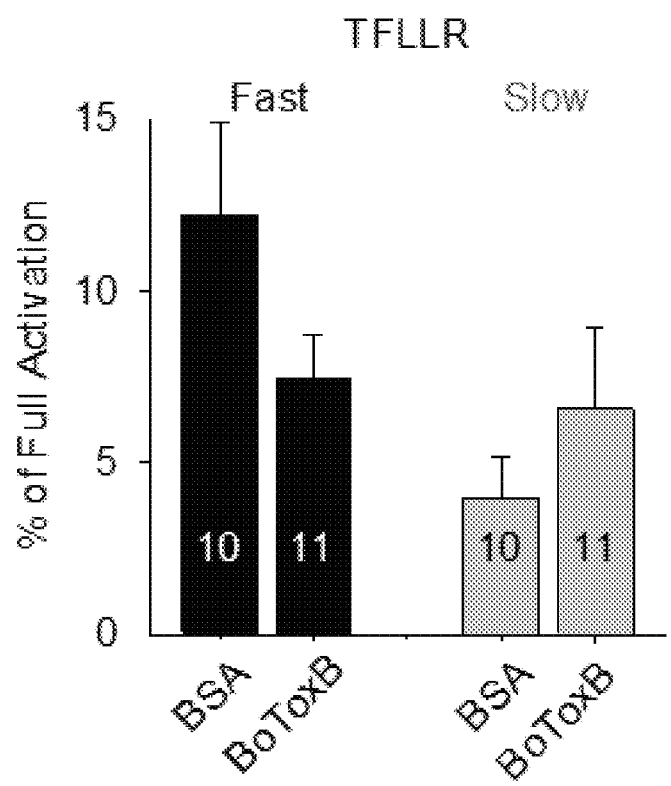
FIG. 2c is a summary graph for % of full activation induced by TFLLR in the condition of the BotoxB and BSA injection. There is no significant difference in fast or slow-mode between two conditions.
Figure 2D:
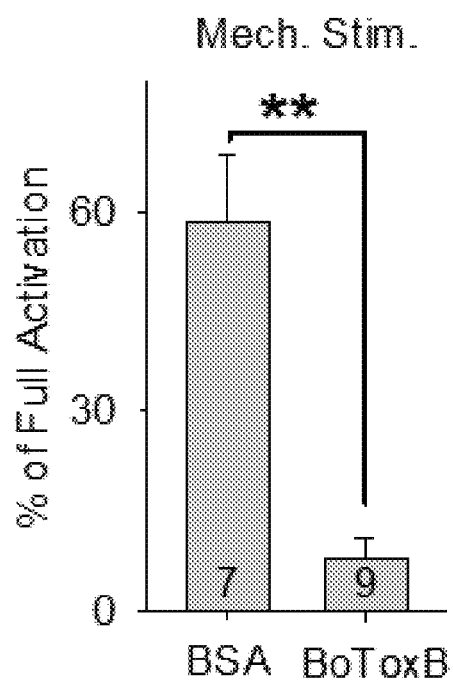
FIG. 2d is a summary graph for % of full activation for mechanical stimulation. (*, p=0.001).
Figure 2E:
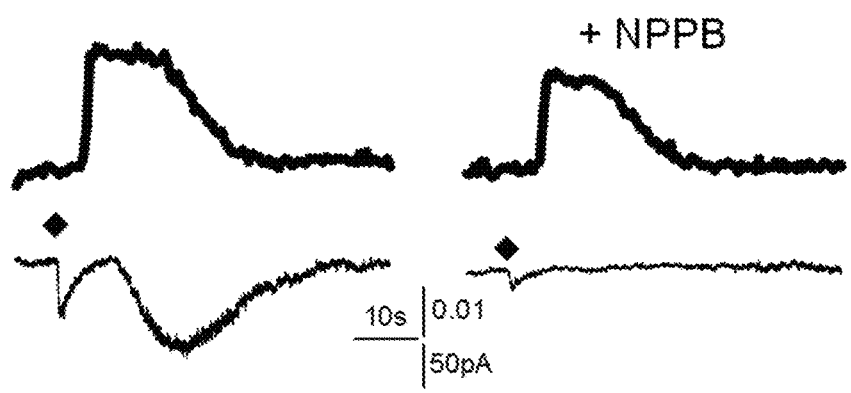
FIG. 2e shows traces for glutamate release before (left) and during 50 μM NPPB (right). The diamond indicates TFLLR application (100 ms, 500 μM).

In contrast, TeTX injection substantially decreased the surface expression of GluR1-L497Y in the sensor cell within 20 minutes (FIGS. 10*l* and 10*p*) and TFLLR-induced glutamate release (FIGS. 10*l* and 10*o*), suggesting that TeTX can readily cross the astrocytic membrane and affect the surface expression of GluR1-L497Y in the neighboring sensor cell. As a control experiment, we injected bovine serum albumin (BSA), instead of BotoxB, and found that BSA did not have any effect on TFLLR-induced fast and slow-mode of glutamate release (FIGS. 2*b*, 2*c*, 10*n* and 10*o*) or on mechanical stimulation-induced glutamate release, as expected (FIGS. 2*b* and 2*d*). From these results we conclude that while glutamate released by mechanical stimulation is mediated by exocytosis, glutamate released by TFLLR is not.

EXAMPLE 2

Figure 2F:
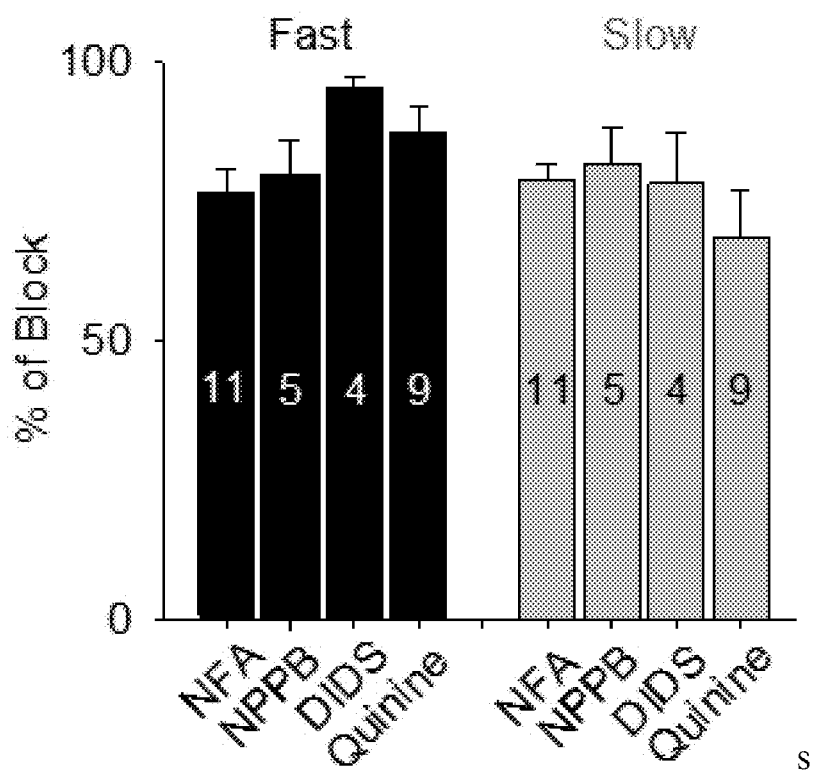
FIG. 2f is a summary graph for % of block for fast and slow-mode induced by TFLLR application in the presence of various blockers, such as DIDS (50 μM for 10 min), DCPIB (50 μM for 10 min), and quinine (100 μM for 10 min).
Figure 2G:
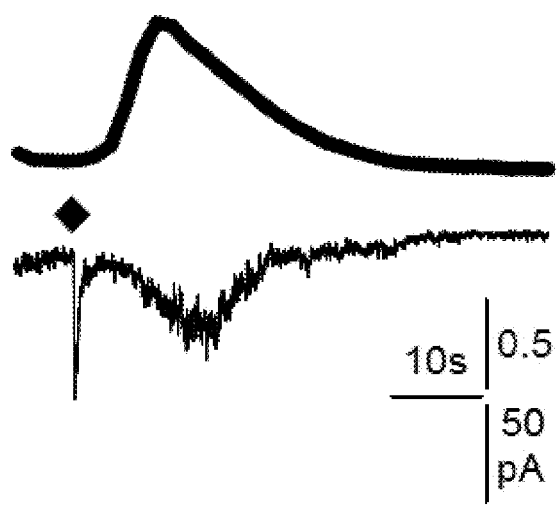
FIG. 2g to FIG. 2j show the traces for each astrocyte, over-expressing control scrambled-shRNA (FIG. 2g), Best1-shRNA (FIG. 2h), TREK-1-shRNA (FIG. 2i), and both Best1- and TREK-1-shRNAs (FIG. 2j).
Figure 2H:
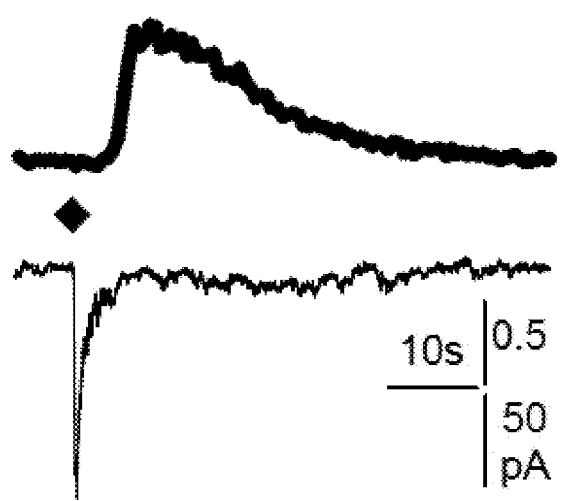
Figure 2I:
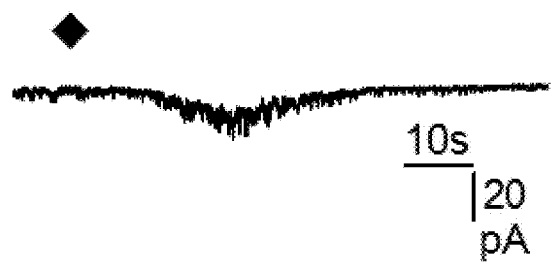

Molecular Identity of Fast and Slow-Modes of Glutamate Release 2-1. Identification of Fast-Mode Release We examined the possibility that TFLLR induces glutamate release from astrocytes via channels or transporters. We screened blockers of various channels and glutamate transporters and found that both the fast and slow-modes of release were blocked by blockers of $Ca^{2+}$-activated anion channel (CAAC), such as NPPB, niflumic acid, DIDS (4,4'-Diisothiocyano-2,2'-stilbenedisulfonic acid) (FIG. 2*e*, 11*a*, and 11*b*), and quinine, which blocks two-pore potassium (K2P) channels (FIGS. 2*f* and 11*c*). Although these blockers are notorious for their non-specific effects, they did not have any effect on the sensor cell, GluR1-L497Y receptor (FIG. 11*d* and 11*e*). Blockers that did not show any significant effect include TTX (voltage-gated sodium channels), $Cd^{2+}$ (voltage-gated $Ca^{2+}$ channels), TEA, $Ba^{2+}$, $Cs^+$ (potassium channel), CBX (gap-junction hemichannel), and DCPIB (volume-sensitive anion channel) (FIG. 11*g*). PPADS (P2X channels) appeared to block the fast-mode (FIG. 11*g*). But this was not interpretable because PPADS had non-specific effects (FIG. 11*e* and 11*h* to 11*j*). From the results of this screening, CAAC and K2P channels emerged as strong candidates as molecular mediators of receptor-mediated glutamate release from astrocytes.

2-2. Identification of Slow-Mode Release

Figure 2J:
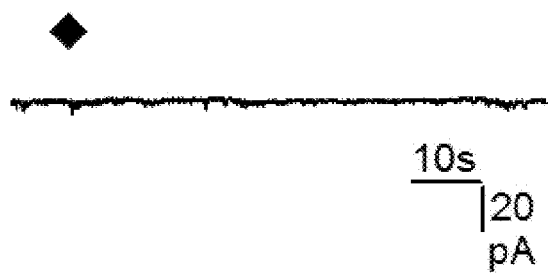
Figure 2K:
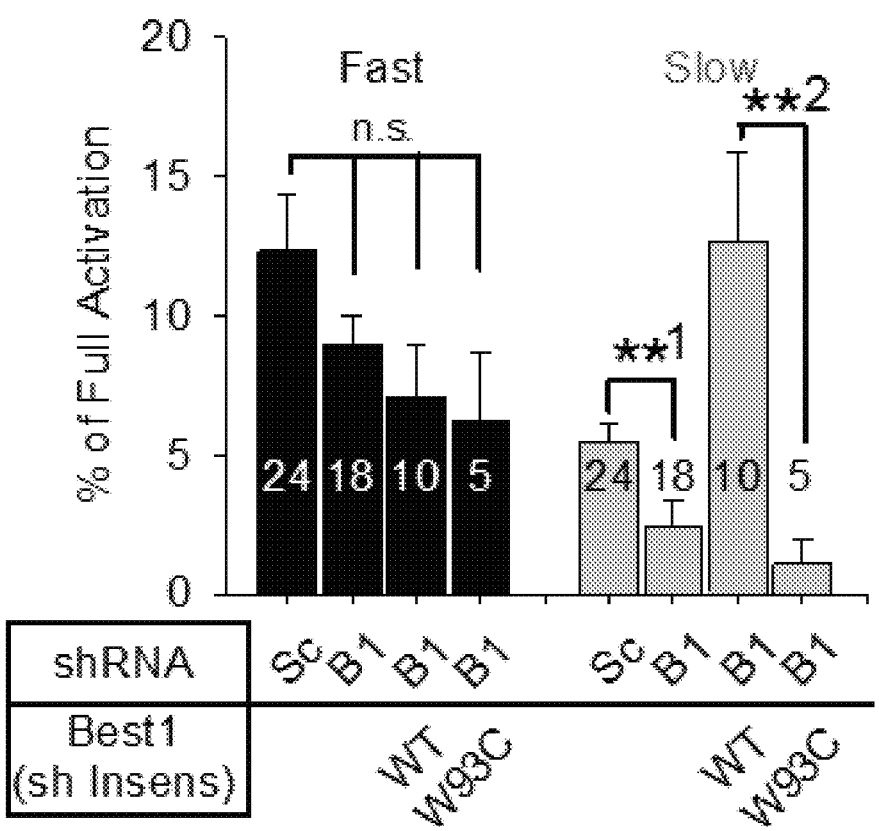
FIG. 2k shows a summary graph for % of full activation of astrocytes, over-expressing Best1-shRNA and co-expressing Best1-shRNA-insensitive, wild type and W93C pore mutant form of Best1 cDNA (1, p=0.008; 2, p=0.009; n.s., non-significance).
Figure 21:
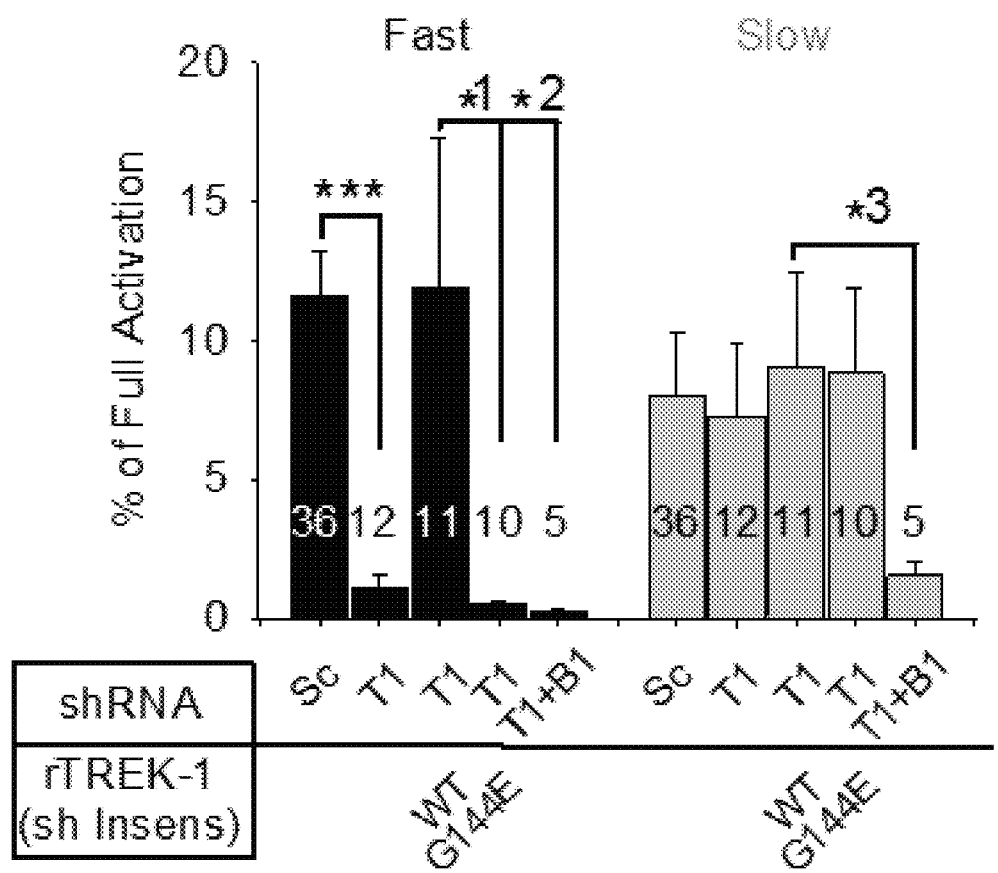

To determine the molecular identity of the slow-mode, we first tested the Bestrophin-1 (Best1) channel, because this $Ca^{2+}$-activated anion channel is highly expressed in hippocampal astrocytes. It also shows unique properties such as permeability to glutamate and GABA, Best1 channel is unlikely to mediate GABA release from hippocampal astrocytes because hippocampal astrocytes do not contain GABA, unlike the cerebellar Bergmann glial cells. Silencing the Best1 gene via specific shRNA for mouse Best1 selectively reduced the slow-mode without significantly affecting the fast-mode (FIGS. 2*g*, 2*h*, and 2*k*) (see Experimentation 2-6). This effect was specific because it was not observed with a control scrambled shRNA and was fully rescued by the co-transfection of Best1-shRNA along with a shRNA-insensitive form of Best1 (FIG. 2*k*). However, the addition of a pore mutation at position 97, from tryptophan to cysteine (Best 1-W93C), failed to rescue the slow-mode, indicating that permeation of glutamate through the pore of Best1 channel is responsible for the slow-mode release of glutamate (FIG. 2*k*). The specificity of the shRNA for Best1, shRNA-insensitive form of Best1, and Best1-W93C (shRNA-insensitive) was previously reported.

For the fast-mode, we next explored the possibility of TREK-1, which is a recently proposed K2P channel in astrocytes. A shRNA specific for mouse TREK-1 was developed (FIG. 12k-12m) and tested for effects on glutamate release. Gene-silencing of TREK-1 selectively eliminated the fast-mode without affecting the slow-mode (FIGS. 2i and 2l) and was fully rescued by rat TREK-1, which is insensitive to mouse TREK-1-shRNA (FIG. 2l). However, the addition of a pore mutation at position 144, from glycine to glutamate (rTREK-1-G144E), failed to rescue the fast-mode, indicating that permeation of glutamate through the pore of TREK-1 is responsible for the fast-mode release of glutamate (FIG. 2l). Finally, co-transfecting the shRNAs for Best1 and TREK-1 eliminated both the fast and slow-modes (FIGS. 2j and 2l).

2-3. TREK-1 Analysis

For the fast-mode, we next explored the possibility of TREK-1, which is a recently proposed K2P channel in astrocytes. The experiment was performed according to Experimentation 2-6. The results were shown in FIGS. 2i, 2j and 2l. A shRNA specific for mouse TREK-1 was developed (FIG. 11k to 11m) and tested for effects on glutamate release. Gene-silencing of TREK-1 selectively eliminated the fast-mode without affecting the slow-mode (FIGS. 2i to 2j) and was fully rescued by rat TREK-1, which is insensitive to mouse TREK-1-shRNA (FIG. 2l) (see Experimentation 2-6). However, the addition of a pore mutation at position 144, from glycine to glutamate (rTREK-1-G144E), failed to rescue the fast-mode, indicating that permeation of glutamate through the pore of TREK-1 is responsible for the fast-mode release of glutamate (FIG. 2l). Finally, co-transfecting the shRNAs for Best1 and TREK-1 eliminated both the fast and slow-modes (FIGS. 2j and 2l).

EXAMPLE 3

Opening of Glutamate-Permeable Channel by Direct Binding of $G_{\beta\gamma}$ to TREK-1

3-1. The N-Terminal of TREK-1

TREK-1-mediated glutamate release is relatively fast and requires $G_i$-$G_{\beta\gamma}$ dissociation. To answer the question, we considered a possibility that $G_{\beta\gamma}$ directly binds to TREK-1 to open a glutamate-permeable channel. A previous yeast two-hybrid screen indicated that TREK-1 interacts with GNG4 (subtype 4 of $G_\gamma$ subunit). The experiment was performed according to the two yeast hybrid screening method of Experimentation 5, and the full down assay of Experimentation 6. The results were shown in FIGS. 3a to 3c, FIG. 12b and FIG. 12c.

Figure 3A:
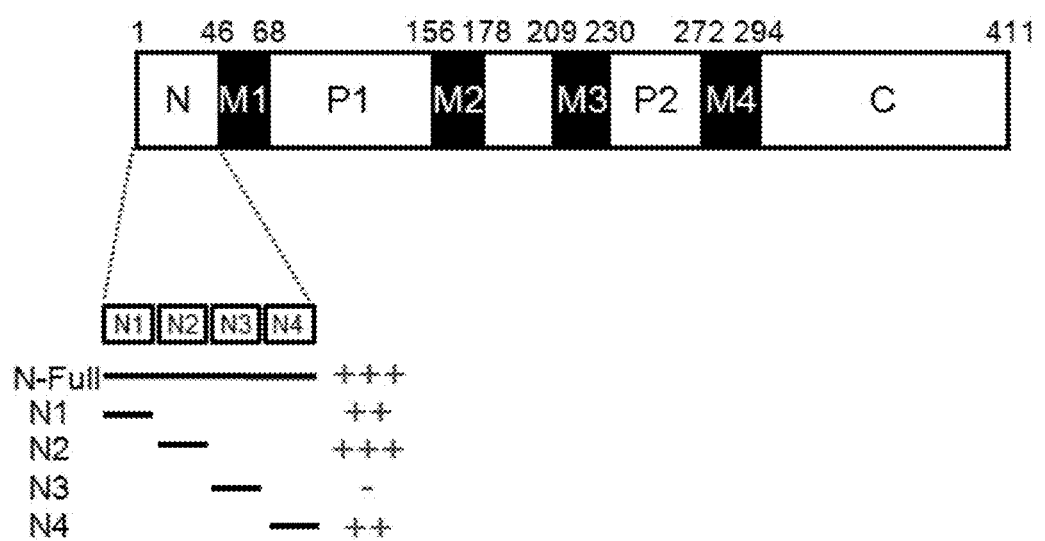
FIG. 3a shows a schematic illustration that represents various domains and amino acid sequence of TREK-1. M1-4 represents four transmembrane domains. P1 and P2 represent pore domain. The N-terminus (1-46 a.a) is divided into 4 segments, N1-4. Red pluses represent the degree of interaction between indicated region of TREK-1 and $G_\square$ subunit (GNG4) from yeast two hybrid system.
Figure 3B:
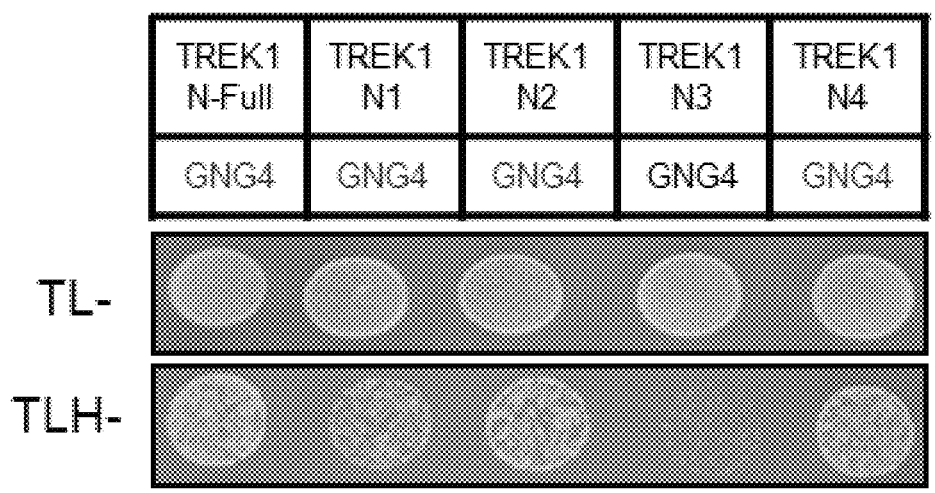
FIG. 3b represents the yeast two hybrid system that shows the interaction between subdomains (N1-N4) of TREK-1 and GNG4 by the presence of yeast colony in TLH (tryptophan, leucine, histidine).
Figure 3C:
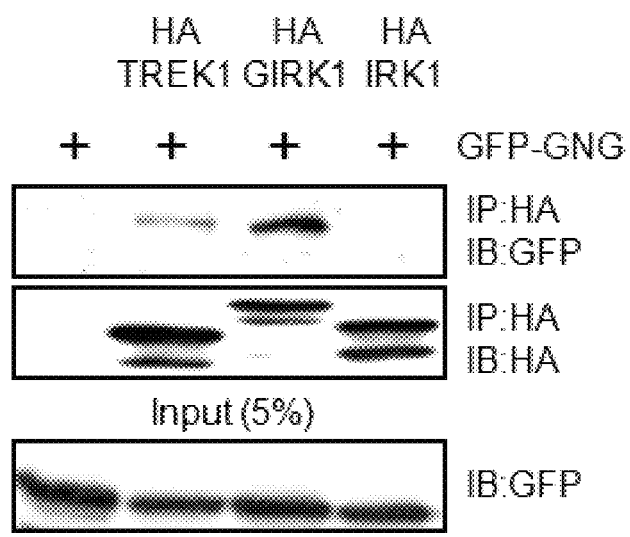
FIG. 3c represents that the immunoprecipitation result shows TREK-1 as well as GIRK 1 interacts with GNG4, but IRK1 does not.

Therefore, we performed a detailed analysis of N-terminal region of TREK-1 (FIG. 3a). Of the 4 segments of N-terminal region of TREK-1, each with 11 or 12 amino acid residues, we found that the N1, N2, and N4 segments strongly interacted with GNG4, while N3 did not (FIGS. 3a, 3b, and 12b). The interaction of TREK-1 N-terminus with GNG4 was also confirmed by co-immunoprecipitation (FIG. 12c). We confirmed the interaction between full-length TREK-1 and GNG4 via co-immunoprecipitation, using the antibodies against Hemagglutinin (HA) and GFP after heterologously expressing GFP-GNG4 and HA-TREK-1 in HEK293T cells (FIG. 3c). As a positive and negative controls, we performed similar experiments with a well-known $G_{\beta\gamma}$-interacting channel, GIRK (G protein-coupled inwardly-rectifying potassium channel) and a non-interacting IRK (inwardly-rectifying potassium channel). We found that GIRK strongly interacted with GNG4, whereas IRK did not (FIG. 3c), as expected.

3-2. Opening of Glutamate-Permeable Channel by Direct Binding of $G_{\beta\gamma}$ to TREK-1

We then asked whether $G_{\beta\gamma}$ can directly open any channels in cultured astrocytes. We performed whole-cell current recording with purified $G_{\beta\gamma}$ in the patch-pipette according to the method of Experimentation 12. The results were shown in FIGS. 3d to 3f, FIG. 3i, and FIGS. 12d to 12f.

Figure 3D:
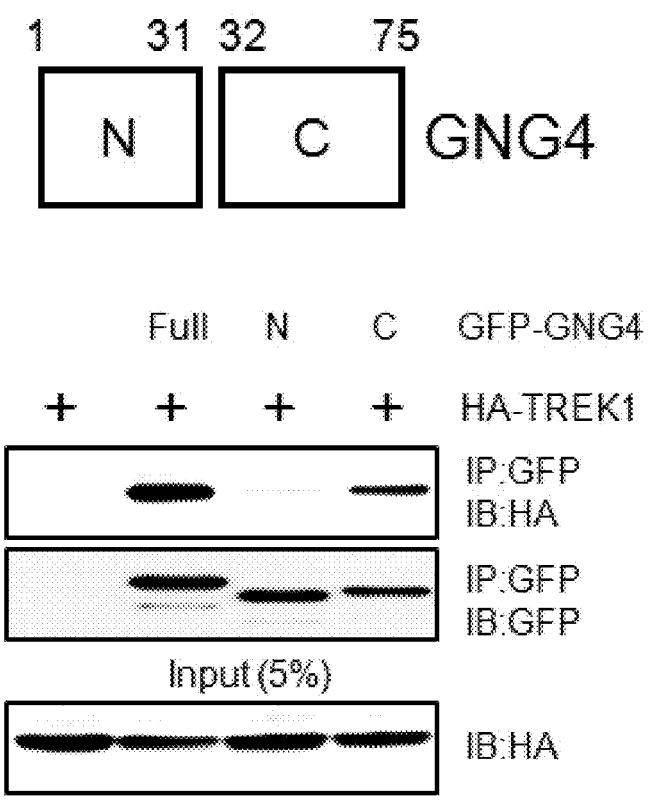
FIG. 3d is I-V curves for $G_{\beta\gamma}$-induced conductance in intracellular solution containing chloride (black) or glutamate (red) and BSA-induced conductance in intracellular solution containing chloride (blue) or glutamate (green). Inset shows a schematic diagram for experiment (in mM, 150 $[Cl]_{in}$, 150 $[Glu]_{in}$, 6.09 nM $G_{\beta\gamma}$: 150 $[Cl]_{out}$).
Figure 3E:
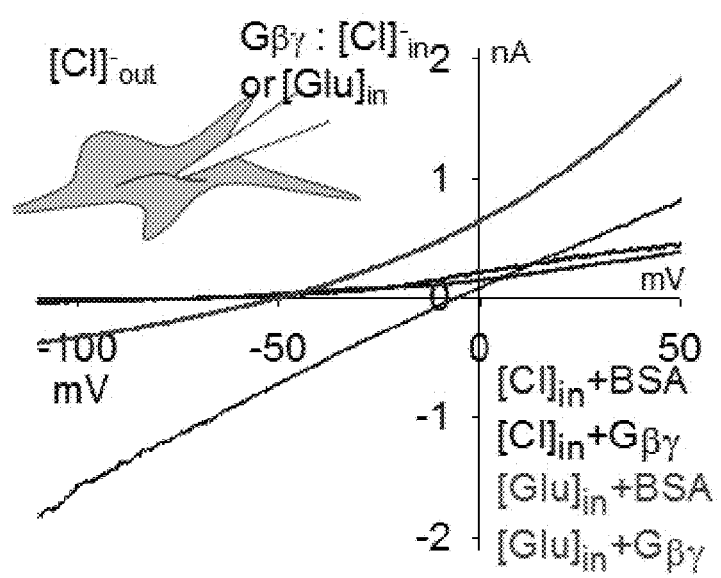
FIG. 3e is a summary graph which shows current amplitudes at −100 mV on four conditions with different internal solutions. (*, p=0.019; ***, p=0.0004).
Figure 3F:
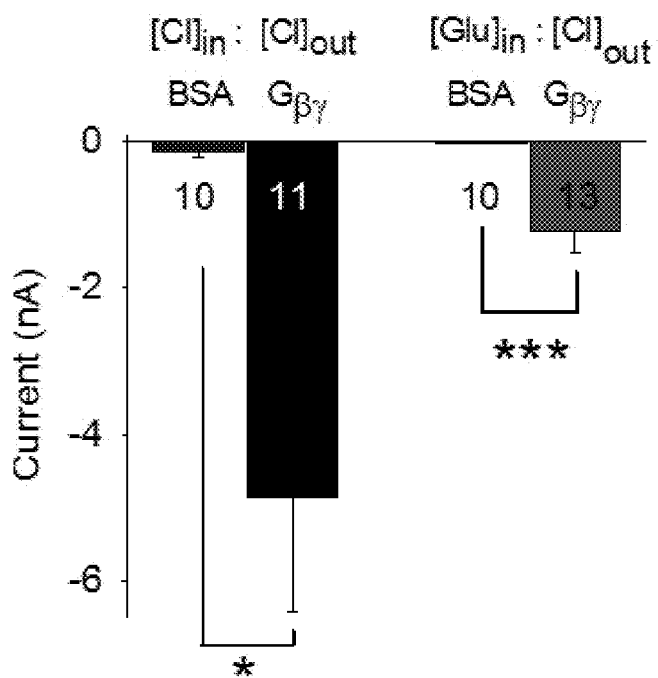
FIG. 3f is a summary graph which shows the reversal potential of the conditions of two internal solutions (black, chloride; red, glutamate). (**, p=0.001).
Figure 3G:
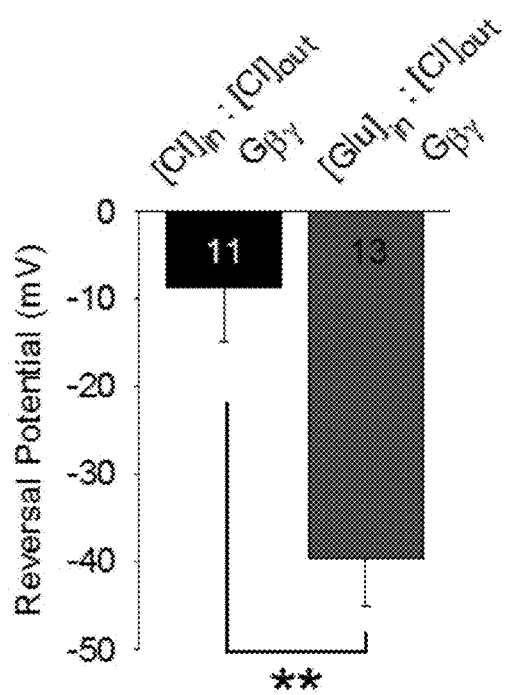
FIG. 3g is I-V curves showing that glutamate permeability depends on TREK-1. Inset shows a schematic diagram for experiment (mM, 150 [Glu]$_{in}$, 6.09 nM $G_{\beta\gamma}$: 150 [Cl$^-$]$_{out}$). $G_{\beta\gamma}$-induced conductance is almost completely removed with the gene silencing of TREK-1 (blue). Co-expression of rat TREK-1 rescues inhibition of $G_{\beta\gamma}$-induced conductance by TREK-1 specific shRNA (red). G144E, pore mutant form of rat TREK-1, does not rescue (green).
Figure 3H:
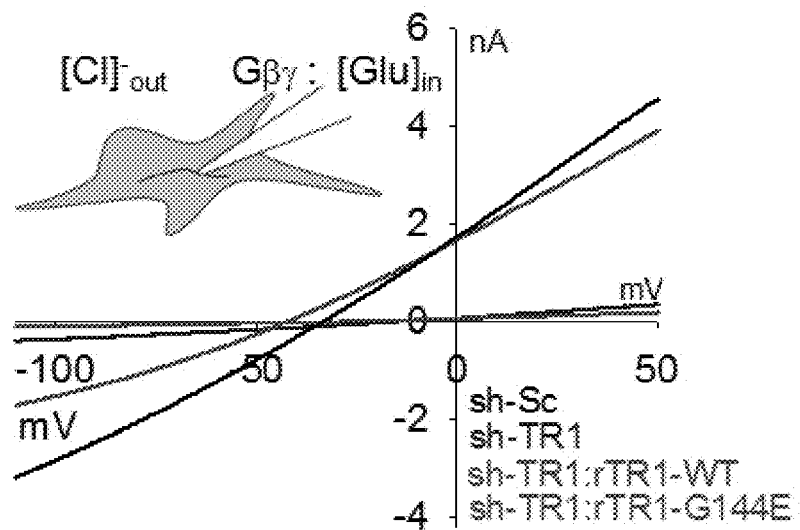
FIG. 3h shows a summary bar graph for current amplitude at −100 mV on indicated conditions. (**, p=0.008; *1, p=0.038; *2, p=0.045).
Figure 3I:
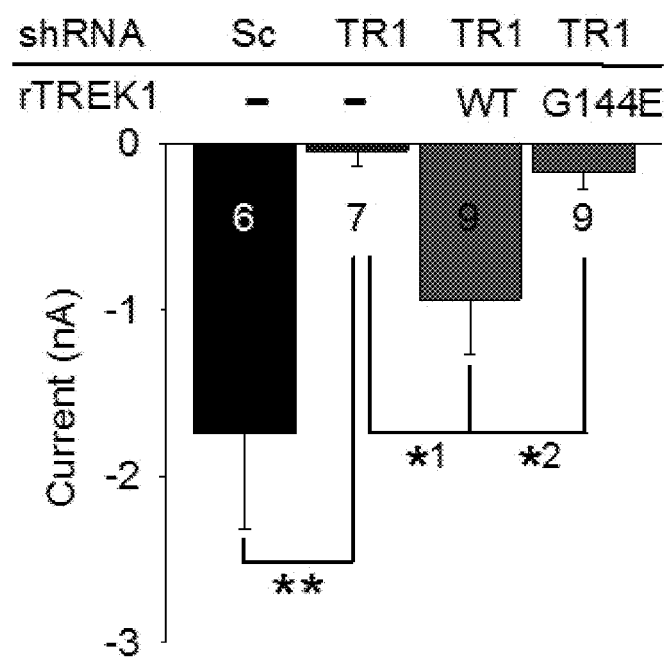
FIG. 3i represents the concentration-response relationship for $G_{\beta\gamma}$ on the conductance under chloride condition (mM, 150 [Cl$^-$]$_{in}$, indicated concentration of $G_{\beta\gamma}$: 150 [Cl$^-$]$_{out}$).
Figure 3J:
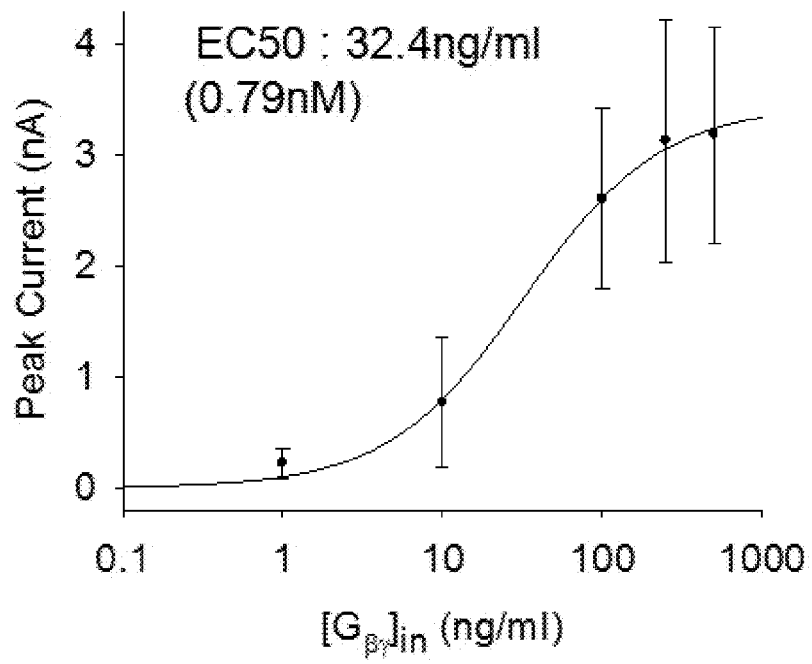
FIG. 3j is I-V curves showing the chloride permeability depending on the competitive peptide. N1 peptides almost inhibit $G_{\beta\gamma}$-induced chloride current (red), whereas $G_{\beta\gamma}$ proteins induce current (black). Inset shows a schematic diagram for the experiment (mM, 150 [Cl$^-$]$_{in}$, 6.09 nM $G_{\beta\gamma}$: 150 [Cl$^-$]$_{out}$).
Figure 3K:
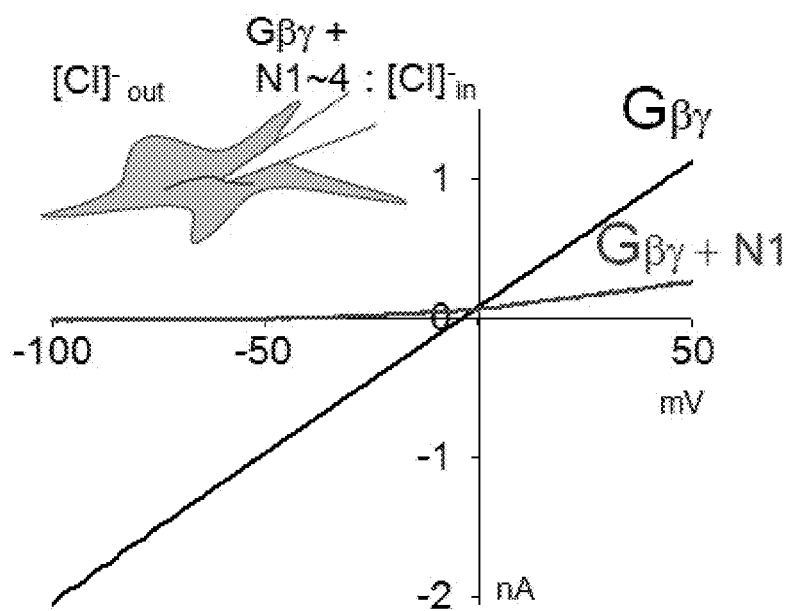
FIG. 3k to FIG. 3m are Traces for 6.09 nM $G_{\beta\gamma}$− (FIG. 3k) and $G_{\beta\gamma}$+100 μM N1 peptide-injected astrocyte (FIG. 3l) and Red arrows indicate measured point on current amplitude at 50 s.
Figure 3L:
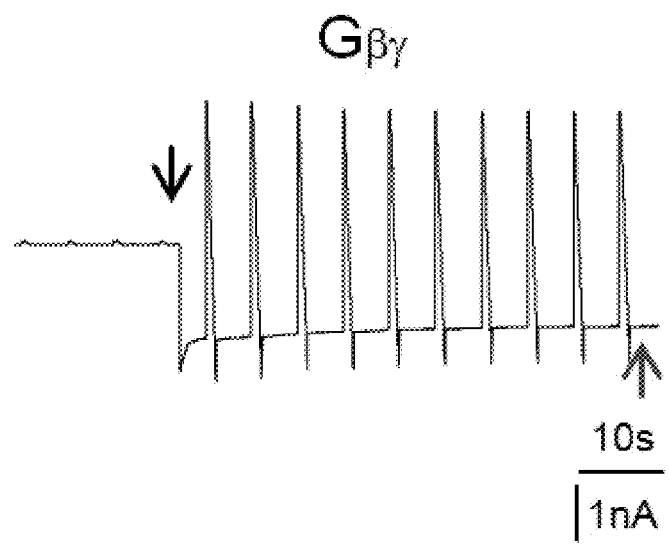
Figure 3M:
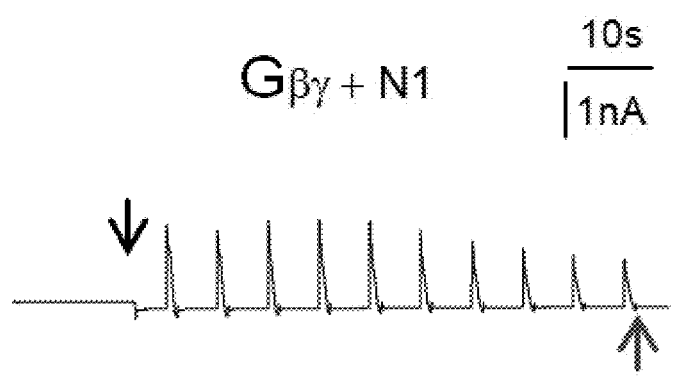
Figure 3N:
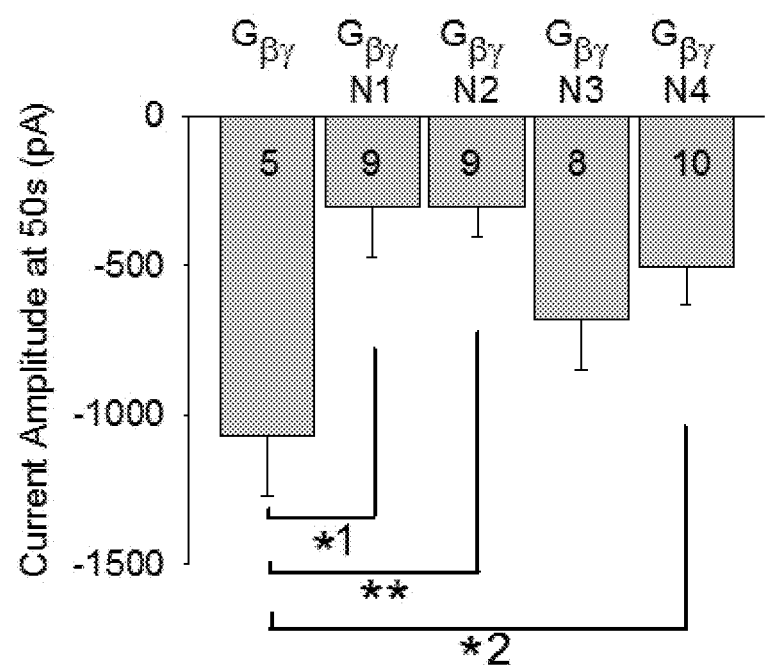
FIG. 3n is a summary bar graph. Values are mean±s.e.m. (*1, p=0.015; **, p=0.002; *2, p=0.026).

We found that a large inward current was induced by intracellularly applied $G_{\beta\gamma}$ upon the membrane rupture ($V_h$=−70 mV). Surprisingly, the reversal potential of this current (−3.8±0.2 mV, n=19) was far away from the equilibrium potential for $K^+$ (−70 mV) or $Na^+$ (40 mV), but was near the $Cl^-$ equilibrium potential (0 mV, FIG. 12d-120. Ion substitution experiments showed that the $G_{\beta\gamma}$-induced current was mostly carried by $Cl^-$ ion because of the linear current-voltage (I-V) relationship and reversal potential near 0 mV, observed when identical $Cl^-$ concentrations were present on both sides of membrane (FIG. 3d, black trace). As a control, we used bovine serum albumin (BSA), which did not induce any significant current (FIG. 3d, blue trace). To determine whether the conductance shows permeability to glutamate, we substituted $Cl^-$ in the intracellular pipette solution with glutamate and found that $G_{\beta\gamma}$ induced a significant inward current at −100 mV with reversal potential around −40 mV (FIG. 3d, red trace), indicating a significant glutamate permeability. From the average shift in reversal potential of −30.9 mV produced by the substitution of intracellular $Cl^-$ with glutamate (FIG. 3f), we calculated the permeability ratio of glutamate to Cl— ($P_{glutamate}/P_{Cl^-}$) to be 0.27, using the Goldman-Hodgkin-Katz equation. In the absence of $G_{\beta\gamma}$, the conductance for glutamate as well as that for $Cl^-$ was negligible (FIG. 3e). From the concentration-response relationship, EC50 for $G_{\beta\gamma}$ was determined to be 32.4 ng/ml (0.79 nM) (FIG. 3i).

3-3. Interaction Between N-Terminal of TREK-1 and $G_{\beta\gamma}$

To test whether the $G_{\beta\gamma}$-induced glutamate conductance is mediated by TREK-1, we performed a similar experiment after silencing the TREK-1 gene with shRNA. The experiment was performed according to Experimentation 12.

Compared to the scrambled shRNA (FIG. 3g black trace and 3h), we found that mouse TREK-1-shRNA eliminated the $G_{\beta\gamma}$-induced conductance (blue trace), which was significantly rescued by co-expression of rat TREK-1 (red trace). The pore mutant, rTREK-1-G144E failed to rescue the $G_{\beta\gamma}$-induced conductance (green trace). These results indicate that TREK-1-mediates the glutamate conductance induced by $G_{\beta\gamma}$. Because N1, N2, and N4 of TREK-1 interact with GNG4, we tested for functional interaction using these competitive peptides (SEQ ID NO: 2, 3, and 4). Inclusion of competitive peptides, N1, N2, and N4 in the patch pipette significantly reduced $G_{\beta\gamma}$-induced chloride currents, suggesting that these peptides inhibit the interaction between N-terminus of TREK-1 and $G_{\beta\gamma}$ (FIGS. 3j to 3m) (see Experimentation 12).

Figure 4B:
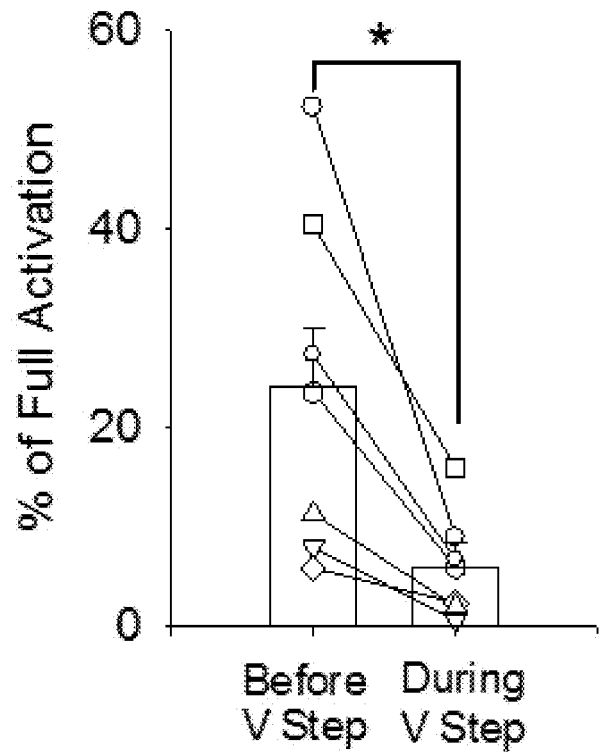
Figure 4C:
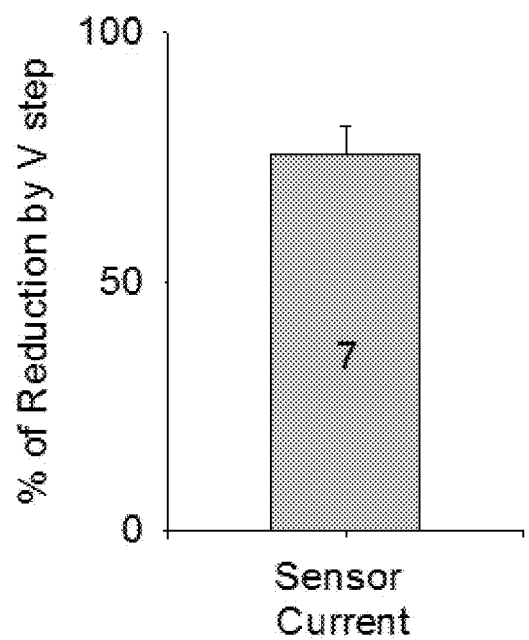
Figure 4D:
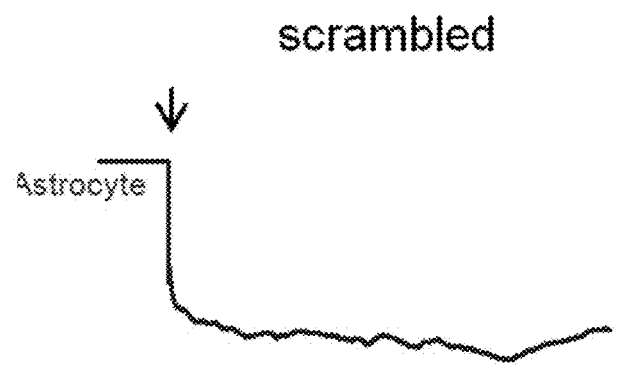
Figure 4E:
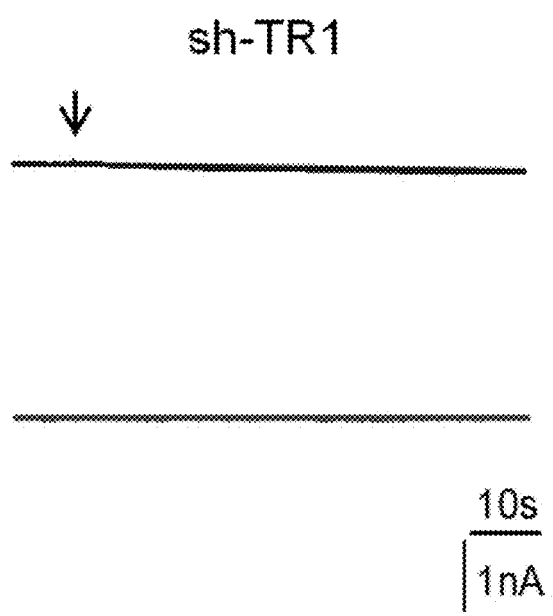
Figure 4F:
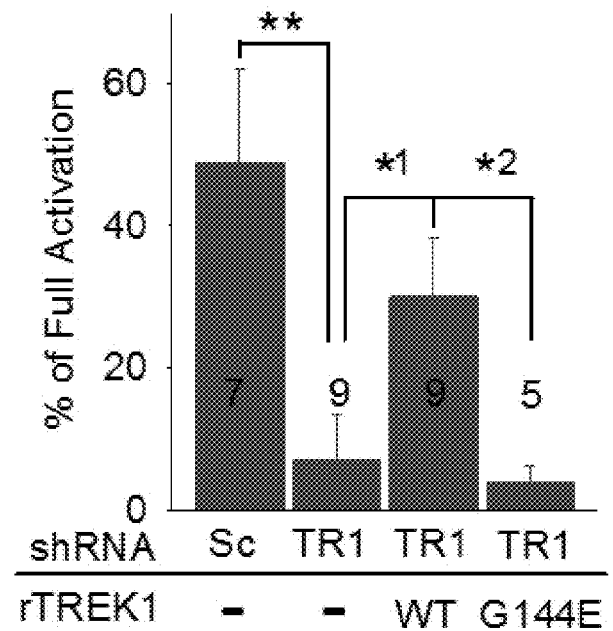

To determine whether activation of TREK-1 by $G_{\beta\gamma}$ can release glutamate from astrocytes, we performed two-cell sniffer-patch. Under this configuration, two patch pipettes were used: one containing both $G_{\beta\gamma}$ and 5 mM glutamate, to record from an astrocyte, and the other for a sensor cell expressing GluR1-L497Y to detect released glutamate (see Experimentation 4). Upon membrane rupture, the astrocyte showed a large inward current (Vh=−70 mV), while the sensor cell displayed a substantial parallel current representing glutamate released from the neighboring astrocyte (FIGS. 4a and 4b). Outflow of glutamate from astrocytes was dependent on the electrochemical gradient, because changing the holding potential from $V_h$=−70 mV to $V_h$=+70 mV, reduced glutamate release by about 75% (FIG. 4a-4c), as predicted by the Nernst equation. This glutamate release was eliminated by silencing the TREK-1 gene in astrocytes and was rescued by co-expression of rat TREK-1 (FIG. 4d-4f). The pore mutant, rTREK-1-G144E failed to rescue (FIG. 4O. These results indicate that astrocytic glutamate release can be directly induced by $G_{\beta\gamma}$, and that TREK-1 mediates this release by direct permeation of glutamate through its pore.

Figure 4G:
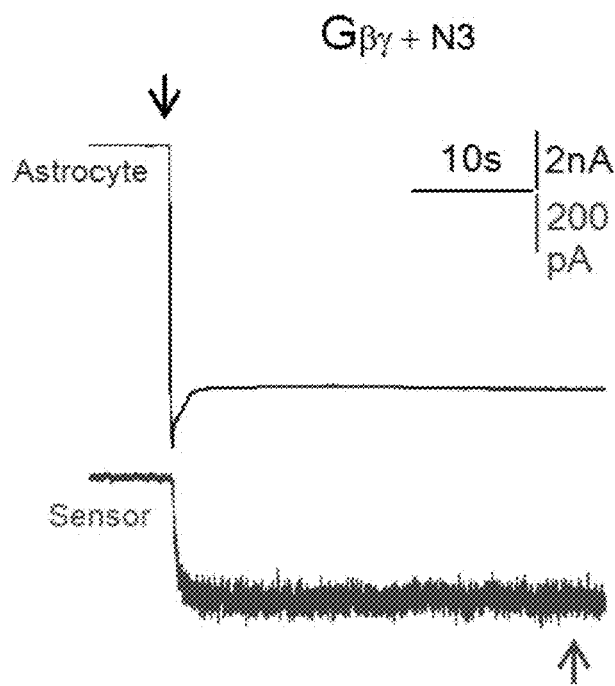
Figure 4H:
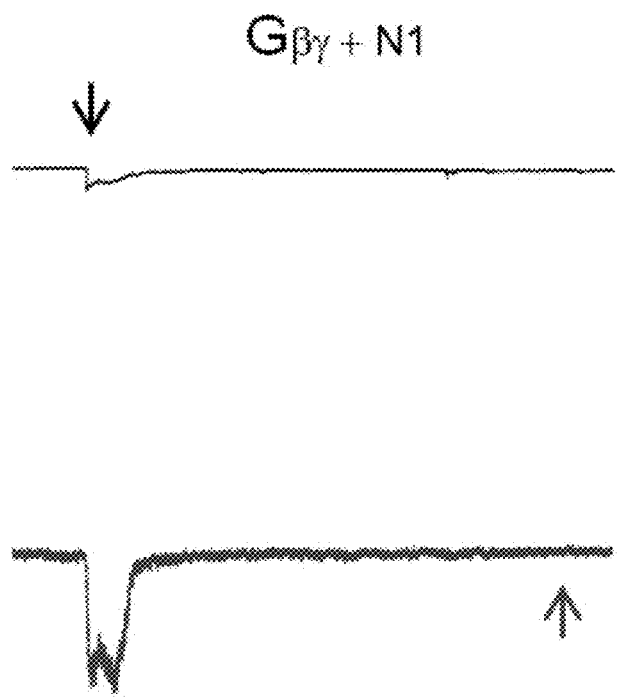
Figure 4I:
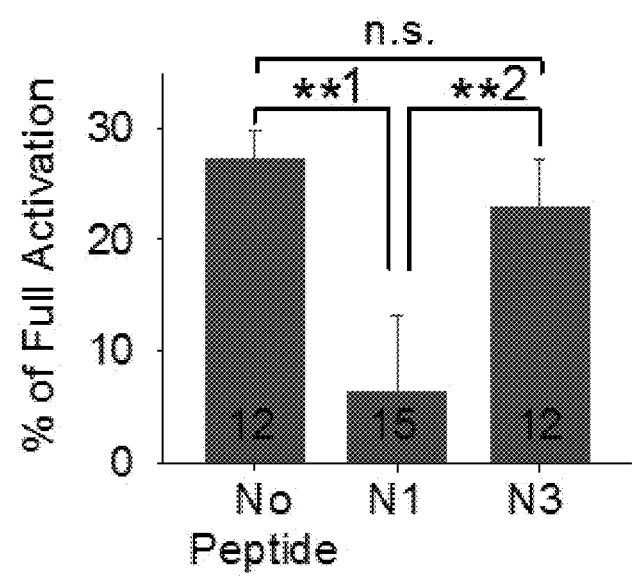

Finally, we tested whether TREK-1-mediated glutamate release requires direct binding of $G_{\beta\gamma}$ to TREK-1 by utilizing the N-terminal segments of TREK-1 to compete for binding of $G_{\beta\gamma}$ to TREK-1. We performed two-cell sniffer patch and found that N1 peptide significantly reduced the $G_{\beta\gamma}$-induced glutamate release as well as $G_{\beta\gamma}$-induced current (FIGS. 4h and 4i), whereas N3 had no significant effect compared to the control condition without any peptide (FIGS. 4g and 4i).

EXAMPLE 4

Glutamate Permeable Channel Best 1

Best1 channel is activated by intracellular $Ca^{2+}$ ($EC_{50}$=150 nM) with considerable permeability to GABA and hippocampal astrocytes express CAAC with glutamate permeability.

To test whether heterologously expressed Best1 is also permeable to glutamate, we measured Best1-mediated anion conductance in HEK293T cells expressing mouse Best1 gene using patch pipette solution with high Ca2+ (4.5 μM free Ca2+) for maximal channel activation and or glutamate as the solely permeant anion (145 mM Cl⁻ or glutamate). The current-voltage (I-V) relationship of currents flowing through Best1 was determined as illustrated in FIG. 5a (black trace) (see Experimentation 12).

Figure 5A:
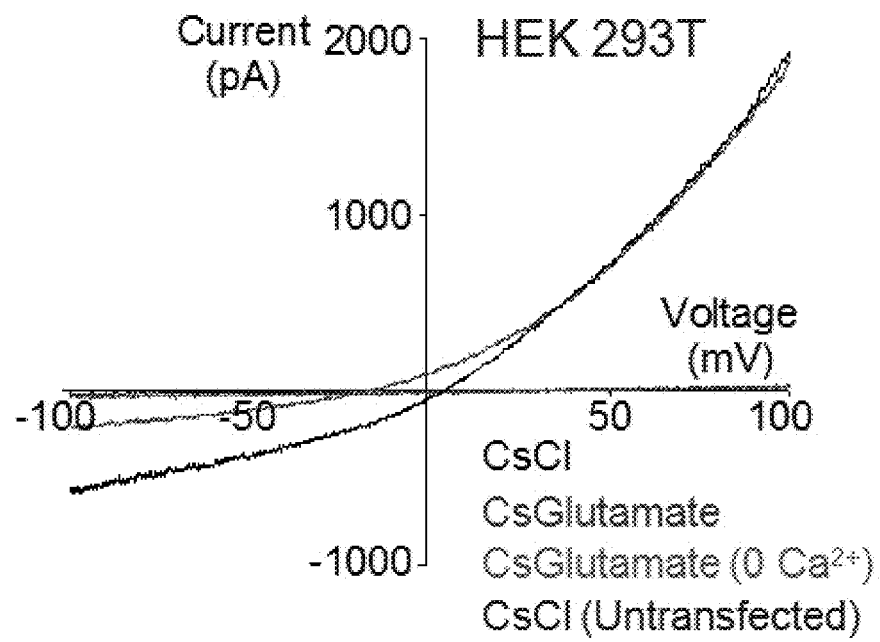
Figure 5B:
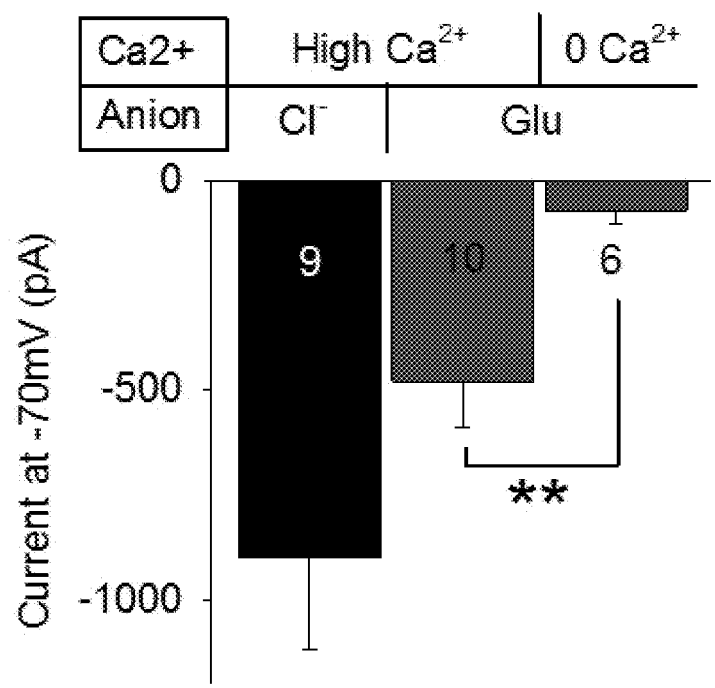

We found a significant Ca2+-induced conductance carried by the efflux of Cl⁻ or glutamate at −70 mV, which was eliminated by the absence of free $Ca^{2+}$ in the pipette solution (FIGS. 5a and 5b). The estimated permeability ratio of glutamate and Cl⁻ was Pglutamate/PCl=0.67 (Erev of internal Cl—: 1.9±0.8 mV, n=9; Erev of internal glutamate: −6.4±2.0 mV, n=11; p=0.0019) according to the Goldman-Hodgkin-Kats equation. These results indicate that Best1 channels show substantial permeability to glutamate, consistent with the previous reports showing that Best1 channel is permeable to large anions such as GABA, gluconate, and glutamate.

Figure 5C:
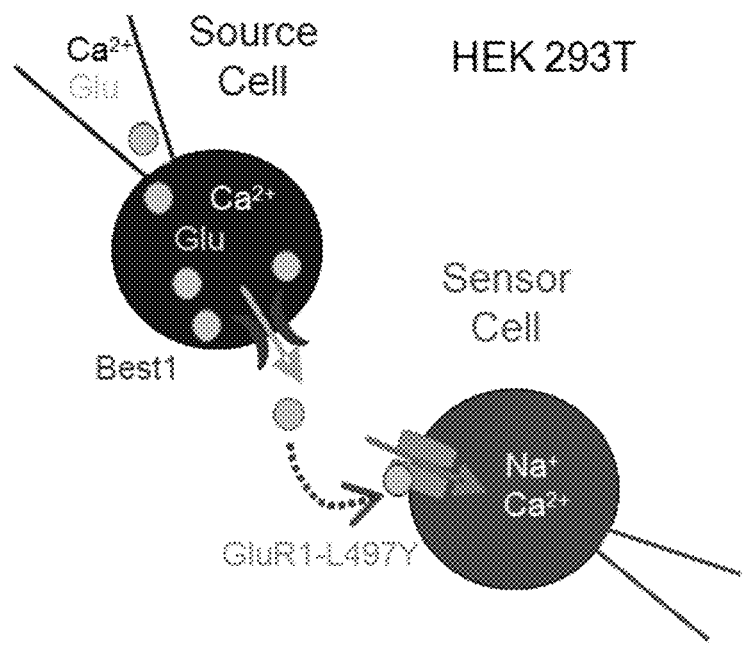

To determine whether such glutamate efflux through Best1 channel can be detected by a neighboring cell, we performed a two cell sniffer patch (FIG. 5c) (see Experimentation 4). In this assay, glutamate released from one cell (source cell; Best1-expressing HEK293T cell) can be detected by the neighboring cell (sensor cell; GluR1-L497Y-expressing HEK293T cell). The internal solution for cells expressing Best1 channel contained Cl— or glutamate for anion, and upon rupture of membrane Best1 was activated by high Ca2+ in the pipette solution (~4.5 free Ca2+; FIG. 5c) (see Experimentation 4).

Figure 5D:
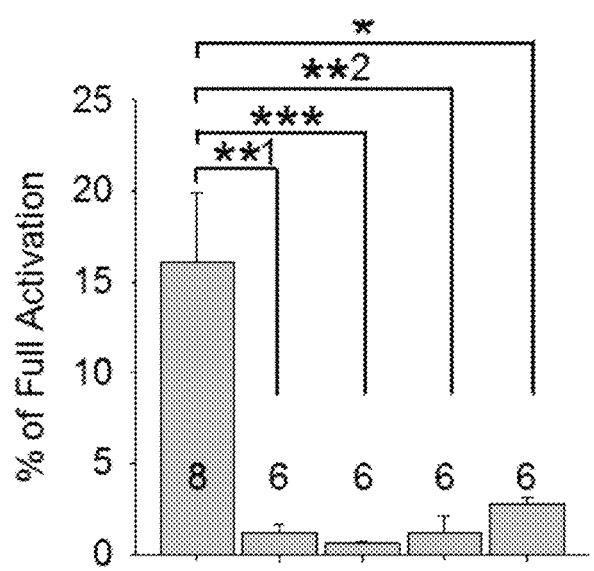

We found that Best1 displayed a significant glutamate conductance (FIG. 5e, top blue trace; indicated by an inward current flow at −70 mV from the source cell), and that this current was associated with GluR1-mediated inward current from sensor cell (FIG. 5e, bottom green trace), indicating that there is a release of glutamate from Best1-expressing cell. To quantify the amount of glutamate release, we normalized the response to the maximal current induced by bath application of 1 mM glutamate. We found that the released glutamate to neighboring cells depended on permeation through $Ca^{2+}$-activated Best1 (FIG. 5d), because it was absent (1) when Best1 was not expressed, (2) when glutamate was replaced by Cl⁻, (3) when $Ca^{2+}$ was absent (FIG. 5f), and (4) when the source cell expressed the pore mutant of Best1 (W93C). These results demonstrate that Best1 is a $Ca^{2+}$-activated anion channel, which is permeable to glutamate and capable of releasing detectable levels of glutamate into the extracellular environment.

EXAMPLE 5

Differential Localization of TREK-1 and Best1 and Neuronal Targets

To see if the same kind of glutamate release is observed ex vivo, we performed sniffer-patch experiment and recorded CNQX-sensitive glutamate release from a single, acutely isolated, GFP-positive hippocampal astrocyte, prepared from the brain slices of adult GFAP-GFP transgenic mice (FIG. 6a). We similarly observed fast and slow-mode of glutamate release (FIGS. 6b and 6c), with similar kinetic properties (fast-mode latency: 58.0±7.5 ms, n=15; slow-mode peak: 31.3±4.4 s, n=15), implying that the same signaling pathways and molecules are involved in vivo.

Astrocytes show elaborate structures in vivo with several key cellular compartments. Of these structures, microdomains tightly wrap around each synapse. To determine the subcellular distribution of the Best1 and TREK-1 channels and thus to predict the in vivo function, we performed electron microscopic immunohistochemistry with antisera against Best1 or TREK-1 and against GFP in GFAP-GFP mice (see Experimentation 2-6). We found that Best1 channels were preferentially expressed at the surface membrane of microdomains adjacent to glutamatergic synapses (FIG. 6d), compared to other cellular compartments such as cell body and large processes (FIG. 6f and FIG. 13a-13c) (see Experimentation 11). The labeling in the large processes was located inside the processes rather than near or at the plasma membrane (FIG. 13b), suggesting that these proteins are being transported out to the distal microdomains. In contrast to Best1, TREK-1 antibody showed opposite distribution pattern; namely at the surface of cell body and processes but not at the microdomains (FIG. 6e, 6f and FIGS. 13d to 13f).

Next, the total amount of glutamate release from a single astrocyte was estimated based on the experimental values of sniffer-patch recording, using a diffusion model to fit the experimental measurements. The model was optimized to consider the geometrical constraints of sniffer-patch and to capture the diffused-away glutamate molecules that the sensor failed to detect (FIG. 7a). We calculated that one typical astrocyte releases 0.34 fmole of glutamate during the fast-mode and 1.35 fmole during the slow-mode (FIGS. 7b and 7c). These values could be compared to 2.64 fmole for the mechanical stimulation-induced glutamate release at the peak of response (FIGS. 7b and 7d) (see Experimentation 10). These estimations are comparable to the previously reported estimations [0.078-0.2 fmol by glutamate imaging, and 3 fmol by HPLC].

Using the same diffusion model, we simulated the glutamate release from the point sources uniformly distributed on the astrocytic membrane and predicted the concentration of glutamate from 10-40 nm away from the neuronal membrane to mimic the astrocyte-neuron interaction (FIGS. 7h and 7i). Because the cytosolic glutamate concentration in astrocyte is as high as 2-10 mM, glutamate is assumed to flow out, down the gradient when TREK-1 and Best1 channels open. The simulated glutamate concentration for the fast-mode release via TREK-1 was about 100 μM (FIG. 7e) at the target receptor of the apposing neuronal membrane, whereas for slow-mode via Best1 was about 0.9 μM (FIG. 7O. From these values, we can predict that the slow-mode will preferentially activate neuronal NMDA receptors, whereas the fast-mode will preferentially activate mGluR in addition to NMDA receptor, according to the reported concentration-response relationship for each glutamate receptor (FIG. 7g). However, the actual counterpart glutamate receptor in neuron will depend on the precise location of the astrocytic TREK-1 and Best1 in relation to apposing neuronal NMDA receptor or mGluR.

The invention claimed is:

1. A method for screening a glutamate-release inhibitor in an astrocyte, said method comprising the steps of:
   preparing an astrocyte-containing sample;
   contacting a candidate material to the sample; and
   detecting the activation of a glutamate-permeable potassium channel or $Ca^{2+}$-activated anion channel in the sample,
   wherein said candidate material is determined to be glutamate-release inhibitor in an astrocyte when the channel is found to be inactivated.

2. The method of screening according to claim 1, wherein the potassium channel is TREK-1 channel, or the $Ca^{2+}$-activated anion channel is a TREK-1 channel.

3. The method of screening according to claim 1, wherein the activation of a glutamate-permeable potassium channel or $Ca^{2+}$-activated anion channel is detected by the measurement of an inward current change using sniffer patch method.

* * * * *